United States Patent
Bernick et al.

(10) Patent No.: US 9,289,382 B2
(45) Date of Patent: *Mar. 22, 2016

(54) VAGINAL INSERTED ESTRADIOL PHARMACEUTICAL COMPOSITIONS AND METHODS

(71) Applicant: TherapeuticsMD, Inc., Boca Raton, FL (US)

(72) Inventors: Brian A. Bernick, Boca Raton, FL (US); Julia M. Amadio, Boca Raton, FL (US)

(73) Assignee: TherapeuticsMD, Inc., Boca Raton, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/624,051

(22) Filed: Feb. 17, 2015

(65) Prior Publication Data

US 2015/0164789 A1   Jun. 18, 2015

Related U.S. Application Data

(63) Continuation of application No. 14/521,002, filed on Oct. 22, 2014, and a continuation-in-part of application No. PCT/US2013/046443, filed on Jun. 18, 2013, said application No. 14/521,002 is a continuation-in-part of application No. PCT/US2013/023309, filed on Jan. 25, 2013, and a continuation-in-part of application No. 13/843,362, filed on Mar. 15, 2013, which is a continuation-in-part of application No. 13/684,002, filed on Nov. 21, 2012, now Pat. No. 8,633,178, said application No. PCT/US2013/023309 is a continuation-in-part of application No. 13/684,002, filed on Nov. 21, 2012, now Pat. No. 8,633,178.

(60) Provisional application No. 61/932,140, filed on Jan. 27, 2014, provisional application No. 61/894,411, filed on Oct. 22, 2013, provisional application No. 61/745,313, filed on Dec. 21, 2012, provisional application No. 61/661,302, filed on Jun. 18, 2012, provisional application No. 61/662,265, filed on Jun. 20, 2012.

(51) Int. Cl.
*A61K 9/00* (2006.01)
*A61K 31/565* (2006.01)
*A61K 9/48* (2006.01)
*A61K 47/14* (2006.01)

(52) U.S. Cl.
CPC ............ *A61K 9/0036* (2013.01); *A61K 9/4858* (2013.01); *A61K 31/565* (2013.01); *A61K 47/14* (2013.01)

(58) Field of Classification Search
CPC .......................... A61K 9/0036; A61K 31/565
See application file for complete search history.

(56) References Cited

U.S. PATENT DOCUMENTS

| | | |
|---|---|---|
| 1,967,351 A | 1/1934 | Doisy |
| 2,232,438 A | 2/1941 | Butenandt |
| 2,379,832 A | 7/1945 | Serini et al. |
| 2,649,399 A | 8/1953 | Beall et al. |
| 3,198,707 A | 8/1965 | Nomine et al. |
| 3,478,070 A | 11/1969 | Stein et al. |
| 3,526,648 A | 9/1970 | Bertin et al. |
| 3,710,795 A | 1/1973 | Higuchi et al. |
| 3,729,560 A | 4/1973 | Hagerman |
| 3,729,566 A | 4/1973 | Ericsson et al. |
| 3,755,573 A | 8/1973 | Berman |
| 3,755,575 A | 8/1973 | Lerner |
| 3,903,880 A | 9/1975 | Higuchi et al. |
| 3,916,898 A | 11/1975 | Robinson |
| 3,916,899 A | 11/1975 | Theeuwes et al. |
| 3,921,636 A | 11/1975 | Zaffaroni |
| 3,923,997 A | 12/1975 | Meuly |
| 3,948,254 A | 4/1976 | Zaffaroni |
| 3,971,367 A | 7/1976 | Zaffaroni |
| 3,977,404 A | 8/1976 | Theeuwes |
| 3,993,072 A | 11/1976 | Zaffaroni |
| 4,008,719 A | 2/1977 | Theeuwes et al. |
| 4,012,496 A | 3/1977 | Schopflin et al. |
| 4,014,334 A | 3/1977 | Theeuwes et al. |
| 4,014,987 A | 3/1977 | Heller et al. |
| 4,016,251 A | 4/1977 | Higuchi et al. |
| 4,071,623 A | 1/1978 | van der Vies |
| 4,093,709 A | 6/1978 | Choi et al. |
| 4,154,820 A | 5/1979 | Simoons |
| 4,155,991 A | 5/1979 | Schopflin et al. |
| 4,196,188 A | 4/1980 | Besins |
| 4,215,691 A | 8/1980 | Wong |

(Continued)

FOREIGN PATENT DOCUMENTS

| | | |
|---|---|---|
| BR | 11001367-9 A2 | 7/2012 |
| CN | 102258455 A | 11/2011 |

(Continued)

OTHER PUBLICATIONS

US 6,214,374, 4/2001, Schmirler et al. (withdrawn).
Abbas et al., Regression of endometrial implants treated with vitamin $D_3$ in a rat model of endometriosis, European J of Pharma, 715 (2013) 72-75, Elsevier.
Abitec, CapmulMCM, EP, Technical Data Sheet, version 10, 2014, Columbus, OH.
Abitec, CapmulMCM, NF, Technical Data Sheet, version 6, 2014, Columbus, OH.
Abitec, CapmulMCM, Saftey Data Sheet, 2011, Janesville, WI.
Abitec, CapmulMCM, Technical Data Sheet, version 17, 2014, Columbus, OH.
Abitec, CapmulPG8, CAS No. 31565-12-5, version 11, 2006, Columbus, OH.
Abitec, Excipients for the Pharmaceutical Industry—Regulatory and Product Information, 2013, 2 pages.

(Continued)

*Primary Examiner* — Dennis J Parad
(74) *Attorney, Agent, or Firm* — Kilpatrick Townsend & Stockton LLP

(57) ABSTRACT

According to various embodiments of this disclosure, pharmaceutical compositions comprising solubilized estradiol are provided. In various embodiments, such compositions are encapsulated in soft capsules which may be vaginally inserted for the treatment of vulvovaginal atrophy.

21 Claims, 7 Drawing Sheets

(56) References Cited

U.S. PATENT DOCUMENTS

| | | |
|---|---|---|
| 4,237,885 A | 12/1980 | Wong et al. |
| 4,310,510 A | 1/1982 | Sherman et al. |
| 4,327,725 A | 5/1982 | Cortese et al. |
| 4,372,951 A | 2/1983 | Vorys |
| 4,384,096 A | 5/1983 | Sonnabend |
| 4,393,871 A | 7/1983 | Vorhauer et al. |
| 4,402,695 A | 9/1983 | Wong |
| 4,423,151 A | 12/1983 | Baranczuk |
| 4,449,980 A | 5/1984 | Millar et al. |
| 4,610,687 A | 9/1986 | Fogwell |
| 4,629,449 A | 12/1986 | Wong |
| 4,732,763 A | 3/1988 | Beck et al. |
| 4,738,957 A | 4/1988 | Laurent et al. |
| 4,756,907 A | 7/1988 | Beck et al. |
| 4,762,717 A | 8/1988 | Crowley, Jr. |
| 4,788,062 A | 11/1988 | Gale et al. |
| 4,816,257 A | 3/1989 | Buster et al. |
| 4,822,616 A | 4/1989 | Zimmermann et al. |
| 4,865,848 A | 9/1989 | Cheng et al. |
| 4,900,734 A | 2/1990 | Maxson et al. |
| 4,906,475 A | 3/1990 | Kim |
| 4,942,158 A | 7/1990 | Sarpotdar et al. |
| 4,961,931 A | 10/1990 | Wong |
| 5,030,629 A | 7/1991 | Rajadhyaksha |
| 5,064,654 A | 11/1991 | Berner et al. |
| 5,108,995 A | 4/1992 | Casper |
| 5,128,138 A | 7/1992 | Blank |
| 5,130,137 A | 7/1992 | Crowley, Jr. |
| 5,140,021 A | 8/1992 | Maxson et al. |
| 5,211,952 A | 5/1993 | Spicer et al. |
| 5,252,334 A | 10/1993 | Chiang et al. |
| 5,280,023 A | 1/1994 | Ehrlich et al. |
| 5,288,496 A | 2/1994 | Lewis |
| 5,340,584 A | 8/1994 | Spicer et al. |
| 5,340,585 A | 8/1994 | Pike et al. |
| 5,340,586 A | 8/1994 | Pike et al. |
| 5,362,497 A | 11/1994 | Yamada et al. |
| 5,382,573 A | 1/1995 | Casper |
| 5,393,528 A | 2/1995 | Staab |
| 5,393,529 A | 2/1995 | Hoffmann et al. |
| 5,419,910 A | 5/1995 | Lewis |
| 5,468,736 A | 11/1995 | Hodgen |
| 5,474,783 A | 12/1995 | Miranda et al. |
| 5,480,776 A | 1/1996 | Dullien |
| 5,514,673 A | 5/1996 | Heckenmueller et al. |
| 5,516,528 A | 5/1996 | Hughes et al. |
| 5,527,534 A | 6/1996 | Myhling |
| 5,529,782 A | 6/1996 | Staab |
| 5,538,736 A | 7/1996 | Barth et al. |
| 5,543,150 A | 8/1996 | Bologna et al. |
| 5,547,948 A | 8/1996 | Barcomb |
| 5,556,635 A | 9/1996 | Grognet et al. |
| 5,565,199 A | 10/1996 | Page et al. |
| 5,567,831 A | 10/1996 | Li |
| 5,569,652 A | 10/1996 | Beier et al. |
| 5,580,572 A | 12/1996 | Mikler et al. |
| 5,582,592 A | 12/1996 | Kendrick |
| 5,585,370 A | 12/1996 | Casper |
| 5,595,759 A | 1/1997 | Wright et al. |
| 5,595,970 A | 1/1997 | Garfield et al. |
| 5,605,702 A | 2/1997 | Teillaud et al. |
| 5,607,691 A | 3/1997 | Hale et al. |
| 5,607,693 A | 3/1997 | Bonte et al. |
| 5,609,617 A | 3/1997 | Shealy et al. |
| 5,620,705 A | 4/1997 | Dong et al. |
| 5,626,866 A | 5/1997 | Ebert et al. |
| 5,629,021 A | 5/1997 | Wright |
| 5,633,011 A | 5/1997 | Dong et al. |
| 5,633,242 A | 5/1997 | Oettel et al. |
| 5,639,743 A | 6/1997 | Kaswan et al. |
| 5,653,983 A | 8/1997 | Meybeck et al. |
| 5,656,286 A | 8/1997 | Miranda et al. |
| 5,660,839 A | 8/1997 | Allec et al. |
| 5,662,927 A | 9/1997 | Ehrlich et al. |
| 5,663,160 A | 9/1997 | Meybeck et al. |
| 5,676,968 A | 10/1997 | Lipp et al. |
| 5,677,292 A | 10/1997 | Li et al. |
| 5,686,097 A | 11/1997 | Taskovich et al. |
| 5,693,335 A | 12/1997 | Xia et al. |
| 5,694,947 A | 12/1997 | Lehtinen et al. |
| 5,700,480 A | 12/1997 | Hille et al. |
| 5,709,844 A | 1/1998 | Arbeit et al. |
| 5,719,197 A | 2/1998 | Kanios et al. |
| 5,735,801 A | 4/1998 | Caillouette |
| 5,739,176 A | 4/1998 | Dunn et al. |
| 5,744,463 A | 4/1998 | Bair |
| 5,747,058 A | 5/1998 | Tipton et al. |
| 5,762,614 A | 6/1998 | Caillouette |
| 5,770,176 A | 6/1998 | Nargessi |
| 5,770,219 A | 6/1998 | Chiang et al. |
| 5,770,220 A | 6/1998 | Meconi et al. |
| 5,770,227 A | 6/1998 | Dong et al. |
| 5,776,495 A | 7/1998 | Duclos et al. |
| 5,780,044 A | 7/1998 | Yewey et al. |
| 5,780,050 A | 7/1998 | Jain et al. |
| 5,788,980 A | 8/1998 | Nabahi |
| 5,788,984 A | 8/1998 | Guenther et al. |
| 5,789,442 A | 8/1998 | Garfield et al. |
| 5,811,416 A | 9/1998 | Chwalisz et al. |
| 5,811,547 A | 9/1998 | Nakamichi et al. |
| 5,814,329 A | 9/1998 | Shah |
| 5,820,878 A | 10/1998 | Hirano et al. |
| 5,827,200 A | 10/1998 | Caillouette |
| 5,840,327 A | 11/1998 | Gale et al. |
| 5,843,468 A | 12/1998 | Burkoth et al. |
| 5,843,979 A | 12/1998 | Wille et al. |
| 5,858,394 A | 1/1999 | Lipp et al. |
| 5,863,552 A | 1/1999 | Yue |
| 5,866,603 A | 2/1999 | Li et al. |
| 5,882,676 A | 3/1999 | Lee et al. |
| 5,885,612 A | 3/1999 | Meconi et al. |
| 5,888,533 A | 3/1999 | Dunn |
| 5,891,462 A | 4/1999 | Carrara |
| 5,891,868 A | 4/1999 | Cummings et al. |
| 5,898,038 A | 4/1999 | Yallampalli et al. |
| 5,902,603 A | 5/1999 | Chen et al. |
| 5,904,931 A | 5/1999 | Lipp et al. |
| 5,906,830 A | 5/1999 | Farinas et al. |
| 5,912,010 A | 6/1999 | Wille et al. |
| 5,916,176 A | 6/1999 | Caillouette |
| RE36,247 E | 7/1999 | Plunkett et al. |
| 5,919,477 A | 7/1999 | Bevan et al. |
| 5,922,349 A | 7/1999 | Elliesen et al. |
| 5,928,666 A | 7/1999 | Farinas et al. |
| 5,942,243 A | 8/1999 | Shah |
| 5,942,531 A | 8/1999 | Diaz et al. |
| 5,952,000 A | 9/1999 | Venkateshwaran et al. |
| 5,958,446 A | 9/1999 | Miranda et al. |
| 5,962,445 A | 10/1999 | Stewart |
| 5,968,919 A | 10/1999 | Samour et al. |
| 5,972,372 A | 10/1999 | Saleh et al. |
| 5,985,311 A | 11/1999 | Cordes et al. |
| 5,985,850 A | 11/1999 | Falk et al. |
| 5,985,861 A | 11/1999 | Levine et al. |
| 5,989,568 A | 11/1999 | Breton et al. |
| 5,993,856 A | 11/1999 | Ragavan et al. |
| 6,001,846 A | 12/1999 | Edwards et al. |
| 6,007,835 A | 12/1999 | Bon Lapillonne et al. |
| 6,010,715 A | 1/2000 | Wick et al. |
| 6,013,276 A | 1/2000 | Math et al. |
| 6,022,562 A | 2/2000 | Autant et al. |
| 6,024,974 A | 2/2000 | Li |
| 6,024,976 A | 2/2000 | Miranda et al. |
| 6,028,057 A | 2/2000 | Burns |
| 6,030,948 A | 2/2000 | Mann |
| 6,039,968 A | 3/2000 | Nabahi |
| 6,040,340 A | 3/2000 | Chwalisz et al. |
| 6,056,972 A | 5/2000 | Hermsmeyer |
| 6,060,077 A | 5/2000 | Meignant |
| 6,068,853 A | 5/2000 | Giannos et al. |
| 6,074,625 A | 6/2000 | Hawthorne et al. |
| 6,077,531 A | 6/2000 | Salin-Drouin |
| 6,080,118 A | 6/2000 | Blythe |
| 6,083,178 A | 7/2000 | Caillouette |

(56) References Cited

U.S. PATENT DOCUMENTS

| | | |
|---|---|---|
| 6,086,916 A | 7/2000 | Agnus et al. |
| 6,087,352 A | 7/2000 | Trout |
| 6,090,404 A | 7/2000 | Meconi et al. |
| 6,096,338 A | 8/2000 | Lacy et al. |
| 6,106,848 A | 8/2000 | Preuilh et al. |
| 6,117,446 A | 9/2000 | Place |
| 6,117,450 A | 9/2000 | Dittgen et al. |
| 6,124,362 A | 9/2000 | Bradbury et al. |
| 6,133,251 A | 10/2000 | Dittgen et al. |
| 6,133,320 A | 10/2000 | Yallampalli et al. |
| 6,139,868 A | 10/2000 | Hoffmann |
| 6,139,873 A | 10/2000 | Hughes, Jr. et al. |
| 6,149,935 A | 11/2000 | Chiang et al. |
| 6,153,216 A | 11/2000 | Cordes et al. |
| 6,165,491 A | 12/2000 | Grasset et al. |
| 6,165,975 A | 12/2000 | Adams et al. |
| 6,187,323 B1 | 2/2001 | Aiache et al. |
| 6,187,339 B1 | 2/2001 | de Haan et al. |
| 6,190,331 B1 | 2/2001 | Caillouette |
| 6,201,072 B1 | 3/2001 | Rathi et al. |
| 6,217,886 B1 | 4/2001 | Onyueksel et al. |
| 6,225,297 B1 | 5/2001 | Stockemann et al. |
| 6,227,202 B1 | 5/2001 | Matapurkar |
| 6,228,383 B1 | 5/2001 | Hansen et al. |
| 6,228,852 B1 | 5/2001 | Shaak |
| 6,242,509 B1 | 6/2001 | Berger et al. |
| 6,245,811 B1 | 6/2001 | Horrobin et al. |
| 6,262,115 B1 | 7/2001 | Guittard et al. |
| 6,267,984 B1 | 7/2001 | Beste et al. |
| 6,274,165 B1 | 8/2001 | Meconi et al. |
| 6,277,418 B1 | 8/2001 | Marakverich et al. |
| 6,283,927 B1 | 9/2001 | Caillouette |
| 6,287,588 B1 | 9/2001 | Shih et al. |
| 6,287,693 B1 | 9/2001 | Savoir et al. |
| 6,294,188 B1 | 9/2001 | Ragavan et al. |
| 6,294,192 B1 | 9/2001 | Patel et al. |
| 6,294,550 B1 | 9/2001 | Place et al. |
| 6,299,900 B1 | 10/2001 | Reed et al. |
| 6,303,132 B1 | 10/2001 | Nelson |
| 6,303,588 B1 | 10/2001 | Danielov |
| 6,306,841 B1 | 10/2001 | Place et al. |
| 6,306,914 B1 | 10/2001 | de Ziegler et al. |
| 6,309,669 B1 | 10/2001 | Setterstrom et al. |
| 6,309,848 B1 | 10/2001 | Howett et al. |
| 6,312,703 B1 | 11/2001 | Orthoefer |
| 6,328,987 B1 | 12/2001 | Marini |
| 6,342,491 B1 | 1/2002 | Dey et al. |
| 6,344,211 B1 | 2/2002 | Hille |
| 6,372,209 B1 | 4/2002 | Chrisope |
| 6,372,245 B1 | 4/2002 | Bowman et al. |
| 6,372,246 B1 | 4/2002 | Wei et al. |
| 6,387,390 B1 | 5/2002 | Deaver et al. |
| 6,402,705 B1 | 6/2002 | Caillouette |
| 6,416,778 B1 | 7/2002 | Ragavan et al. |
| 6,420,352 B1 | 7/2002 | Knowles |
| 6,423,039 B1 | 7/2002 | Rathbone et al. |
| 6,423,683 B1 | 7/2002 | Heaton et al. |
| 6,432,438 B1 | 8/2002 | Shukla |
| 6,436,633 B1 | 8/2002 | Kreider et al. |
| 6,440,454 B1 | 8/2002 | Santoro et al. |
| 6,444,224 B1 | 9/2002 | Rathbone et al. |
| 6,444,234 B1 | 9/2002 | Kirby et al. |
| 6,451,300 B1 | 9/2002 | Dunlop et al. |
| 6,451,339 B2 | 9/2002 | Patel et al. |
| 6,451,779 B1 | 9/2002 | Hesch |
| 6,455,246 B1 | 9/2002 | Howett et al. |
| 6,455,517 B1 | 9/2002 | Tanabe et al. |
| 6,465,004 B1 | 10/2002 | Rossi Montero et al. |
| 6,465,005 B1 | 10/2002 | Biali et al. |
| 6,465,006 B1 | 10/2002 | Zhang et al. |
| 6,468,526 B2 | 10/2002 | Chrisope |
| 6,469,016 B1 | 10/2002 | Place et al. |
| 6,472,434 B1 | 10/2002 | Place et al. |
| 6,479,232 B1 | 11/2002 | Howett et al. |
| 6,495,160 B2 | 12/2002 | Esposito et al. |
| 6,500,814 B1 | 12/2002 | Hesch |
| 6,503,896 B1 | 1/2003 | Tanabe et al. |
| 6,511,969 B1 | 1/2003 | Hermsmeyer |
| 6,521,250 B2 | 2/2003 | Meconi et al. |
| 6,526,980 B1 | 3/2003 | Tracy et al. |
| 6,528,094 B1 | 3/2003 | Savoir et al. |
| 6,531,149 B1 | 3/2003 | Kirstgen et al. |
| 6,537,580 B1 | 3/2003 | Savoir et al. |
| 6,538,039 B2 | 3/2003 | Laurent |
| 6,544,196 B2 | 4/2003 | Caillouette |
| 6,544,553 B1 | 4/2003 | Hsia et al. |
| 6,548,053 B1 | 4/2003 | Stewart et al. |
| 6,548,491 B2 | 4/2003 | Tanabe et al. |
| 6,551,611 B2 | 4/2003 | Elliesen et al. |
| 6,555,131 B1 | 4/2003 | Wolff et al. |
| 6,562,367 B1 | 5/2003 | Wolff et al. |
| 6,562,370 B2 | 5/2003 | Luo et al. |
| 6,562,790 B2 | 5/2003 | Chein |
| 6,569,463 B2 | 5/2003 | Patel et al. |
| 6,583,129 B1 | 6/2003 | Mazer et al. |
| 6,586,006 B2 | 7/2003 | Roser et al. |
| 6,589,549 B2 | 7/2003 | Shih et al. |
| 6,593,317 B1 | 7/2003 | de Ziegler et al. |
| 6,599,519 B1 | 7/2003 | Seo et al. |
| 6,610,652 B2 | 8/2003 | Adams et al. |
| 6,610,670 B2 | 8/2003 | Backensfeld et al. |
| 6,610,674 B1 | 8/2003 | Schreiber |
| 6,635,274 B1 | 10/2003 | Masiz et al. |
| 6,638,528 B1 | 10/2003 | Kanios |
| 6,638,536 B2 | 10/2003 | Savoir et al. |
| 6,645,528 B1 | 11/2003 | Straub et al. |
| 6,649,155 B1 | 11/2003 | Dunlop et al. |
| 6,653,298 B2 | 11/2003 | Potter et al. |
| 6,656,929 B1 | 12/2003 | Agnus et al. |
| 6,660,726 B2 | 12/2003 | Hill et al. |
| 6,663,608 B2 | 12/2003 | Rathbone et al. |
| 6,663,895 B2 | 12/2003 | Savoir et al. |
| 6,682,757 B1 | 1/2004 | Wright |
| 6,692,763 B1 | 2/2004 | Cummings et al. |
| 6,708,822 B1 | 3/2004 | Muni |
| 6,720,001 B2 | 4/2004 | Chen et al. |
| 6,737,081 B2 | 5/2004 | Savoir et al. |
| 6,740,333 B2 | 5/2004 | Beckett et al. |
| 6,743,448 B2 | 6/2004 | Kryger |
| 6,743,815 B2 | 6/2004 | Huebner et al. |
| 6,747,018 B2 | 6/2004 | Tanabe et al. |
| 6,750,291 B2 | 6/2004 | Kim et al. |
| 6,756,208 B2 | 6/2004 | Griffin et al. |
| 6,776,164 B2 | 8/2004 | Bunt et al. |
| 6,787,152 B2 | 9/2004 | Kirby et al. |
| 6,805,877 B2 | 10/2004 | Massara et al. |
| 6,809,085 B1 | 10/2004 | Elson et al. |
| 6,818,226 B2 | 11/2004 | Reed et al. |
| 6,821,524 B2 | 11/2004 | Marini |
| 6,841,716 B1 | 1/2005 | Tsutsumi |
| 6,844,334 B2 | 1/2005 | Hill et al. |
| 6,855,703 B1 | 2/2005 | Hill et al. |
| 6,860,859 B2 | 3/2005 | Mehrotra et al. |
| 6,866,865 B2 | 3/2005 | Hsia et al. |
| 6,869,969 B2 | 3/2005 | Heubner et al. |
| 6,878,518 B2 | 4/2005 | Whitehead |
| 6,901,278 B1 | 5/2005 | Notelovitz |
| 6,905,705 B2 | 6/2005 | Palm et al. |
| 6,911,211 B2 | 6/2005 | Eini et al. |
| 6,911,438 B2 | 6/2005 | Wright |
| 6,923,988 B2 | 8/2005 | Patel et al. |
| 6,924,274 B2 | 8/2005 | Lardy et al. |
| 6,932,983 B1 | 8/2005 | Straub et al. |
| 6,939,558 B2 | 9/2005 | Massara et al. |
| 6,943,021 B2 | 9/2005 | Klausner et al. |
| 6,958,327 B1 | 10/2005 | Hillisch et al. |
| 6,960,337 B2 | 11/2005 | Daniels et al. |
| 6,962,691 B1 | 11/2005 | Lulla et al. |
| 6,962,908 B2 | 11/2005 | Aloba et al. |
| 6,967,194 B1 | 11/2005 | Matsuo et al. |
| 6,974,569 B2 | 12/2005 | Dunlop et al. |
| 6,977,250 B2 | 12/2005 | Rodriguez |
| 6,978,945 B2 | 12/2005 | Wong et al. |
| 6,995,149 B1 | 2/2006 | Endrikat et al. |

(56) References Cited

U.S. PATENT DOCUMENTS

| | | |
|---|---|---|
| 7,004,321 B1 | 2/2006 | Palm et al. |
| 7,005,429 B2 | 2/2006 | Dey et al. |
| 7,011,846 B2 | 3/2006 | Shojaei et al. |
| 7,018,992 B2 | 3/2006 | Koch et al. |
| 7,030,104 B2 | 4/2006 | Gray et al. |
| 7,030,157 B2 | 4/2006 | Ke et al. |
| RE39,104 E | 5/2006 | Duclos et al. |
| 7,074,779 B2 | 7/2006 | Sui et al. |
| 7,083,590 B1 | 8/2006 | Bunt et al. |
| 7,091,213 B2 | 8/2006 | Metcalf, III et al. |
| 7,094,228 B2 | 8/2006 | Zhang et al. |
| 7,097,853 B1 | 8/2006 | Garbe et al. |
| 7,101,342 B1 | 9/2006 | Caillouette |
| 7,105,573 B2 | 9/2006 | Krajcik et al. |
| 7,135,190 B2 | 11/2006 | Piao et al. |
| 7,153,522 B1 | 12/2006 | Ikeura et al. |
| 7,163,681 B2 | 1/2007 | Giles-Komar et al. |
| 7,163,699 B2 | 1/2007 | Besse |
| 7,175,850 B2 | 2/2007 | Cevc |
| 7,179,799 B2 | 2/2007 | Hill et al. |
| 7,196,074 B2 | 3/2007 | Blye et al. |
| 7,198,800 B1 | 4/2007 | Ko |
| 7,198,801 B2 | 4/2007 | Carrara et al. |
| 7,226,910 B2 | 6/2007 | Wilson et al. |
| 7,247,625 B2 | 7/2007 | Zhang et al. |
| 7,250,446 B2 | 7/2007 | Sangita et al. |
| 7,267,829 B2 | 9/2007 | Kirby et al. |
| 7,300,926 B2 | 11/2007 | Prokai et al. |
| 7,303,763 B2 | 12/2007 | Ho |
| 7,317,037 B2 | 1/2008 | Fensome et al. |
| 7,329,654 B2 | 2/2008 | Kanojia et al. |
| 7,335,650 B2 | 2/2008 | Potter et al. |
| 7,374,779 B2 | 5/2008 | Chen et al. |
| 7,378,404 B2 | 5/2008 | Peters et al. |
| 7,381,427 B2 | 6/2008 | Ancira et al. |
| 7,387,789 B2 | 6/2008 | Klose et al. |
| 7,388,006 B2 | 6/2008 | Schmees et al. |
| 7,414,043 B2 | 8/2008 | Kosemund et al. |
| 7,427,413 B2 | 9/2008 | Savoir et al. |
| 7,427,609 B2 | 9/2008 | Leonard |
| 7,429,576 B2 | 9/2008 | Labrie |
| 7,431,941 B2 | 10/2008 | Besins et al. |
| 7,456,159 B2 | 11/2008 | Houze et al. |
| 7,459,445 B2 | 12/2008 | Hill et al. |
| 7,465,587 B2 | 12/2008 | Imrich |
| 7,470,433 B2 | 12/2008 | Carrara et al. |
| 7,485,666 B2 | 2/2009 | Villaneuva et al. |
| 7,497,855 B2 | 3/2009 | Ausiello et al. |
| 7,498,303 B2 | 3/2009 | Arnold et al. |
| 7,534,765 B2 | 5/2009 | Gregg et al. |
| 7,534,780 B2 | 5/2009 | Wyrwa et al. |
| 7,550,142 B2 | 6/2009 | Giles-Komar et al. |
| 7,563,565 B1 | 7/2009 | Matsuo et al. |
| 7,569,274 B2 | 8/2009 | Besse et al. |
| 7,572,779 B2 | 8/2009 | Aloba et al. |
| 7,572,780 B2 | 8/2009 | Hermsmeyer |
| 7,589,082 B2 | 9/2009 | Savoir et al. |
| 7,671,027 B2 | 3/2010 | Loumaye |
| 7,674,783 B2 | 3/2010 | Hermsmeyer |
| 7,687,281 B2 | 3/2010 | Roth et al. |
| 7,687,485 B2 | 3/2010 | Levinson et al. |
| 7,694,683 B2 | 4/2010 | Callister et al. |
| 7,704,983 B1 | 4/2010 | Hodgen et al. |
| 7,727,720 B2 | 6/2010 | Dhallan |
| 7,732,408 B2 | 6/2010 | Josephson et al. |
| 7,749,989 B2 | 7/2010 | Hill et al. |
| 7,767,656 B2 | 8/2010 | Shoichet et al. |
| 7,799,769 B2 | 9/2010 | White et al. |
| 7,815,936 B2 | 10/2010 | Hasenzahl et al. |
| 7,815,949 B2 | 10/2010 | Cohen |
| 7,829,115 B2 | 11/2010 | Besins et al. |
| 7,829,116 B2 | 11/2010 | Griswold et al. |
| RE42,012 E | 12/2010 | Deaver et al. |
| 7,850,992 B2 | 12/2010 | Kim et al. |
| 7,854,753 B2 | 12/2010 | Kraft et al. |
| 7,858,607 B2 | 12/2010 | Mamchur |
| RE42,072 E | 1/2011 | Deaver et al. |
| 7,862,552 B2 | 1/2011 | McIntyre et al. |
| 7,867,990 B2 | 1/2011 | Schultz et al. |
| 7,871,643 B2 | 1/2011 | Lizio et al. |
| 7,879,830 B2 | 2/2011 | Wiley |
| 7,884,093 B2 | 2/2011 | Creasy et al. |
| 7,925,519 B2 | 4/2011 | Greene |
| 7,939,104 B2 | 5/2011 | Barbera et al. |
| 7,943,602 B2 | 5/2011 | Bunschoten et al. |
| 7,943,604 B2 | 5/2011 | Coelingh Bennink et al. |
| 7,945,459 B2 | 5/2011 | Grace et al. |
| 7,960,368 B2 | 6/2011 | Nickisch et al. |
| 7,989,436 B2 | 8/2011 | Hill et al. |
| 7,989,487 B2 | 8/2011 | Welsh et al. |
| 8,022,053 B2 | 9/2011 | Mueller et al. |
| 8,048,017 B2 | 11/2011 | Xu |
| 8,048,869 B2 | 11/2011 | Bunschoten et al. |
| 8,063,030 B2 | 11/2011 | Ellman |
| 8,071,576 B2 | 12/2011 | Coelingh Bennink et al. |
| 8,071,729 B2 | 12/2011 | Giles-Komar et al. |
| 8,075,916 B2 | 12/2011 | Song et al. |
| 8,075,917 B2 | 12/2011 | Chung et al. |
| 8,076,317 B2 | 12/2011 | Kulmann |
| 8,076,319 B2 | 12/2011 | Leonard |
| 8,080,553 B2 | 12/2011 | Keith et al. |
| 8,088,605 B2 | 1/2012 | Beudet et al. |
| 8,096,940 B2 | 1/2012 | Josephson et al. |
| 8,101,209 B2 | 1/2012 | Legrand et al. |
| 8,101,773 B2 | 1/2012 | Smith et al. |
| 8,114,152 B2 | 2/2012 | Furst |
| 8,114,434 B2 | 2/2012 | Sasaki et al. |
| 8,114,442 B2 | 2/2012 | Tucker et al. |
| 8,119,741 B2 | 2/2012 | Pavlin |
| 8,121,886 B2 | 2/2012 | Azar |
| 8,124,118 B2 | 2/2012 | Lennernaes et al. |
| 8,124,595 B2 | 2/2012 | Boissonneault |
| 8,147,561 B2 | 4/2012 | Binmoeller |
| 8,148,546 B2 | 4/2012 | Schuster et al. |
| 8,158,613 B2 | 4/2012 | Staniforth et al. |
| 8,158,614 B2 | 4/2012 | Lambert et al. |
| 8,163,722 B2 | 4/2012 | Savoir et al. |
| 8,177,449 B2 | 5/2012 | Watkinson et al. |
| 8,182,833 B2 | 5/2012 | Hermsmeyer |
| 8,187,615 B2 | 5/2012 | Friedman |
| 8,187,640 B2 | 5/2012 | Dunn |
| 8,195,403 B2 | 6/2012 | Ishikawa et al. |
| 8,202,736 B2 | 6/2012 | Mousa et al. |
| 8,217,024 B2 | 7/2012 | Ahmed et al. |
| 8,221,785 B2 | 7/2012 | Chien |
| 8,222,008 B2 | 7/2012 | Thoene |
| 8,222,237 B2 | 7/2012 | Nickisch et al. |
| 8,227,454 B2 | 7/2012 | Hill et al. |
| 8,227,509 B2 | 7/2012 | Castro et al. |
| 8,241,664 B2 | 8/2012 | Dudley et al. |
| 8,247,393 B2 | 8/2012 | Ahmed et al. |
| 8,257,724 B2 | 9/2012 | Cromack et al. |
| 8,257,725 B2 | 9/2012 | Cromack et al. |
| 8,268,352 B2 | 9/2012 | Vaya et al. |
| 8,268,806 B2 | 9/2012 | Labrie |
| 8,268,878 B2 | 9/2012 | Armer et al. |
| 8,273,730 B2 | 9/2012 | Fernandez et al. |
| 8,287,888 B2 | 10/2012 | Song et al. |
| 8,288,366 B2 | 10/2012 | Chochinov et al. |
| 8,318,898 B2 | 11/2012 | Fasel et al. |
| 8,324,193 B2 | 12/2012 | Lee Sepsick et al. |
| 8,329,680 B2 | 12/2012 | Evans et al. |
| 8,337,814 B2 | 12/2012 | Osbakken et al. |
| 8,344,007 B2 | 1/2013 | Tang et al. |
| 8,349,820 B2 | 1/2013 | Zeun et al. |
| 8,353,863 B2 | 1/2013 | Imran |
| 8,357,723 B2 | 1/2013 | Satyam |
| 8,361,995 B2 | 1/2013 | Schramm |
| 8,362,091 B2 | 1/2013 | Tamarkin et al. |
| 8,372,424 B2 | 2/2013 | Berry et al. |
| 8,372,806 B2 | 2/2013 | Boehler et al. |
| 8,377,482 B2 | 2/2013 | Laurie et al. |
| 8,377,994 B2 | 2/2013 | Gray et al. |
| 8,394,759 B2 | 3/2013 | Barathur et al. |

(56) References Cited

U.S. PATENT DOCUMENTS

| | | | |
|---|---|---|---|
| 8,415,332 B2 | 4/2013 | Diliberti et al. |
| 8,420,111 B2 | 4/2013 | Hermsmeyer |
| 8,435,561 B2 | 5/2013 | Besins et al. |
| 8,435,972 B2 | 5/2013 | Stein et al. |
| 8,449,879 B2 | 5/2013 | Laurent Applegate et al. |
| 8,450,108 B2 | 5/2013 | Boyce |
| 8,454,945 B2 | 6/2013 | McCook et al. |
| 8,455,468 B2 | 6/2013 | Hoffman et al. |
| 8,461,138 B2 | 6/2013 | Boissonneault |
| 8,476,252 B2 | 7/2013 | Achleitner et al. |
| 8,481,488 B2 | 7/2013 | Carter |
| 8,486,374 B2 | 7/2013 | Tamarkin et al. |
| 8,486,442 B2 | 7/2013 | Matsushita et al. |
| 8,492,368 B2 | 7/2013 | Vanlandingham et al. |
| 8,507,467 B2 | 8/2013 | Matsui et al. |
| 8,512,693 B2 | 8/2013 | Capito et al. |
| 8,512,754 B2 | 8/2013 | Needham |
| 8,518,376 B2 | 8/2013 | Tamarkin et al. |
| 8,536,159 B2 | 9/2013 | Li et al. |
| 8,540,967 B2 | 9/2013 | Trivedievan et al. |
| 8,541,400 B2 | 9/2013 | Johnsson et al. |
| 8,551,462 B2 | 10/2013 | Goldstein et al. |
| 8,557,281 B2 | 10/2013 | Halliday et al. |
| 8,568,374 B2 | 10/2013 | De Graaff et al. |
| 8,591,951 B2 | 11/2013 | Kohn et al. |
| 8,613,951 B2 | 12/2013 | Zale et al. |
| 8,633,178 B2 * | 1/2014 | Bernick et al. ............... 514/169 |
| 8,633,180 B2 | 1/2014 | Li et al. |
| 8,636,787 B2 | 1/2014 | Sabaria |
| 8,636,982 B2 | 1/2014 | Tamarkin et al. |
| 8,653,129 B2 | 2/2014 | Fein et al. |
| 8,658,627 B2 | 2/2014 | Voskuhl |
| 8,658,628 B2 | 2/2014 | Baucom |
| 8,663,681 B2 | 3/2014 | Ahmed et al. |
| 8,663,692 B1 | 3/2014 | Mueller et al. |
| 8,663,703 B2 | 3/2014 | Lerner et al. |
| 8,664,207 B2 | 3/2014 | Li et al. |
| 8,669,293 B2 | 3/2014 | Levy et al. |
| 8,679,552 B2 | 3/2014 | Guthery |
| 8,694,358 B2 | 4/2014 | Tryfon |
| 8,697,127 B2 | 4/2014 | Sah |
| 8,697,710 B2 | 4/2014 | Li et al. |
| 8,703,105 B2 | 4/2014 | Tamarkin et al. |
| 8,709,385 B2 | 4/2014 | Tamarkin et al. |
| 8,709,451 B2 | 4/2014 | Nam et al. |
| 8,715,735 B2 | 5/2014 | Funke et al. |
| 8,721,331 B2 | 5/2014 | Raghuprasad |
| 8,722,021 B2 | 5/2014 | Friedman et al. |
| 8,734,846 B2 | 5/2014 | Ali et al. |
| 8,735,381 B2 | 5/2014 | Podolski |
| 8,741,336 B2 | 6/2014 | Dipierro et al. |
| 8,741,373 B2 | 6/2014 | Bromley et al. |
| 8,753,661 B2 | 6/2014 | Steinmueller Nethl et al. |
| 8,784,882 B2 | 7/2014 | Mattern |
| 8,846,648 B2 * | 9/2014 | Bernick et al. ............... 514/169 |
| 8,846,649 B2 * | 9/2014 | Bernick et al. ............... 514/169 |
| 8,933,059 B2 * | 1/2015 | Bernick et al. ............... 514/169 |
| 8,987,237 B2 * | 3/2015 | Bernick et al. ............... 514/169 |
| 8,987,238 B2 * | 3/2015 | Bernick et al. ............... 514/169 |
| 8,993,548 B2 * | 3/2015 | Bernick et al. ............... 514/169 |
| 8,993,549 B2 * | 3/2015 | Bernick et al. ............... 514/169 |
| 9,006,222 B2 | 4/2015 | Bernick et al. |
| 9,012,434 B2 | 4/2015 | Bernick et al. |
| 2001/0005728 A1 | 6/2001 | Guittard et al. |
| 2001/0009673 A1 | 7/2001 | Lipp et al. |
| 2001/0021816 A1 | 9/2001 | Caillouette |
| 2001/0023261 A1 | 9/2001 | Ryoo et al. |
| 2001/0027189 A1 | 10/2001 | Bennink et al. |
| 2001/0029357 A1 | 10/2001 | Bunt et al. |
| 2001/0031747 A1 | 10/2001 | de Ziegler et al. |
| 2001/0032125 A1 | 10/2001 | Bhan et al. |
| 2001/0034340 A1 | 10/2001 | Pickar |
| 2012/0269878 A2 | 10/2001 | Cantor et al. |
| 2001/0053383 A1 | 12/2001 | Miranda et al. |
| 2001/0056068 A1 | 12/2001 | Chwalisz et al. |
| 2002/0012710 A1 | 1/2002 | Lansky |
| 2002/0026158 A1 | 2/2002 | Rathbone et al. |
| 2002/0028788 A1 | 3/2002 | Bunt et al. |
| 2002/0035070 A1 | 3/2002 | Gardlik et al. |
| 2002/0058648 A1 | 5/2002 | Hammerly |
| 2002/0058926 A1 | 5/2002 | Rathbone et al. |
| 2002/0064541 A1 | 5/2002 | Lapidot et al. |
| 2002/0076441 A1 | 6/2002 | Shih et al. |
| 2002/0102308 A1 | 8/2002 | Wei et al. |
| 2002/0107230 A1 | 8/2002 | Waldon et al. |
| 2002/0114803 A1 | 8/2002 | Deaver et al. |
| 2002/0119174 A1 | 8/2002 | Gardlik et al. |
| 2002/0119198 A1 | 8/2002 | Gao et al. |
| 2002/0132801 A1 | 9/2002 | Heil et al. |
| 2002/0137749 A1 | 9/2002 | Levinson et al. |
| 2002/0142017 A1 | 10/2002 | Simonnet |
| 2002/0151530 A1 | 10/2002 | Leonard et al. |
| 2002/0156394 A1 | 10/2002 | Mehrotra et al. |
| 2002/0169150 A1 | 11/2002 | Pickar |
| 2002/0169205 A1 | 11/2002 | Chwalisz et al. |
| 2002/0173510 A1 | 11/2002 | Levinson et al. |
| 2002/0193356 A1 | 12/2002 | Van Beek et al. |
| 2002/0193758 A1 | 12/2002 | Sandberg |
| 2002/0197286 A1 | 12/2002 | Brandman et al. |
| 2003/0003139 A1 | 1/2003 | Lipp et al. |
| 2003/0004145 A1 | 1/2003 | Leonard |
| 2003/0007994 A1 | 1/2003 | Bunt et al. |
| 2003/0027772 A1 | 2/2003 | Breton |
| 2003/0044453 A1 | 3/2003 | Dittgen et al. |
| 2003/0049307 A1 | 3/2003 | Gyurik |
| 2003/0064097 A1 | 4/2003 | Patel et al. |
| 2003/0064975 A1 | 4/2003 | Koch et al. |
| 2003/0072760 A1 | 4/2003 | Sirbasku |
| 2003/0073248 A1 | 4/2003 | Roth et al. |
| 2003/0073673 A1 | 4/2003 | Hesch |
| 2003/0077297 A1 | 4/2003 | Chen et al. |
| 2003/0078245 A1 | 4/2003 | Bennink et al. |
| 2003/0091620 A1 | 5/2003 | Fikstad et al. |
| 2003/0091640 A1 | 5/2003 | Ramanathan et al. |
| 2003/0092691 A1 | 5/2003 | Besse et al. |
| 2003/0096012 A1 | 5/2003 | Besse et al. |
| 2003/0104048 A1 | 6/2003 | Patel et al. |
| 2003/0109507 A1 | 6/2003 | Franke et al. |
| 2003/0113268 A1 | 6/2003 | Buenafae et al. |
| 2003/0114420 A1 | 6/2003 | Salvati et al. |
| 2003/0114430 A1 | 6/2003 | MacLeod et al. |
| 2003/0124182 A1 | 7/2003 | Shojaei et al. |
| 2003/0124191 A1 | 7/2003 | Besse et al. |
| 2003/0130558 A1 | 7/2003 | Massara et al. |
| 2003/0144258 A1 | 7/2003 | Heil et al. |
| 2003/0157157 A1 | 8/2003 | Luo et al. |
| 2003/0166509 A1 | 9/2003 | Edwards et al. |
| 2003/0170295 A1 | 9/2003 | Kim et al. |
| 2003/0175329 A1 | 9/2003 | Azarnoff et al. |
| 2003/0175333 A1 | 9/2003 | Shefer et al. |
| 2003/0180352 A1 | 9/2003 | Patel et al. |
| 2003/0181353 A1 | 9/2003 | Nyce |
| 2003/0181728 A1 | 9/2003 | Salvati et al. |
| 2003/0191096 A1 | 10/2003 | Leonard et al. |
| 2003/0195177 A1 | 10/2003 | Leonard et al. |
| 2003/0215496 A1 | 11/2003 | Patel et al. |
| 2003/0219402 A1 | 11/2003 | Rutter |
| 2003/0220297 A1 | 11/2003 | Bernstein et al. |
| 2003/0224057 A1 | 12/2003 | Martin-Letellier et al. |
| 2003/0224059 A1 | 12/2003 | Lerner et al. |
| 2003/0225047 A1 | 12/2003 | Caubel et al. |
| 2003/0225048 A1 | 12/2003 | Caubel et al. |
| 2003/0225050 A1 | 12/2003 | Eichardt et al. |
| 2003/0228686 A1 | 12/2003 | Klausner et al. |
| 2003/0229057 A1 | 12/2003 | Caubel et al. |
| 2003/0235596 A1 | 12/2003 | Gao et al. |
| 2003/0236236 A1 | 12/2003 | Chen et al. |
| 2004/0009960 A1 | 1/2004 | Heil et al. |
| 2004/0022820 A1 | 2/2004 | Anderson |
| 2004/0034001 A1 | 2/2004 | Karara |
| 2004/0037881 A1 | 2/2004 | Guittard et al. |
| 2004/0039356 A1 | 2/2004 | Maki et al. |
| 2004/0043043 A1 | 3/2004 | Schlyter et al. |
| 2004/0043943 A1 | 3/2004 | Guittard et al. |

(56) References Cited

U.S. PATENT DOCUMENTS

| | | |
|---|---|---|
| 2004/0044080 A1 | 3/2004 | Place et al. |
| 2004/0048900 A1 | 3/2004 | Flood |
| 2004/0052824 A1 | 3/2004 | Abou Chacra-Vernet et al. |
| 2004/0073024 A1 | 4/2004 | Metcalf, III et al. |
| 2004/0077605 A1 | 4/2004 | Salvati et al. |
| 2004/0077606 A1 | 4/2004 | Salvati et al. |
| 2004/0087548 A1 | 5/2004 | Salvati et al. |
| 2004/0087564 A1 | 5/2004 | Wright et al. |
| 2004/0089308 A1 | 5/2004 | Welch |
| 2004/0092494 A9 | 5/2004 | Dudley |
| 2004/0092583 A1 | 5/2004 | Shanahan-Prendergast |
| 2004/0093261 A1 | 5/2004 | Jain et al. |
| 2004/0097468 A1 | 5/2004 | Wimalawansa |
| 2004/0101557 A1 | 5/2004 | Gibson et al. |
| 2004/0106542 A1 | 6/2004 | Deaver et al. |
| 2004/0110732 A1 | 6/2004 | Masini Eteve et al. |
| 2004/0131670 A1 | 7/2004 | Gao |
| 2004/0138103 A1 | 7/2004 | Patt |
| 2004/0142012 A1 | 7/2004 | Bunt et al. |
| 2004/0146539 A1 | 7/2004 | Gupta |
| 2004/0146894 A1 | 7/2004 | Warrington et al. |
| 2004/0161435 A1 | 8/2004 | Gupta |
| 2004/0176324 A1 | 9/2004 | Salvati et al. |
| 2004/0176336 A1 | 9/2004 | Rodriguez |
| 2004/0185104 A1 | 9/2004 | Piao et al. |
| 2004/0191207 A1 | 9/2004 | Lipari et al. |
| 2004/0191276 A1 | 9/2004 | Muni |
| 2004/0198706 A1 | 10/2004 | Carrara et al. |
| 2004/0210280 A1 | 10/2004 | Liedtke |
| 2004/0213744 A1 | 10/2004 | Lulla et al. |
| 2004/0219124 A1 | 11/2004 | Gupta |
| 2004/0225140 A1 | 11/2004 | Fernandez et al. |
| 2004/0234606 A1 | 11/2004 | Levine et al. |
| 2004/0241219 A1 | 12/2004 | Hille et al. |
| 2004/0243437 A1 | 12/2004 | Grace et al. |
| 2004/0253319 A1 | 12/2004 | Netke et al. |
| 2004/0259817 A1 | 12/2004 | Waldon et al. |
| 2004/0266745 A1 | 12/2004 | Schwanitz et al. |
| 2005/0003003 A1 | 1/2005 | Deaver et al. |
| 2005/0004088 A1 | 1/2005 | Hesch |
| 2005/0009800 A1 | 1/2005 | Thumbeck et al. |
| 2005/0014729 A1 | 1/2005 | Pulaski |
| 2005/0020550 A1 | 1/2005 | Morris et al. |
| 2005/0020552 A1 | 1/2005 | Aschkenasay et al. |
| 2005/0021009 A1 | 1/2005 | Massara et al. |
| 2005/0025833 A1 | 2/2005 | Aschkenasay et al. |
| 2005/0031651 A1 | 2/2005 | Gervais et al. |
| 2005/0042173 A1 | 2/2005 | Besse et al. |
| 2005/0042268 A1 | 2/2005 | Aschkenasay et al. |
| 2005/0048116 A1 | 3/2005 | Straub et al. |
| 2005/0054991 A1 | 3/2005 | Tobyn et al. |
| 2005/0079138 A1 | 4/2005 | Chickering, III et al. |
| 2005/0085453 A1 | 4/2005 | Govindarajan |
| 2005/0101579 A1 | 5/2005 | Shippen |
| 2005/0113350 A1 | 5/2005 | Duesterberg et al. |
| 2005/0118244 A1 | 6/2005 | Theobald et al. |
| 2005/0118272 A1 | 6/2005 | Besse et al. |
| 2005/0129756 A1 | 6/2005 | Podhaisky et al. |
| 2005/0152956 A1 | 7/2005 | Dudley |
| 2005/0153946 A1 | 7/2005 | Hirsh et al. |
| 2005/0164977 A1 | 7/2005 | Coelingh Bennink |
| 2005/0182105 A1 | 8/2005 | Nirschl et al. |
| 2005/0186141 A1 | 8/2005 | Gonda et al. |
| 2005/0187267 A1 | 8/2005 | Hamann et al. |
| 2005/0192253 A1 | 9/2005 | Salvati et al. |
| 2005/0192310 A1 | 9/2005 | Gavai et al. |
| 2005/0196434 A1 | 9/2005 | Brierre |
| 2005/0207990 A1 | 9/2005 | Funke et al. |
| 2005/0209209 A1 | 9/2005 | Koch et al. |
| 2005/0214384 A1 | 9/2005 | Juturu et al. |
| 2005/0220825 A1 | 10/2005 | Funke et al. |
| 2005/0220900 A1 | 10/2005 | Popp et al. |
| 2005/0222106 A1 | 10/2005 | Bracht |
| 2005/0228692 A1 | 10/2005 | Hodgdon |
| 2005/0228718 A1 | 10/2005 | Austin |
| 2005/0239747 A1 | 10/2005 | Yang et al. |
| 2005/0239758 A1 | 10/2005 | Roby |
| 2005/0244360 A1 | 11/2005 | Billoni |
| 2005/0244522 A1 | 11/2005 | Carrara et al. |
| 2005/0245902 A1 | 11/2005 | Cornish et al. |
| 2005/0250746 A1 | 11/2005 | Iammatteo |
| 2005/0250750 A1 | 11/2005 | Cummings et al. |
| 2005/0250753 A1 | 11/2005 | Fink et al. |
| 2005/0256028 A1 | 11/2005 | Yun et al. |
| 2005/0266078 A1 | 12/2005 | Jorda et al. |
| 2005/0266088 A1 | 12/2005 | Hinrichs et al. |
| 2005/0271597 A1 | 12/2005 | Keith |
| 2005/0271598 A1 | 12/2005 | Friedman et al. |
| 2005/0272685 A1 | 12/2005 | Hung |
| 2005/0272712 A1 | 12/2005 | Grubb et al. |
| 2006/0009428 A1 | 1/2006 | Grubb et al. |
| 2006/0014728 A1 | 1/2006 | Chwalisz et al. |
| 2006/0018937 A1 | 1/2006 | Friedman et al. |
| 2006/0019978 A1 | 1/2006 | Balog |
| 2006/0020002 A1 | 1/2006 | Salvati et al. |
| 2006/0030615 A1 | 2/2006 | Fensome et al. |
| 2006/0034889 A1 | 2/2006 | Jo et al. |
| 2006/0034904 A1 | 2/2006 | Weimann |
| 2006/0040904 A1* | 2/2006 | Ahmed et al. ................ 514/182 |
| 2006/0051391 A1 | 3/2006 | Dvoskin et al. |
| 2006/0052341 A1 | 3/2006 | Cornish et al. |
| 2006/0069031 A1 | 3/2006 | Loumaye |
| 2006/0078618 A1 | 4/2006 | Constantinides et al. |
| 2006/0083778 A1 | 4/2006 | Allison et al. |
| 2006/0084704 A1 | 4/2006 | Shih et al. |
| 2006/0088580 A1 | 4/2006 | Meconi et al. |
| 2006/0089337 A1 | 4/2006 | Casper et al. |
| 2006/0093678 A1 | 5/2006 | Chickering, III et al. |
| 2006/0100180 A1 | 5/2006 | Nubbemeyer et al. |
| 2006/0106004 A1 | 5/2006 | Brody et al. |
| 2006/0110415 A1 | 5/2006 | Gupta |
| 2006/0111424 A1 | 5/2006 | Salvati et al. |
| 2006/0121102 A1 | 6/2006 | Chiang |
| 2006/0121626 A1 | 6/2006 | Imrich |
| 2006/0134188 A1 | 6/2006 | Podhaisky et al. |
| 2006/0135619 A1 | 6/2006 | Kick et al. |
| 2006/0165744 A1 | 7/2006 | Jamil et al. |
| 2006/0193789 A1 | 8/2006 | Tamarkin et al. |
| 2006/0194775 A1 | 8/2006 | Tofovic et al. |
| 2006/0204557 A1 | 9/2006 | Gupta et al. |
| 2006/0233743 A1 | 10/2006 | Kelly |
| 2006/0233841 A1 | 10/2006 | Brodbeck et al. |
| 2006/0235037 A1 | 10/2006 | Purandare et al. |
| 2006/0240111 A1 | 10/2006 | Fernandez et al. |
| 2006/0246122 A1 | 11/2006 | Langguth et al. |
| 2006/0247216 A1 | 11/2006 | Haj-Yehia |
| 2006/0247221 A1 | 11/2006 | Coelingh Bennink et al. |
| 2006/0251581 A1 | 11/2006 | McIntyre et al. |
| 2006/0252049 A1 | 11/2006 | Shuler et al. |
| 2006/0257472 A1 | 11/2006 | Neilsen |
| 2006/0275218 A1 | 12/2006 | Tamarkin et al. |
| 2006/0275360 A1 | 12/2006 | Ahmed et al. |
| 2006/0276414 A1 | 12/2006 | Coelingh Bennink et al. |
| 2006/0280771 A1 | 12/2006 | Groenewegen et al. |
| 2006/0280797 A1 | 12/2006 | Shoichet et al. |
| 2006/0280800 A1 | 12/2006 | Nagi et al. |
| 2006/0292223 A1 | 12/2006 | Woolfson et al. |
| 2007/0004693 A1 | 1/2007 | Woolfson et al. |
| 2007/0004694 A1 | 1/2007 | Woolfson et al. |
| 2007/0009559 A1 | 1/2007 | Li et al. |
| 2007/0009594 A1 | 1/2007 | Grubb et al. |
| 2007/0010550 A1 | 1/2007 | McKenzie |
| 2007/0014839 A1 | 1/2007 | Bracht |
| 2007/0015698 A1 | 1/2007 | Kleinman et al. |
| 2007/0021360 A1 | 1/2007 | Nyce et al. |
| 2007/0027201 A1 | 2/2007 | McComas et al. |
| 2007/0031491 A1 | 2/2007 | Levine et al. |
| 2007/0037780 A1 | 2/2007 | Ebert et al. |
| 2007/0037782 A1 | 2/2007 | Hibino et al. |
| 2007/0042038 A1 | 2/2007 | Besse |
| 2007/0060589 A1 | 3/2007 | Purandare et al. |
| 2007/0066628 A1 | 3/2007 | Zhang et al. |
| 2007/0066637 A1 | 3/2007 | Zhang et al. |
| 2007/0066675 A1 | 3/2007 | Zhang et al. |

(56) References Cited

U.S. PATENT DOCUMENTS

| | | |
|---|---|---|
| 2007/0078091 A1 | 4/2007 | Hubler et al. |
| 2007/0088029 A1 | 4/2007 | Balog et al. |
| 2007/0093548 A1 | 4/2007 | Diffendal et al. |
| 2007/0116729 A1 | 5/2007 | Palepu |
| 2007/0116829 A1 | 5/2007 | Prakash et al. |
| 2007/0128263 A1 | 6/2007 | Gargiulo et al. |
| 2007/0154533 A1 | 7/2007 | Dudley |
| 2007/0167418 A1 | 7/2007 | Ferguson |
| 2007/0178166 A1 | 8/2007 | Bernstein et al. |
| 2007/0184558 A1 | 8/2007 | Roth et al. |
| 2007/0185068 A1 | 8/2007 | Ferguson et al. |
| 2007/0190022 A1 | 8/2007 | Chiao et al. |
| 2007/0191319 A1 | 8/2007 | Ke et al. |
| 2007/0196415 A1 | 8/2007 | Chen et al. |
| 2007/0196433 A1 | 8/2007 | Ron et al. |
| 2007/0207225 A1 | 9/2007 | Squadrito |
| 2007/0225281 A1 | 9/2007 | Zhang et al. |
| 2007/0232574 A1 | 10/2007 | Galey et al. |
| 2007/0238713 A1 | 10/2007 | Gast et al. |
| 2007/0243229 A1 | 10/2007 | Smith et al. |
| 2007/0248658 A1 | 10/2007 | Zurdo Schroeder et al. |
| 2007/0254858 A1 | 11/2007 | Cronk |
| 2007/0255197 A1 | 11/2007 | Humberstone et al. |
| 2007/0264309 A1 | 11/2007 | Chollet et al. |
| 2007/0264345 A1 | 11/2007 | Eros et al. |
| 2007/0264349 A1 | 11/2007 | Lee et al. |
| 2007/0286819 A1 | 12/2007 | DeVries et al. |
| 2007/0287688 A1 | 12/2007 | Chan et al. |
| 2007/0287789 A1 | 12/2007 | Jones et al. |
| 2007/0292359 A1 | 12/2007 | Friedman et al. |
| 2007/0292387 A1 | 12/2007 | Jon et al. |
| 2007/0292461 A1 | 12/2007 | Tamarkin et al. |
| 2007/0292493 A1 | 12/2007 | Brierre |
| 2007/0298089 A1 | 12/2007 | Saeki et al. |
| 2008/0026035 A1 | 1/2008 | Chollet et al. |
| 2008/0026040 A1 | 1/2008 | Farr et al. |
| 2008/0026062 A1 | 1/2008 | Farr et al. |
| 2008/0038219 A1 | 2/2008 | Carlson et al. |
| 2008/0038350 A1 | 2/2008 | Gerecke et al. |
| 2008/0039405 A1 | 2/2008 | Langley et al. |
| 2008/0050317 A1 | 2/2008 | Tamarkin et al. |
| 2008/0051351 A1 | 2/2008 | Ghisalberti |
| 2008/0063607 A1 | 3/2008 | Tamarkin et al. |
| 2008/0069779 A1 | 3/2008 | Tamarkin et al. |
| 2008/0069791 A1 | 3/2008 | Beissert |
| 2008/0085877 A1 | 4/2008 | Bortz |
| 2008/0095831 A1 | 4/2008 | McGraw |
| 2008/0095838 A1 | 4/2008 | Abou Chacra-Vernet |
| 2008/0113953 A1 | 5/2008 | DeVries et al. |
| 2008/0114050 A1 | 5/2008 | Fensome et al. |
| 2008/0119537 A1 | 5/2008 | Zhang et al. |
| 2008/0125402 A1 | 5/2008 | Dilberti |
| 2008/0138379 A1 | 6/2008 | Jennings-Spring |
| 2008/0138390 A1 | 6/2008 | Hsu et al. |
| 2008/0139392 A1 | 6/2008 | Acosta Zara et al. |
| 2008/0145423 A1 | 6/2008 | Khan et al. |
| 2008/0153789 A1 | 6/2008 | Dmowski et al. |
| 2008/0175814 A1 | 7/2008 | Phiasivongsa et al. |
| 2008/0175905 A1 | 7/2008 | Liu et al. |
| 2008/0175908 A1 | 7/2008 | Liu et al. |
| 2008/0188829 A1 | 8/2008 | Creasy |
| 2008/0206156 A1 | 8/2008 | Cronk |
| 2008/0206159 A1 | 8/2008 | Tamarkin et al. |
| 2008/0206161 A1 | 8/2008 | Tamarkin et al. |
| 2008/0214512 A1 | 9/2008 | Seitz et al. |
| 2008/0220069 A1 | 9/2008 | Allison |
| 2008/0226698 A1 | 9/2008 | Tang et al. |
| 2008/0227763 A1 | 9/2008 | Lanquetin et al. |
| 2008/0234199 A1 | 9/2008 | Katamreddy |
| 2008/0234240 A1 | 9/2008 | Duesterberg et al. |
| 2008/0255078 A1 | 10/2008 | Katamreddy |
| 2008/0255089 A1 | 10/2008 | Katamreddy |
| 2008/0261931 A1 | 10/2008 | Hedner et al. |
| 2008/0299220 A1 | 12/2008 | Tamarkin et al. |
| 2008/0306036 A1 | 12/2008 | Katamreddy |
| 2008/0312197 A1 | 12/2008 | Rodriguez |
| 2008/0312198 A1 | 12/2008 | Rodriguez |
| 2008/0319078 A1 | 12/2008 | Katamreddy |
| 2009/0004246 A1 | 1/2009 | Woolfson et al. |
| 2009/0010968 A1 | 1/2009 | Allart et al. |
| 2009/0011041 A1 | 1/2009 | Musaeva et al. |
| 2009/0017120 A1 | 1/2009 | Trimble et al. |
| 2009/0022683 A1 | 1/2009 | Song et al. |
| 2009/0047357 A1 | 2/2009 | Tomohira et al. |
| 2009/0053294 A1 | 2/2009 | Prendergast |
| 2009/0060982 A1 | 3/2009 | Ron et al. |
| 2009/0060997 A1 | 3/2009 | Seitz et al. |
| 2009/0068118 A1 | 3/2009 | Eini et al. |
| 2009/0081206 A1 | 3/2009 | Leibovitz |
| 2009/0081278 A1 | 3/2009 | De Graaff et al. |
| 2009/0081303 A1 | 3/2009 | Savoir et al. |
| 2009/0092656 A1 | 4/2009 | Klamerus et al. |
| 2009/0093440 A1 | 4/2009 | Murad |
| 2009/0098069 A1 | 4/2009 | Vacca |
| 2009/0099106 A1 | 4/2009 | Phiasivongsa et al. |
| 2009/0099149 A1 | 4/2009 | Liu et al. |
| 2009/0130029 A1 | 5/2009 | Tamarkin et al. |
| 2009/0131385 A1 | 5/2009 | Voskuhl |
| 2009/0137478 A1 | 5/2009 | Bernstein et al. |
| 2009/0137538 A1 | 5/2009 | Klamerus et al. |
| 2009/0143344 A1 | 6/2009 | Chang |
| 2009/0164341 A1 | 6/2009 | Sunvold et al. |
| 2009/0175799 A1 | 7/2009 | Tamarkin et al. |
| 2009/0181088 A1 | 7/2009 | Song et al. |
| 2009/0186081 A1 | 7/2009 | Holm et al. |
| 2009/0197843 A1 | 8/2009 | Notelovitz et al. |
| 2009/0203658 A1 | 8/2009 | Marx et al. |
| 2009/0214474 A1 | 8/2009 | Jennings |
| 2009/0227025 A1 | 9/2009 | Nichols et al. |
| 2009/0227550 A1 | 9/2009 | Mattern |
| 2009/0232897 A1 | 9/2009 | Sahoo et al. |
| 2009/0258096 A1 | 10/2009 | Cohen |
| 2009/0264395 A1 | 10/2009 | Creasy |
| 2009/0269403 A1 | 10/2009 | Shaked et al. |
| 2009/0285772 A1 | 11/2009 | Phiasivongsa et al. |
| 2009/0285869 A1 | 11/2009 | Trimble |
| 2009/0318558 A1 | 12/2009 | Kim et al. |
| 2009/0324714 A1 | 12/2009 | Liu et al. |
| 2009/0325916 A1 | 12/2009 | Zhang et al. |
| 2010/0008985 A1 | 1/2010 | Pellikaan et al. |
| 2010/0028360 A1 | 2/2010 | Atwood |
| 2010/0034838 A1 | 2/2010 | Staniforth et al. |
| 2010/0034880 A1 | 2/2010 | Sintov et al. |
| 2010/0040671 A1 | 2/2010 | Ahmed et al. |
| 2010/0048523 A1 | 2/2010 | Bachman et al. |
| 2010/0055138 A1 | 3/2010 | Margulies et al. |
| 2010/0074959 A1 | 3/2010 | Hansom et al. |
| 2010/0086501 A1 | 4/2010 | Chang et al. |
| 2010/0086599 A1 | 4/2010 | Huempel et al. |
| 2010/0092568 A1 | 4/2010 | Lerner et al. |
| 2010/0105071 A1 | 4/2010 | Laufer et al. |
| 2010/0119585 A1 | 5/2010 | Hille et al. |
| 2010/0129320 A1 | 5/2010 | Phiasivongsa et al. |
| 2010/0136105 A1 | 6/2010 | Chen et al. |
| 2010/0137265 A1 | 6/2010 | Leonard |
| 2010/0137271 A1 | 6/2010 | Chen et al. |
| 2010/0143420 A1 | 6/2010 | Shenoy et al. |
| 2010/0143481 A1 | 6/2010 | Shenoy et al. |
| 2010/0150993 A1 | 6/2010 | Theobald et al. |
| 2010/0152144 A1 | 6/2010 | Hermsmeyer |
| 2010/0168228 A1 | 7/2010 | Bose et al. |
| 2010/0183723 A1 | 7/2010 | Laurent-Applegate et al. |
| 2010/0184736 A1 | 7/2010 | Coelingh Bennink et al. |
| 2010/0190758 A1 | 7/2010 | Fauser et al. |
| 2010/0204326 A1 | 8/2010 | D Souza |
| 2010/0210994 A1 | 8/2010 | Zarif |
| 2010/0221195 A1 | 9/2010 | Tamarkin et al. |
| 2010/0227797 A1 | 9/2010 | Axelson et al. |
| 2010/0240626 A1 | 9/2010 | Kulkarni et al. |
| 2010/0247482 A1 | 9/2010 | Cui et al. |
| 2010/0247632 A1 | 9/2010 | Dong et al. |
| 2010/0247635 A1 | 9/2010 | Rosenberg et al. |
| 2010/0255085 A1 | 10/2010 | Liu et al. |
| 2010/0273730 A1 | 10/2010 | Hsu et al. |

(56) References Cited

U.S. PATENT DOCUMENTS

| | | |
|---|---|---|
| 2010/0278759 A1 | 11/2010 | Murad |
| 2010/0279988 A1 | 11/2010 | Setiawan et al. |
| 2010/0291191 A1 | 11/2010 | Shoichet et al. |
| 2010/0292199 A1 | 11/2010 | Leverd et al. |
| 2010/0303825 A9 | 12/2010 | Sirbasku |
| 2010/0312137 A1 | 12/2010 | Gilmour et al. |
| 2010/0316724 A1 | 12/2010 | Whitfield et al. |
| 2010/0322884 A1 | 12/2010 | Dipietro et al. |
| 2010/0330168 A1 | 12/2010 | Gicquel et al. |
| 2011/0028439 A1 | 2/2011 | Witt-Enderby et al. |
| 2011/0039814 A1 | 2/2011 | Huatan et al. |
| 2011/0053845 A1 | 3/2011 | Levine et al. |
| 2011/0066473 A1 | 3/2011 | Bernick et al. |
| 2011/0076775 A1 | 3/2011 | Stewart et al. |
| 2011/0076776 A1 | 3/2011 | Stewart et al. |
| 2011/0086825 A1 | 4/2011 | Chatroux |
| 2011/0087192 A1 | 4/2011 | Uhland et al. |
| 2011/0091555 A1 | 4/2011 | De Luigi Bruschi et al. |
| 2011/0098258 A1 | 4/2011 | Masini-Eteve et al. |
| 2011/0098631 A1 | 4/2011 | McIntyre et al. |
| 2011/0104268 A1 | 5/2011 | Pachot et al. |
| 2011/0104289 A1 | 5/2011 | Savoir Vilboeuf et al. |
| 2011/0130372 A1 | 6/2011 | Agostinacchio et al. |
| 2011/0135719 A1 | 6/2011 | Besins et al. |
| 2011/0142945 A1 | 6/2011 | Chen et al. |
| 2011/0152840 A1 | 6/2011 | Lee et al. |
| 2011/0158920 A1 | 6/2011 | Morley et al. |
| 2011/0171140 A1 | 7/2011 | Illum et al. |
| 2011/0182997 A1 | 7/2011 | Lewis et al. |
| 2011/0190201 A1 | 8/2011 | Hyde et al. |
| 2011/0195031 A1 | 8/2011 | Du |
| 2011/0195114 A1 | 8/2011 | Carrara et al. |
| 2011/0195944 A1 | 8/2011 | Mura et al. |
| 2011/0217341 A1 | 9/2011 | Sah |
| 2011/0238003 A1 | 9/2011 | Bruno Raimondi et al. |
| 2011/0244043 A1 | 10/2011 | Xu et al. |
| 2011/0250256 A1 | 10/2011 | Hyun Oh et al. |
| 2011/0250259 A1 | 10/2011 | Buckman |
| 2011/0250274 A1 | 10/2011 | Shaked et al. |
| 2011/0256092 A1 | 10/2011 | Phiasivongsa et al. |
| 2011/0262373 A1 | 10/2011 | Umbert Millet |
| 2011/0262494 A1 | 10/2011 | Achleitner et al. |
| 2011/0268665 A1 | 11/2011 | Tamarkin et al. |
| 2011/0275584 A1 | 11/2011 | Wilckens et al. |
| 2011/0281832 A1 | 11/2011 | Li et al. |
| 2011/0287094 A1 | 11/2011 | Penhasi et al. |
| 2011/0293720 A1 | 12/2011 | General et al. |
| 2011/0294738 A1 | 12/2011 | Ren et al. |
| 2011/0300167 A1 | 12/2011 | McMurry et al. |
| 2011/0301087 A1 | 12/2011 | McBride et al. |
| 2011/0306579 A1 | 12/2011 | Stein |
| 2011/0311592 A1 | 12/2011 | Birbara |
| 2011/0312927 A1 | 12/2011 | Nachaegari et al. |
| 2011/0312928 A1 | 12/2011 | Nachaegari et al. |
| 2011/0318405 A1 | 12/2011 | Erwin |
| 2011/0318431 A1 | 12/2011 | Gulati |
| 2012/0009276 A1 | 1/2012 | De Groote |
| 2012/0015350 A1 | 1/2012 | Nabatiyan et al. |
| 2012/0021041 A1 | 1/2012 | Rossi et al. |
| 2012/0028888 A1 | 2/2012 | Janz et al. |
| 2012/0028910 A1 | 2/2012 | Takruri et al. |
| 2012/0028936 A1 | 2/2012 | Gloger et al. |
| 2012/0045532 A1 | 2/2012 | Cohen |
| 2012/0046264 A1 | 2/2012 | Simes et al. |
| 2012/0046518 A1 | 2/2012 | Yoakum et al. |
| 2012/0052077 A1 | 3/2012 | Truitt, III et al. |
| 2012/0058171 A1 | 3/2012 | De Graaff et al. |
| 2012/0058962 A1 | 3/2012 | Cumming et al. |
| 2012/0058979 A1 | 3/2012 | Keith et al. |
| 2012/0064135 A1 | 3/2012 | Levin et al. |
| 2012/0065179 A1 | 3/2012 | Andersson |
| 2012/0065221 A1 | 3/2012 | Babul |
| 2012/0087872 A1 | 4/2012 | Tamarkin et al. |
| 2012/0101073 A1 | 4/2012 | Mannion et al. |
| 2012/0121517 A1 | 5/2012 | Song et al. |
| 2012/0121692 A1 | 5/2012 | Xu et al. |
| 2012/0122829 A1 | 5/2012 | Taravella et al. |
| 2012/0128625 A1 | 5/2012 | Shalwitz et al. |
| 2012/0128654 A1 | 5/2012 | Terpstra et al. |
| 2012/0128683 A1 | 5/2012 | Shantha |
| 2012/0128733 A1 | 5/2012 | Perrin et al. |
| 2012/0128777 A1 | 5/2012 | Keck et al. |
| 2012/0129773 A1 | 5/2012 | Geier et al. |
| 2012/0129819 A1 | 5/2012 | Vancaillie et al. |
| 2012/0136013 A1 | 5/2012 | Li et al. |
| 2012/0142645 A1 | 6/2012 | Marx |
| 2012/0148670 A1 | 6/2012 | Kim et al. |
| 2012/0149748 A1 | 6/2012 | Shanler et al. |
| 2012/0172343 A1 | 7/2012 | Lindenthal et al. |
| 2012/0184515 A1 | 7/2012 | Klar et al. |
| 2012/0231052 A1 | 9/2012 | Sitruk Ware et al. |
| 2012/0232011 A1 | 9/2012 | Kneissel et al. |
| 2012/0232042 A1 | 9/2012 | Klar et al. |
| 2012/0263679 A1 | 10/2012 | Marlow et al. |
| 2012/0269721 A1 | 10/2012 | Weng et al. |
| 2012/0277249 A1 | 11/2012 | Andersson et al. |
| 2012/0277727 A1 | 11/2012 | Doshi et al. |
| 2012/0283671 A1 | 11/2012 | Shibata et al. |
| 2012/0295911 A1 | 11/2012 | Mannion et al. |
| 2012/0301517 A1 | 11/2012 | Zhang et al. |
| 2012/0301538 A1 | 11/2012 | Gordon Beresford et al. |
| 2012/0302535 A1 | 11/2012 | Caufriez et al. |
| 2012/0316130 A1 | 12/2012 | Hendrix |
| 2012/0316496 A1 | 12/2012 | Hoffmann et al. |
| 2012/0321579 A1 | 12/2012 | Edelson et al. |
| 2012/0322779 A9 | 12/2012 | Voskuhl |
| 2012/0328549 A1 | 12/2012 | Edelson et al. |
| 2012/0329738 A1 | 12/2012 | Liu |
| 2013/0004619 A1 | 1/2013 | Chow et al. |
| 2013/0011342 A1 | 1/2013 | Tamarkin et al. |
| 2013/0017239 A1 | 1/2013 | Viladot Petit et al. |
| 2013/0022674 A1 | 1/2013 | Dudley et al. |
| 2013/0023505 A1 | 1/2013 | Garfield et al. |
| 2013/0023823 A1 | 1/2013 | Simpson et al. |
| 2013/0028850 A1 | 1/2013 | Tamarkin et al. |
| 2013/0029947 A1 | 1/2013 | Nachaegari et al. |
| 2013/0029957 A1 | 1/2013 | Giliyar et al. |
| 2013/0045266 A1 | 2/2013 | Choi et al. |
| 2013/0045953 A1 | 2/2013 | Sitruk Ware et al. |
| 2013/0059795 A1 | 3/2013 | Lo et al. |
| 2013/0064897 A1 | 3/2013 | Binay |
| 2013/0072466 A1 | 3/2013 | Choi et al. |
| 2013/0084257 A1 | 4/2013 | Ishida et al. |
| 2013/0085123 A1 | 4/2013 | Li et al. |
| 2013/0089574 A1 | 4/2013 | Schmidt Gollwitzer et al. |
| 2013/0090318 A1 | 4/2013 | Ulmann et al. |
| 2013/0102781 A1 | 4/2013 | Bevill et al. |
| 2013/0108551 A1 | 5/2013 | Langereis et al. |
| 2013/0116215 A1 | 5/2013 | Coma et al. |
| 2013/0116222 A1 | 5/2013 | Arnold et al. |
| 2013/0122051 A1 | 5/2013 | Abidi et al. |
| 2013/0123175 A1 | 5/2013 | Hill et al. |
| 2013/0123220 A1 | 5/2013 | Queiroz |
| 2013/0123351 A1 | 5/2013 | Dewitt |
| 2013/0129818 A1 | 5/2013 | Bernick et al. |
| 2013/0131027 A1 | 5/2013 | Pakkalin et al. |
| 2013/0131028 A1 | 5/2013 | Snyder et al. |
| 2013/0131029 A1 | 5/2013 | Geertman et al. |
| 2013/0149314 A1 | 6/2013 | Bullerdiek et al. |
| 2013/0164225 A1 | 6/2013 | Tamarkin et al. |
| 2013/0164346 A1 | 6/2013 | Lee et al. |
| 2013/0165744 A1 | 6/2013 | Carson et al. |
| 2013/0178452 A1 | 7/2013 | King |
| 2013/0183254 A1 | 7/2013 | Zhou et al. |
| 2013/0183325 A1 | 7/2013 | Bottoni et al. |
| 2013/0189193 A1 | 7/2013 | Tamarkin et al. |
| 2013/0189196 A1 | 7/2013 | Tamarkin et al. |
| 2013/0189230 A1 | 7/2013 | Shoichet et al. |
| 2013/0189368 A1 | 7/2013 | Mosqueira et al. |
| 2013/0210709 A1 | 8/2013 | McMurry et al. |
| 2013/0216550 A1 | 8/2013 | Penninger et al. |
| 2013/0216596 A1 | 8/2013 | Viladot Petit et al. |
| 2013/0224177 A1 | 8/2013 | Kim et al. |
| 2013/0224257 A1 | 8/2013 | Sah et al. |

(56) References Cited

U.S. PATENT DOCUMENTS

| | | |
|---|---|---|
| 2013/0224268 A1 | 8/2013 | Alam et al. |
| 2013/0224300 A1 | 8/2013 | Maggio |
| 2013/0225412 A1 | 8/2013 | Sardari Lodriche et al. |
| 2013/0225542 A1 | 8/2013 | Poegh et al. |
| 2013/0226113 A1 | 8/2013 | Schumacher et al. |
| 2013/0243696 A1 | 9/2013 | Wang et al. |
| 2013/0245253 A1 | 9/2013 | Marx et al. |
| 2013/0245570 A1 | 9/2013 | Jackson |
| 2013/0261096 A1 | 10/2013 | Merian et al. |
| 2013/0266645 A1 | 10/2013 | Becker et al. |
| 2013/0267485 A1 | 10/2013 | Da Silva |
| 2013/0273167 A1 | 10/2013 | Lee et al. |
| 2013/0274211 A1 | 10/2013 | Burman et al. |
| 2013/0280213 A1 | 10/2013 | Voskuhl |
| 2013/0316374 A1 | 11/2013 | Penninger et al. |
| 2013/0317065 A1 | 11/2013 | Tatani et al. |
| 2013/0317315 A1 | 11/2013 | Lu et al. |
| 2013/0324565 A1 | 12/2013 | Li et al. |
| 2013/0331363 A1 | 12/2013 | Li et al. |
| 2013/0338122 A1 | 12/2013 | Bernick et al. |
| 2013/0338123 A1 | 12/2013 | Bernick et al. |
| 2013/0338124 A1 | 12/2013 | Li et al. |
| 2013/0345187 A1 | 12/2013 | Rodriguez Oquendo |
| 2014/0018335 A1 | 1/2014 | Tatani et al. |
| 2014/0024590 A1 | 1/2014 | Weidhaas et al. |
| 2014/0031289 A1 | 1/2014 | Song et al. |
| 2014/0031323 A1 | 1/2014 | Perez |
| 2014/0066416 A1 | 3/2014 | Leunis et al. |
| 2014/0072531 A1 | 3/2014 | Kim et al. |
| 2014/0079686 A1 | 3/2014 | Prouty et al. |
| 2014/0088051 A1 | 3/2014 | Bernick et al. |
| 2014/0088058 A1 | 3/2014 | Maurizio |
| 2014/0088059 A1 | 3/2014 | Perumal et al. |
| 2014/0094426 A1 | 4/2014 | Drummond et al. |
| 2014/0094440 A1 | 4/2014 | Bernick et al. |
| 2014/0094441 A1 | 4/2014 | Bernick et al. |
| 2014/0099362 A1 | 4/2014 | Bernick et al. |
| 2014/0100159 A1 | 4/2014 | Conrad |
| 2014/0100204 A1 | 4/2014 | Bernick et al. |
| 2014/0100205 A1 | 4/2014 | Bernick et al. |
| 2014/0100206 A1 | 4/2014 | Bernick et al. |
| 2014/0113889 A1 | 4/2014 | Connor et al. |
| 2014/0127185 A1 | 5/2014 | Stein et al. |
| 2014/0127280 A1 | 5/2014 | Duesterberg et al. |
| 2014/0127308 A1 | 5/2014 | Opara et al. |
| 2014/0128798 A1 | 5/2014 | Janson et al. |
| 2014/0148491 A1 | 5/2014 | Valia et al. |
| 2014/0186332 A1 | 7/2014 | Ezrin et al. |
| 2014/0187487 A1 | 7/2014 | Shoichet et al. |
| 2014/0193523 A1 | 7/2014 | Henry |
| 2014/0194396 A1 | 7/2014 | Li et al. |
| 2014/0206616 A1 | 7/2014 | Ko et al. |
| 2014/0213565 A1 | 7/2014 | Bernick et al. |
| 2014/0329783 A1 | 11/2014 | Bernick et al. |
| 2014/0371182 A1 | 12/2014 | Bernick et al. |
| 2014/0371183 A1 | 12/2014 | Bernick et al. |
| 2014/0371184 A1 | 12/2014 | Bernick et al. |
| 2014/0371185 A1 | 12/2014 | Bernick et al. |
| 2015/0031654 A1 | 1/2015 | Amadio |
| 2015/0045335 A1 | 2/2015 | Bernick et al. |
| 2015/0133421 A1 | 5/2015 | Bernick et al. |

FOREIGN PATENT DOCUMENTS

| | | |
|---|---|---|
| EP | 275716 A1 | 7/1988 |
| EP | 622075 A1 | 11/1994 |
| EP | 785211 A1 | 7/1997 |
| EP | 785212 A1 | 7/1997 |
| EP | 811381 A1 | 12/1997 |
| EP | 1094781 B1 | 7/2008 |
| EP | 2191833 A1 | 6/2010 |
| GB | 452238 A | 8/1936 |
| GB | 720561 A | 12/1954 |
| GB | 848881 A | 9/1960 |
| GB | 874368 A | 8/1961 |
| GB | 1589946 A | 5/1981 |
| IN | 2005KOL00053 | 8/2005 |
| IN | 216026 | 3/2008 |
| IN | 244217 | 11/2010 |
| WO | 9011064 | 10/1990 |
| WO | 9317686 | 9/1993 |
| WO | 9422426 | 10/1994 |
| WO | 9530409 | 11/1995 |
| WO | 9609826 | 4/1996 |
| WO | 9619975 | 7/1996 |
| WO | 9630000 | 10/1996 |
| WO | 9705491 | 2/1997 |
| WO | 9743989 | 11/1997 |
| WO | 9810293 | 3/1998 |
| WO | 9832465 | 7/1998 |
| WO | 9851280 | 11/1998 |
| WO | 9932072 | 7/1999 |
| WO | 9939700 | 8/1999 |
| WO | 9942109 | 8/1999 |
| WO | 9943304 | 9/1999 |
| WO | 9948477 | 9/1999 |
| WO | 9953910 | 10/1999 |
| WO | 9963974 | 12/1999 |
| WO | 0001351 | 1/2000 |
| WO | 0006175 | 2/2000 |
| WO | 0038659 | 6/2000 |
| WO | 0045795 | 8/2000 |
| WO | 0050007 | 8/2000 |
| WO | 0059577 | 10/2000 |
| WO | 0076522 | 12/2000 |
| WO | 0137808 | 5/2001 |
| WO | 0154699 | 8/2001 |
| WO | 0160325 | 8/2001 |
| WO | 0207700 | 1/2002 |
| WO | 0211768 | 2/2002 |
| WO | 0222132 | 3/2002 |
| WO | 0240008 | 5/2002 |
| WO | 0241878 | 5/2002 |
| WO | 02053131 | 7/2002 |
| WO | 02078602 | 10/2002 |
| WO | 02078604 | 10/2002 |
| WO | 03028667 | 4/2003 |
| WO | 03041718 | 5/2003 |
| WO | 03041741 | 5/2003 |
| WO | 03068186 | 8/2003 |
| WO | 03077923 | 9/2003 |
| WO | 03082254 | 10/2003 |
| WO | 03092588 | 11/2003 |
| WO | 2004014397 A1 | 2/2004 |
| WO | 2004014432 | 2/2004 |
| WO | 2004017983 | 3/2004 |
| WO | 2004032897 | 4/2004 |
| WO | 2004052336 | 6/2004 |
| WO | 2004054540 | 7/2004 |
| WO | 2004080413 | 9/2004 |
| WO | 2005027911 | 3/2005 |
| WO | 2005030175 | 4/2005 |
| WO | 2005081825 | 9/2005 |
| WO | 2005087194 | 9/2005 |
| WO | 2005087199 | 9/2005 |
| WO | 2005105059 | 11/2005 |
| WO | 2005115335 | 12/2005 |
| WO | 2005120470 | 12/2005 |
| WO | 2005120517 | 12/2005 |
| WO | 2006013369 | 2/2006 |
| WO | 2006034090 | 3/2006 |
| WO | 2006036899 | 4/2006 |
| WO | 2006053172 | 5/2006 |
| WO | 2006105615 | 10/2006 |
| WO | 2006113505 | 10/2006 |
| WO | 2006138686 | 12/2006 |
| WO | 2006138735 | 12/2006 |
| WO | 2007045027 | 4/2007 |
| WO | 2007103294 | 9/2007 |
| WO | 2007120868 | 10/2007 |
| WO | 2007123790 | 11/2007 |
| WO | 2007124250 | 11/2007 |
| WO | 2007144151 | 12/2007 |

(56) References Cited

FOREIGN PATENT DOCUMENTS

| | | |
|---|---|---|
| WO | 2008049516 | 5/2008 |
| WO | 2008152444 | 12/2008 |
| WO | 2009002542 | 12/2008 |
| WO | 2009036311 | 3/2009 |
| WO | 2009040818 | 4/2009 |
| WO | 2009069006 | 6/2009 |
| WO | 2009098072 | 8/2009 |
| WO | 2009133352 | 11/2009 |
| WO | 2010033188 | 3/2010 |
| WO | 2010146872 | 12/2010 |
| WO | 2011000210 | 1/2011 |
| WO | 2011073995 | 6/2011 |
| WO | 2011120084 | 10/2011 |
| WO | 2011128336 | 10/2011 |
| WO | 2012009778 | 1/2012 |
| WO | 2012024361 | 2/2012 |
| WO | 2012055814 A1 | 5/2012 |
| WO | 2012055840 A1 | 5/2012 |
| WO | 2012065740 | 5/2012 |
| WO | 2012098090 A1 | 7/2012 |
| WO | 2012116277 A1 | 8/2012 |
| WO | 2012118563 A2 | 9/2012 |
| WO | 2012120365 A1 | 9/2012 |
| WO | 2012127501 A2 | 9/2012 |
| WO | 2012156561 A1 | 11/2012 |
| WO | 2012156822 A1 | 11/2012 |
| WO | 2012158483 A2 | 11/2012 |
| WO | 2012166909 A1 | 12/2012 |
| WO | 2012170578 A1 | 12/2012 |
| WO | 2013011501 A1 | 1/2013 |
| WO | 2013025449 A1 | 2/2013 |
| WO | 2013028639 A1 | 2/2013 |
| WO | 2013035101 A1 | 3/2013 |
| WO | 2013044067 A1 | 3/2013 |
| WO | 2013045404 A2 | 4/2013 |
| WO | 2013059285 A1 | 4/2013 |
| WO | 2013063279 A1 | 5/2013 |
| WO | 2013064620 A1 | 5/2013 |
| WO | 2013071281 A1 | 5/2013 |
| WO | 2013088254 | 6/2013 |
| WO | 2013102665 A1 | 7/2013 |
| WO | 2013106437 A1 | 7/2013 |
| WO | 2013113690 | 8/2013 |
| WO | 2013124415 A1 | 8/2013 |
| WO | 2013127727 A1 | 9/2013 |
| WO | 2013127728 A1 | 9/2013 |
| WO | 2013144356 A1 | 10/2013 |
| WO | 2013149258 A2 | 10/2013 |
| WO | 2013158454 A2 | 10/2013 |
| WO | 2013170052 A1 | 11/2013 |
| WO | 2013178587 A1 | 12/2013 |
| WO | 2013181449 A1 | 12/2013 |
| WO | 2013192248 | 12/2013 |
| WO | 2013192249 | 12/2013 |
| WO | 2013192250 | 12/2013 |
| WO | 2013192251 | 12/2013 |
| WO | 2014001904 A1 | 1/2014 |
| WO | 2014004424 A1 | 1/2014 |
| WO | 2014009434 A1 | 1/2014 |
| WO | 2014018569 A1 | 1/2014 |
| WO | 2014018570 A1 | 1/2014 |
| WO | 2014018571 A2 | 1/2014 |
| WO | 2014018856 A1 | 1/2014 |
| WO | 2014018932 A2 | 1/2014 |
| WO | 2014031958 A1 | 2/2014 |
| WO | 2014041120 A1 | 3/2014 |
| WO | 2014052792 A1 | 4/2014 |
| WO | 2014056897 A1 | 4/2014 |
| WO | 2014066442 A2 | 5/2014 |
| WO | 2014074846 A1 | 5/2014 |
| WO | 2014076231 A1 | 5/2014 |
| WO | 2014076569 A2 | 5/2014 |
| WO | 2014081598 A1 | 5/2014 |
| WO | 2014086739 A1 | 6/2014 |
| WO | 2014093114 A1 | 6/2014 |
| WO | 2014104784 A1 | 7/2014 |

OTHER PUBLICATIONS

Acarturk, Fusun, Mucoadhesive Vaginal Drug Delivery System, Recent Patents on Drug Delivery & Formulation, 2009, vol. 3, pp. 193-195.

Alabi, K. A., et al., Analysis of Fatty Acid Composition of Thevetia peruviana and Hura crepitans Seed oils using GC-FID, Fountain Journal of Nat. and Appl. Sciences, vol. 2(2), pp. 32-37, 2013, Osogbo.

Alexander, KS, Corn Oil, CAS No. 8001-30-7, Jan. 2009.

Alvarez et al., Ectopic uterine tissue as a chronic pain generator, Neuroscience, Dec. 6, 2012, 225: 269-272.

Application Note FT-IR: JI-AP-FT0508-008, CD spectra of pharmaceuticals substances—Steroids (2), JASCO International Co., Ltd., 2 pages.

Araya-Sibija et al., Crystallization of progesterone polymorphs using polymer-induced heteronucleation (PIHn) method, Drug Development and Industrial Pharmacy, Early Online, pp. 1-8, 2014, Informa Healthcare.

Araya-Sibija, Andrea M.A., Morphology Study of Progesterone Polymorphs Prepared by Polymer-Induced Heteronucleation (PIHn), Scanning vol. 35 pp. 213-221, 2013, Wiley Period., Inc.

Araya-Sibija, Andrea Manela, et al., Chemical Properties of Progesterone Selected Refer., SciFinder, 2014, American Chemical Society & US Natl. Lib. of Med.

Araya-Sibija, Andrea Manela, et al., Polymorphism in Progesterone Selected References, SciFinder, Feb. 24, 2014, pp. 1-12, American Chem. Society & Natl. Lib. of Med.

Araya-Sibija, Andrea Manela, et al., Polymorphism in Progesterone, SciFinder, pp. 1-46, Feb. 24, 2014, American Chem. Society & Natl. Lib. of Med.

Archer et al., Effects of ospemifene on the female reproductive and urinary tracts: translation from preclinical models into clinical evidence, Menopause: The Journal of the North American Menopause Society, vol. 22, No. 77, pp. 1-11 (2015).

Archer et al., Estrace® vs Premarin® for Treatment of Menopausal Symptoms: Dosage Comparison Study, Advances in Therapy®, vol. 9 No. 1, Jan./Feb. 1992.

Ashburn et al., Cardiovascular, Hepatic and Renal Lesions in Mice Receiving Cortisone, Estrone and Progesterone, Yale J Bilogy and Medicine, vol. 35, Feb. 1963, pp. 329-340.

Azeem, Adnan et al., Microemulsions as a Surrogate Carrier for Dermal Drug Delivery, Drug Development and Industrial Pharmacy, May 2000, vol. 35, No. 5, pp. 525-547 (abstract only). http://informahealthcare.com/doi/abs/10.1080/03639040802448646.

Azure Pharma, Inc., ELESTRIN™—Estradiol Gel, Drug Info, http://dailymed.nlm.nih.gov/dailymed/archives/fdaDrugInfo.cfm?archiveid=11885, 26 pages, Aug. 2009.

Bakhmutova-Albert, Ekaterina, et al., Enhancing Aqueous Dissolution Rates of Progesterone via Cocrystallization, SSCI, Division of Aptuit, Poster No. R6247, West Lafayette.

Banerjee, Sila, et al., On the Stability of Salivary Progesterone Under Various Conditions of Storage, Steroids, vol. 46(6), pp. 967-974, Dec. 1985.

Barnett, Steven M, Pressure-tuning infared and solution Raman spectroscopic studies of 17B-estradiol and several A-ring . . . , Vibrational Spectroscopy 8, Elsevier, pp. 263, 1995.

Bartosova, Transdermal Drug Delivery In Vitro Using Diffusion Cells, Current Medicinal Chemistry, 2012, 19, 4671-4677, Bentham Science Publishers.

Benbow et al., Distribution and Metabolism of Maternal Progesterone in the Uterus, Placenta, and Fetus during Rat Pregnancy, Biology of Reproduction 52, 1327-1333 (1995).

Bernabei, M.T., et al., Release of progesterone polymorphs from dimethylpolysiloxane polymeric matrixes, Bollettino Chimico Farmaceutico, vol. 122(1) pp. 20-26, 1983 SciFinder.

Bhavnani Bhagu R. et al., "Misconception and Concerns about Bioidentical Hormones Used for Custom-Compounded Hormone Therapy," J Clin Endocrinol Metab, Mar. 2012, 97(3):756-759.

(56) References Cited

OTHER PUBLICATIONS

Bhavnani et al., Structure Activity Relationships and Differential Interactions and Functional Activity of Various Equine Estrogens Mediated via Estrogen Receptors (ERs) ERα and ERβ, Endocrinology, Oct. 2008, 149(10):4857-4870.
Bhavnani, B.R., Stanczyk, F.Z., Pharmacology of conjugated equine estrogens: Efficacy, safety and mechanism of action, J. Steroid Biochem. Mol. Biol. (2013), Elsevier.
Bhavnani, B.R., Stanczyk, F.Z., Use of medroxyprogesterone acetate for hormone therapy in postmenopausal women: Is it safe? J. Steroid Biochem. Mol. Biol. (2013), Elsevier.
BioMed Central, Solubility of Progesterone in Organic Solvents, Online PDF, http://www.biomedcentral.com/content/supplementary/1475-2859-11-106-S2.pdf.
Blake et al., Single and multidose pharmacokinetic study of a vaginal micronized progesterone insert (Endometrin) compared with vaginal gel in healthy reproductiveaged female subjects, Fertility and Sterility# vol. 94, No. 4, Sep. 2010, Elsevier.
Borka, Laszlo, Crystal Polymorphism of Pharmaceuticals, Acta Pharm. Jugosl., vol. 40 pp. 71-94, 1990.
Brinton, L.A., Felix, A.S., Menopausal hormone therapy and risk of endometrial cancer, J. Steroid Biochem. Mol. Biol. (2013), Elsevier.
British Pharmacocopoeia 2014 Online, Refined Maize Oil, Ph. Eur. Monograph 1342, vol. I & II, Monographs: Medicinal and Pharmaceutical Substances, http://www.pharmacopoeia.co.uk/bp2014/ixbin/bp.cgi?a=print&id=7400&tab=a-z%20index [Feb. 3, 2014 1:37:50 PM].
Burry, Kenneth A, Percutaneous absorption of progesterone in postmenopausal women treated with transdermal estrogen, Am J Obstet Gynecol, vol. 180(6) part 1, pp. 1504-1511, 1999.
Busetta, Par Bernard, Structure Cristalline et Moleculair de l'Oestradiol Hemihydrate, Acta Cryst., B28 pp. 560, 1972, Bis(dimethyl-o-thiolophenylarsine)palladium(II).
Busetta, Par Bernard, Structure Cristalline et Moleculaire du Complexe Oestradiol-Propanol, Acta Cryst., B28 pp. 1349, 1972, J.A. Kanters and J. Kroon.
Campsteyn, Par H, et al., Structure Cristalline et Molcculaire de la Progesterone C21H30O2, Acta Cryst., B28 pp. 3032-3042, 1972.
Cendejas-Santana, G, et al., Growth and characterization of progesterone crystallites, Revista Mexicana de Fisica, 50, Suplemento 1 pp. 1-3, 2004.
ChemPro, Top-Notch Technology in Production of Oils and Fats, Chempro-Edible-Oil-Refining-ISO-TUV-Austria.
Christen et al., Phase I/Pharmacokinetic Study of High-Dose Progesterone and Doxorubicin, J Clin Oncol 11:2417-2426, 1993.
Christensson et al., Limonene hydroperoxide analogues differ in allergenic activity, Contact Dermatitis 2008:59: 344-352.
Christensson et al., Limonene hydroperoxide analogues show specific patch test reactions, Contact Dermatitis, 70, 291-299, 2014.
Christensson et al., Positive patch test reactions to oxidized limonene: exposure and relevance, Contact Dermatitis, 71, 264-272, 2014.
Chun et al., Transdermal Delivery of Estradiol and Norethrindrone Acetate: Effect of Vehicles ..., J. Kor. Pharm. Sci., vol. 35, No. 3, pp. 173-177 (2005).
Cicinelli et al., Direct Transport of Progesterone From Vagina to Uterus, Obstetrics & Gynecology, Vol. 95, No. 3, Mar. 2000, pp. 403-406.
Cole, Wayne & Julian, Percy L, Sterols. I. A Study of the 22-Ketosteroids, Cont. of the Research Lab. of the Glidden Co., Soya Prod. Div., vol. 67 pp. 1369-1375, Aug. 1945, Chicago.
Committee Opinion, Incidentally Detected Short Cervical Length, Committee of Obstetric Practice, Obstetrics & Gynecology, ACOG, vol. 119, No. 4, Apr. 2012, pp. 879-882.
Commodari, Fernando, Comparison of 17β-estradiol structures from x-ray diffraction and solution NMR, Magn. Reson. Chem., vol. 43, pp. 444-450, 2005, Wiley InterScience.
Cooper, A, et al., Systemic absorption of progesterone from Progest cream in postmenopausal women, The Lancet, vol. 351, pp. 1255-1256, Research Letters, Apr. 25, 1998.

Corbett et al., "Trends in Pharmacy Compounding for Women's Health in North Carolina: Focus on Vulvodynia," Southern Medical Journal, vol. 107, No. 7, Jul. 2014, pp. 433-436.
Corn Refiners Association, Corn Oil, 5th Edition, Washington, D.C., 2006.
Critchley et al., Estrogen Receptor β, But Not Estrogen Receptor α, Is Present in the Vascular Endothelium of the Human and Nonhuman Primate Endometrium, The Journal of Clinical Endocrinology & Metabolism, 2001, vol. 86, No. 3, pp. 1370-1378.
Dauqan, Eqbil M. A., et al., Fatty Acids Composition of Four Different Vegetable Oils (Red Palm Olein, Palm Olein, Corn Oil, IPCBEE, vol. 14, 2011, IACSIT Press, Singapore.
Dideberg, O, et al., Crystal data on progesterone (C21H30O2), desoxycorticosterone (C21H30O3), corticosterone (C21H30O4) and aldosterone ..., J. Appl. Cryst. vol. 4 pp. 80, 1971.
Diramio, Jackie A., Polyethylene Glycol Methacrylate/Dimetacrylate Hydrogels for Controlled Release of Hydrophobic Drugs, Masters of Science Thesis, University of Georgia, Athens, Georgia, 2002, 131 pages.
Drakulic, Branko J, Role of complexes formation between drugs and penetration enhancers in transdermal ..., Inter. Journal of Pharmaceutics, Elsevier, vol. 363, pp. 40-49, 2009.
Du et al., Percutaneous progesterone delivery via cream or gel application in postmenopausal women: a randomized cross-over study of progesterone levels in serum, whole blood, saliva, and capillary blood, Menopause: The Journal of the North American Menopause Society, 2013, vol. 20, No. 11, pp. 1-7.
Duax, William L, et al., Conformation of Progesterone Side Chain: Conflict between X-ray Data and Force-Field Calculations, J. Am. Chem. Soc., vol. 103 pp. 6705-12, Jun. 1981.
Duclos, R, et al., Polymorphism of Progesterone: Influence of the carrier and of the solid dispersion manufacturing ..., J. Thermal Anal., vol. 37 pp. 1869-1875, 1991, Wiley.
Ebian, A.R., Ebian Article: Polymorphism and solvation of ethinyl estradiol, SciFinder, Pharmaceutica Acta Helvetiae, vol. 54(4), pp. 111-114, 1979, Alexandria, Egypt.
Eisenberger, A., Westhoff, C., Hormone replacement therapy and venous thromboembolism, J. Steroid Biochem. Mol. Biol. (2013), Elsevier.
Engelhardt et al., Conceptus Influences the Distribution of Uterine Leukocytes During Early Porcine Pregnancy, Biology of Reproduction 66, 1875-1880 (2002).
Estradiol, The Merck Index Online, Royal Society of Chemistry, https://www.rsc.org/Merck-Index/monograph/mono1500003758/estradiol?q=unauthorize.
Ettinger et al., Comparison of endometrial growth produced by unopposed conjugated estrogens or by micronized estradiol in postmenopausal women, Am J Obstet Gynecol 1997; 176:112-117.
Excipients for Pharmaceuticals, Sasol Olefins & Surfactants GmbH, 2010, 28 pages.
Faassen, Fried, Physicochemical Properties and Transport of Steroids across Caco-2 Cells, Pharmaceutical Research, vol. 20(2), 2003, Plenum Pub. Corp.
FDA, Draft Guidance on Progesterone, Recommended Apr. 2010, Revised Feb. 2011 http://www.fda.gov/downloads/Drugs/GuidanceComplianceRegulatoryInformation/Guidances/UCM209294.pdf.
Ferrari, Roseli AP., et al., Oxidative Stability of Biodiesel From Soybean Oil Fatty Acid Ethyl Esters, Sci. Agric., vol. 62(3), pp. 291-295, 2005, PiracicaB1, Braz.
Filipsson et al., Concise International Chemical Assessment Document 5: Limonene, first draft, World Health Organization, Geneva, 1998, 36 pages.
Final Report on the Safety Assessment of BHT, International Journal of Toxicology, 21(Suppl. 2):19-94, 2002.
Flyvholm, Sensitizing risk of butylated hydroxytoluene B1sed on exposure and effect data, Contact Dermatitis 1990: 23: 341-345.
Fotherby, K., Bioavailability of Orally Administered Sex Steroids Used in Oral Contraception and Hormone Replacement Therapy, Contraception, 1996; 54:59-69.

(56) References Cited

OTHER PUBLICATIONS

Franklin et al., Characterization of immunoglobulins and cytokines in human cervical mucus: influence of exogenous and endogenous hormones, Journal of Reproductive Immunology 42 (1999) 93-106, Elsevier.
Franz et al., Use of Excised Human Skin to Assess the Bioequivalence of Topical Products, Skin Pharmacol Physiol 2009;22:276-286.
Freedman, R.R., Menopausal hot flashes: Mechanisms, endocrinology, treatment, J. Steroid Biochem. Mol. Biol.(2013), Elsevier.
Fuchs et al., The Effects of an Estrogen and Glycolic Acid Cream on the Facial Skin of Postmenopausal Women: A Randomized Histologic Study, Cutis. Jun. 2003;71(6):481-8.
Fugh-Berman, Adriane, Bioidentical Hormones for Menopausal Hormone Therapy: Variation on a Theme, Journal of General Internal Medicine, vol. 22, pp. 1030-1034, 2007.
Furness et al., Hormone therapy in postmenopausal women and risk of endometrial hyperplasia (Review), 2012, pp. 1-204, The Cochrane Collaboration. Published by John Wiley & Sons, Ltd.
Gäfvert et al., Free radicals in antigen formation: reduction of contact allergic response to hydroperoxides by epidermal treatment with antioxidants, British Journal of Dermatology 2002; 146: 649-656.
Ganam-Quintanar et al., Evaluation of the transepidermal permeation of diethylene glycol monoethyl ether and skin water loss, International Journal of Pharmaceutics, vo. 147, No. 2, Feb. 28, 1997, pp. 165-171 (abstract only).
Gattefossé SAS, Material Safety Data Sheet, Gelot 64, 2012, 8 pages.
Gattefossé SAS, Regulatory Data Sheet, Gelot 64, 2012, 6 pages.
Gattefossé SAS, Regulatory Data Sheet, Lauroglycol 90, 2012, 5 pages.
Gattefossé, "Excipients for Safe and Effective Topical Delivery, Drug Development and Delivery" Jul./Aug. 2012, http://drug-dev.com/Main/B1ck-Issues/Transdermal-Topical-Subcutaneous-Noninvasive-Deliv-5.aspx#.
Geelen, Math J.H. et al., "Dietary medium-chain fatty acids raise and (n-3) polyunsaturated fatty acids lower hepatic triacylglycerol synthesis in rats," The Journal of Nutrition, 1995, 125(10):2449-2456.
Gillet et al., Induction of amenorrhea during hormone replacement therapy: optimal micronized progesterone dose. A multicenter study, Maturitas 19 (1994) 103-115.
Giron-Forest, D, et al., Thermal analyis methods for pharmacopoeial materials, J. Pharmaceutical & Biomedical Anal., vol. 7(12) pp. 1421-1433, 1989, Pergamon Press, Gr. Britain.
Giron-Forest, D, Thermal analysis and calorimetric methods in the characterisation of polymorphs and solvates, Thermochimica Acta, vol. 248 pp. 1-59, 1995, Elsevier.
Glaser et al, Pilot Study: Absorption and Efficacy of Multiple Hormones Delivered in a Single Cream Applied to the Mucous Membranes of the Labia and Vagina, Gynecol Obstet Invest 2008;66:111-118.
Golatowski et al., Comparative evaluation of saliva collection methods for proteome analysis, Clinica Chimica Acta 419 (2013) 42-46.
Graham et al, Physiological Action of Progesterone in Target Tissues, Endocrine Reviews, 1997, vol. 18, No. 4, pp. 502-519.
Groothuis et al., Estrogen and the endometrium: lessons learned from gene expression profiling in rodents and human, Human Reproduction Update, vol. 13, No. 4 pp. 405-417, 2007.
Gunstone, Frank D, et al., Vegetable Oils in Food Technology: Composition, Properties and Uses, Blackwell Publishing, CRC Press, 2002.
Gurney, E.P. et al., The Women's Health Initiative trial and related studies: 10 years later: A clinician's view, J.Steroid Biochem. Mol. Biol. (2013), Elsevier.
Hamid et al., The effects of common solubilizing agents on the intestinal membrane B1rrier functions and membrane toxicity in rats, International Journal of Pharmaceutics 379 (2009) 100-108, Elsevier.
Haner, Barbara, Crystal data (I) for some pregnenes and pregnadienes, Acta Cryst., vol. 17 pp. 1610, 1964.

Hapgood, J.P., et al., Potency of progestogens used in hormonal therapy: Toward understanding differential actions, J. Steroid Biochem. Mol. Biol. (2013), Elsevier.
Hargrove et al., Menopausal Hormone Replacement Therapy with Continuous Daily Oral Micronize Estradiol and Progesterone, Obstet Gynecol, vol. 73, No. 4, Apr. 1989, pp. 606-612.
Hatton et al., "Safety and efficacy of a lipid emulsion containing medium-chain triglycerides," Clinical Pharmacy, 1990, vol. 9, No. 5, pp. 366-371.
He et al., Apoptotic Signaling Pathways in Uteri of Rats with Endometrial Hyperplasia Induced by Ovariectomy Combined with Estrogen, Gynecol Obstet Invest 2013;76:51-56.
Helbling, Ignacio M, et al., The Optimization of an Intravaginal Ring Releasing Progesterone Using a Mathematical Model, Pharm Res, vol. 31 pp. 795-808, 2014, Springer Science.
Helmy et al., Estrogenic Effect of Soy Phytoestrogens on the Uterus of Ovariectomized Female Rats, Clinic Pharmacol Biopharmaceut, 2014, S2, 7 pages.
Henderson, V.W., Alzheimer's disease: Review of hormone therapy trials and implications for treatment and prevention after . . . , J. Steroid Biochem. Mol. Biol. (2013), Elsevier.
Henriksen, Thormod, et al., An ENDOR Sturdy of Radiation-Induced Molecular Damage to Progesterone, Jour. of Mag. Resonance, vol. 63, pp. 333-342, 1985, Acedemic Press, Inc.
Herman, Anna et al., "Essential oils and their constituents as skin penetration enhancer for transdermal drug delivery: a review," 2014 Royal Pharmaceutical Society, Journal of Pharmacy and Pharmacology, pp. 1-13.
Hodis, H.N., Mack, W.J., Hormone replacement therapy and the association with heart disease and overall mortality: Clinical . . . , J. Steroid Biochem. Mol. Biol. (2013), Elsevier.
Hospital, Michel, et al., X-ray Crystallography of Estrogens and Their Binding to Receptor Sites, Mol. Pharmacology, vol. 8 pp. 438-445, Acedemic Press, Inc., 1972.
Hostynek, JJ, Predictinga bsorptiono f fragrancec hemicalst hrough human skin, j. Soc.C osmeCt. hem.,4 6, 221-229 (Jul./Aug. 1995).
Hulsmann, Stefan, Stability of Extruded 17B-Estradiol Solid Dispersions, Pharmaceutical Development and Tech., vol. 6(2) pp. 223-229, 2001, Marcel Dekker, Inc.
Hurn et al., Estrogen as a Neuroprotectant in Stroke, Journal of Cerebral Blood Flow and Metabolism 20:631-652, 2000, Lippincott Williams & Wilkins, Inc., Philadelphia.
Hyder et al., Synthetic Estrogen 17a-Ethinyl Estradiol Induces Pattern of Uterine Gene Expression Similar to Endogenous Estrogen 17β-Estradiol, JPET 290(2):740-747, 1999.
Idder, Salima, et al., Physicochemical properties of Progesterone, SciFinder, pp. 1-26, Feb. 24, 2014, American Chem. Society & US Natl. Lib. of Med.
ISR (App. No. PCT/US12/66406).
ISR (App. No. PCT/US13/023309).
ISR and written opinion for PCT/US/13/46442, dated Nov. 1, 2013.
ISR and written opinion for PCT/US/13/46443, dated Oct. 31, 2013.
ISR and written opinion for PCT/US/13/46444, dated Oct. 31, 2013.
ISR and written opinion for PCT/US/13/46445, dated Nov. 1, 2013.
Johanson, Gunnar, Toxicity Review of Ethylene Glycol Monomethyl Ether and its Acetate Ester, Critical Reviews in Toxicology, 2000, vol. 30, No. 3, pp. 307-345 (abstract only). http://informahealthcare.com/doi/abs/10.1080/10408440091159220.
Johnson, William S, et al., Racemic Progesterone, Tetrahedron Letters No. 4, pp. 193-196, 1963, Pergamon Press Ltd., Great Britain.
Joshi et al., Detection and synthesis of a progestagen-dependent protein in human endometrium, J Reprod Fert (1980) 59, 273-285.
Kanno et al., The OECD Program to Validate the Rat Uterotrophic Bioassay to Screen Compounds for in Vivo Estrogenic Responses: Phase 1, Environmental Health Perspectives • vol. 109 | No. 8 | Aug. 2001, pp. 785-794.
Karlberg et al., Air oxidation of d-limonene (the citrus solvent) creates potent allergens, Contact Dermatitis, 1992: 26: 332-340.
Karlberg et al., Influence of an anti-oxidant on the formation of allergenic compounds during auto-oxication of d-limonene, Ann. Occup. Hyg., vol. 38, No. 2, pp. 199-207, 1994.

(56) References Cited

OTHER PUBLICATIONS

Kaunitz, Andrew M., Extended duration use of menopausal hormone therapy, Menopause: The Journal of the North American Menopause Society, 2014, vol. 21, No. 6, pp. 1-3.

Khalil, Sah, Stability and Dissolution Rates of Corticosteroids in Polyethylene Glycol Solid Dispersions, Drug Dev. & Indus. Pharm., vol. 10(5) pp. 771-787, 1984, Marcel Dekker.

Kharode et al., The Pairing of a Selective Estrogen Receptor Modulator, Blzedoxifene, with Conjugated Estrogens as a New Paradigm for the Treatment of Menopausal Symptoms and Osteoporosis Prevention, Endocrinology 149(12):6084-6091, 2008.

Kim et al., Safety Evaluation and Risk Assessment of d-Limonene, Journal of Toxicology and Environmental Health, Part B: Critical Reviews, 2013, 16:1, 17-38 http://dx.doi.org/10.1080/10937404.2013.769418.

Kincl et al., Increasing Oral Bioavailability of Progesterone by Formulation, Journal of Steroid Biochemistry, 1978, vol. 9, pp. 83-84.

Knuth et al., Hydrogel delivery systems for vaginal and oral applications: Formulation and biological considerations, Advanced Drug Delivery Reviews, vol. 11, No. 1-2, Jul.-Aug. 1993, pp. 137-167 (abstract only).

Koga et al., Enhancing mechanism of Labrasol on intestinal membrane permeability of the hydrophilic drug gentamicin sulfate, European Journal of Pharmaceutics and Biopharmaceutics 64 (2006) 82-91.

Komm et al., Blzedoxifene Acetate: A Selective Estrogen Receptor Modulator with Improved Selectivity, Endocrinology 146(9):3999-4008, 2005.

Korkmaz, Filiz, Byophysical Studies of Progesterone-Model Membrane Interactions, Thesis, Grad. School of Nat. and App. Sci. of the Middle East Tech. University, Sep. 2003.

Kotiyan, P.N., Stability indicating Hptlc method for the estimation of estradiol, Journal of Pharmaceutical and Biomedical Analysis, vol. 22 pp. 667-671, 2000, Elsevier.

Krzyminiewski, R, et al., EPR Study of the Stable Radical in a y-Irradiated Single Crystal of Progesterone, Jour. of Mag. Resonance, vol. 46 pp. 300-305, 1982, Acedemic Press.

Kubli-Garfias, C, et al., Ab initio calculations of the electronic structure of glucocorticoids, Jour. of Mol. Structure, Theochem, vol. 454 pp. 267-275, 1998, Elsevier.

Kubli-Garfias, Carlos, Ab initio study of the electronic structure of progesterone and related progestins, Jour. of Mol. Structure, Theochem vol. 425, pp. 171-179, 1998, Elsevier (abstract only).

Kuhnert-Brandstaetter and Grimm. Zur Unterscheidung von losungsmittelhaltigen pseudopolymorphen Kristallformen and polymorphen Modifikationen bei Steroidhormonen.II, Mikrochimica Acta, vol. 1, pp. 127-139, 1968.

Kuhnert-Brandstaetter and Junger and Kofler. Thermo-microscopic and spectrophotometric: Determination of steroid hormones, Microchemical Journal 9, pp. 105-133, 1965.

Kuhnert-Brandstaetter and Kofler. Zur mikroskopischen Identitatsprufung and zur Polymorphie der Sexualhormone, Mikrochimica Acta, vol. 6, pp. 847-853, 1959.

Kuhnert-Brandstaetter and Linder. Zur Hydratbildung bei Steroidhormonen, Sci. Pharm, vol. 41(2), pp. 109-116, 1973.

Kumasaka et al., Effects of Various Forms of Progestin on the the Estrogen-Primed, Ovariectomized Rat, Endocrine Journal 1994, 41(2), 161-169.

Kuon et al., A Novel Optical Method to Assess Cervical Changes during Pregnancy and Use to Evaluate the Effects of Progestins on Term and Preterm Labor, Am J Obstet Gynecol. Jul. 2011; 205(1): 82.e15-82.e20.

Kuon et al., Actions of progestins for the inhibition of cervical ripening and uterine contractions to prevent preterm birth, FVV in OBGYN, 2012, 4 (2): 110-119.

Kuon et al., Pharmacological actions of progestins to inhibit cervical ripening and prevent delivery depend upon their properties, the route of administration and the vehicle, Am J Obstet Gynecol. May 2010; 202(5): 455.e1-455.e9.

Labrie, et al., Intravaginal prasterone (DHEA) provides local action without clinically significant changes in serum concentrations of estrogens or androgens, Journal of Steroid Biochemistry & Molecular Biology, vol. 138, pp. 359-367, 2013, Elsevier.

Lacey, J.V. Jr., The WHI ten year's later: An epidemiologist's view, J. Steroid Biochem. Mol. Biol. (2013), Elsevier.

Lahiani-Skibl, Malika, Solubility and Dissolution Rate of Progesterone-Cyclodextrin..., Drug Development and Industrial Pharmacy, Informa Healthcare vol. 32, pp. 1043-1058, 2006.

Lancaster, Robert W, et al., The Polymorphism of Progesterone: Stabilization of a 'Disappearing' Polymorph by..., Jour. of Pharm. Sci., vol. 96(12) pp. 3419-3431, 2007, Wiley-Liss.

Land, Laura M, The influence of water content of triglyceride oils on the solubility of steriods, Pharmaceutical Research, vol. 22(5) May 2005, Springer Science+Business Media.

Lauer et al., "Evaluation of the hairless rat as a model for in vivo percutaneous absorption," Journal of Pharmaceutical Sciences, vol. 86, No. 1, Jan. 1997, pp. 13-18.

Leonetti et al., Transdermal progesterone cream as an alternative progestin in hormone therapy, Alternative Therapies, Nov./Dec. 2005, vol. 11, No. 6, pp. 36-38.

Leonetti, Helene B, et al., Topical progesterone cream has an antiproliferative effect on estrogen-stimulated endometrium, Fertility and Sterility, vol. 79(1), Jan. 2003.

Lewis, John G. et al., Caution on the use of saliva measurements to monitor absorption of progesterone from transdermal creams in postmenopausal women, Maturitas, The European Menopause Journal, vol. 41, pp. 1-6, 2002.

Li, Guo-Chian, Solid-state NMR analysis of steroidal conformation of 17a- and 17B-estradiol in the absence and presence of lipi..., Steroids, Elsevier, vol. 77, pp. 185-192, 2012.

Lobo, R.A., Foreword, J. Steroid Biochem. Mol. Biol. (2014), Elsevier.

López-Belmonte, Corrigendum to "Comparative uterine effects on ovariectomized rats after repeated treatment with different vaginal estrogen formulations" [Maturitas 72 (2012) 353-358], Maturitas 74 (2013) 393, Elsevier.

Lucy et al., Gonadotropin-releasing hormone at estrus: lutenizing hormone, estradiol, and progesterone during... Biol Reprod Sep. 1986;35(2):300-311 (abstract only).

Lvova, M. SH., et al., Thermal Analysis in the Quality Control and Standardization of Some Drugs, J Thermal Anal., vol. 40 pp. 405-411, 1993, Wiley.

Madishetti et al., Development of domperidone bilayered matrix type transdermal patches: physicochemical, in vitro and ex vivo characterization, DARU vol. 18, No. 3, 2010, pp. 221-229.

Magness, R.R., et al., Estrone, Estradiol-17β and Progesterone Concentrations in Uterine Lymph and Systematic Blood throughout the Porcine Estrone Estrous Cycle, Journal of Animal Science, vol. 57, pp. 449-455, ISU, 1983.

Manson, JoAnn E. et al., "Menopausal hormone therapy and health outcomes during the intervention and extended poststoping phases of the women's health initiative randomized trials," JAMA, Oct. 2, 2013, vol. 310, No. 13, pp. 1353-1368.

McGuffy, Irena, Softgel Technology as a Lipid-B1sed Delivery Tool for Bioavailability Enhancement, Catalent Pharma Solutions, Somerset, NJ, Mar. 2011.

Mesley, R.J., Clathrate Formation from Steroids, Chemistry and Industry, vol. 37 pp. 1594-1595, Sep. 1965.

Miao, Wenbin, et al., Chemical Properties of Progesterone, SciFinder, 2014, American Chemical Society & US Natl. Lib. of Med.

Miles et al., Pharmacokinetics and endometrial tissue levels of progesterone after administration bv'Intramuscular and vaginal routes: a comparative study, Fertility and Sterility, vol. 62, No. 3, Sep. 1994, pp. 485-490.

Miller et al., Safety and Feasibility of Topical Application of Limonene as a Massage Oil to the Breast, Journal of Cancer Therapy, 2012, 3, 749-754.

Mueck, A.O. et al., Genomic and non-genomic actions of progestogens in the breast, J. Steroid Biochem. Mol.Biol. (2013), Elsevier.

(56) References Cited

OTHER PUBLICATIONS

Muramatsu, Mitsuo, Thermodynamic Relationship between a- and B-Forms of Crystalline Progesterone, J. Pharmaceutical Sciences, vol. 68(2) pp. 175-178, 1979, Amer. Pharm. Assoc.

Ng, Jo-Han et al., Advances in biodiesel fuel for application in compression ignition engines, Clean Techn Environ Policy, vol. 12, pp. 459-493, 2010, Springer-Verlag.

Nicklas, Martina, Preparation and characterization of marine sponge collagen nanoparticles and employment for the trans . . . , Drug Devel. & Indust. Pharmacy,35(9) pp. 1035, 2009.

Nilsson et al., Analysis of Contact Allergenic Compounds in Oxidized d-Limonene, Chromatographia vol. 42, No. 3/4, Feb. 1996, pp. 199-205.

Notelovitz, Morris, et al., Initial 17-b-Estradiol Dose for Treating Vasomotor Symptoms, Obstetrics & Gynecology, vol. 95(5), pp. 726-731, part 1, May 2000, Elsevier.

NuGen, What is NuGen HP Hair Growth System.

NuGest900, NuGest 900™.

O'Leary, Peter, Salivary, but not serum or urinary levels of progesterone are elevated after topical application of pregersterone cream to pre-and post-menopausal women, Clinical Endocrinology, vol. 53 pp. 615-620, Blackwell Science 2000.

Opinion on the Diethylene Glycol Momoethyl Ether (DEGEE), Scientific Committee on Consumer Products, Dec. 19, 2006, 27 pages.

Outterson, K., The Drug Quality and Security Act—Mind the Gaps, n engl j med 370;2 nejm.org Jan. 9, 2014, pp. 97-99.

Palamakula et al., Preparation and In Vitro Characterization of Self-Nanoemulsified Drug Delivery Systems of Coenzyme Q10 Using Chiral Essential Oil Components, Pharmaceutical Technology Oct. 2004, pp. 74-88.

Panay et al., The 2013 British Menopause Society & Women's Health Concern recommendations on hormone replacement therapy, Menopause International: The Integrated Journal of Postreproductive Health, published online May 23, 2013, Sage Publications. http://min.sagepub.com/content/early/2013/05/23/1754045313489645.1.

Panchangnula et al., Development and evaluation of an intracutaneous depot formulation of corticosteroids using Transcutol . . . , J Pharm Pharmacol. Sep. 1991;43(9):609-614 (abstract only).

Parasuraman et al., Blood sample collection in small laboratory animals, Journal of Pharmacology & Pharmacotherapeutics | Jul.-Dec. 2010 | vol. 1 | Issue 2, pp. 87-93.

Park, Jeong-Sook, Solvent effects on physicochemical behavior of estradiols recrystalized for transdermal delivery, Arch Pharm Res, vol. 31(1), pp. 111-116, 2008.

Park, Jeong-Sook, Use of CP/MAS solid-state NMR for the characterization of solvate . . . , European Journal of Pharmaceutics and Biopharmaceutics, vol. 60, pp. 407-412, 2005.

Parrish, Damon A., A new estra-1,3,5(10)-triene-3,17b-diol solvate: estradiol-methanol-water, Crystal Structure Comm., Intn'l Union of Crystallography, ISSN 0108-2701, 2003.

Patel et al., Transdermal Drug Delivery System: A Review, www.thepharmajournal.com, vol. 1, No. 4, 2012, pp. 78-87.

Payne, R.S., et al., Examples of successful crystal structure prediction: polymorphs of primidone and progesterone, Intl. Jour. of Pharma., vol. 177 pp. 231-245, 1999, Elsevier.

PCCA, Apothogram, PCCA, May 2014, Houston, TX.

Persson, Linda C, et al., Physicochemical Properties of Progesterone Selecte, SciFinder, pp. 1-5, Feb. 24, 2014, American Chem. Society & US Natl. Lib. of Med.

Pfaus et al., Selective facilitation of sexual solicitation in the female rat by a melanocortin receptor agonist, PNAS, Jul. 6, 2004, vol. 101, No. 27, pp. 10201-10204.

Pheasant, Richard, Polymorphism of 17-Ethinylestradiol, Schering Corporation, Bloomfield, NJ, May 1950.

Pickles, VR, Cutaneous reactions to injection of progesterone solutions into the skin, Br Med Journal, Aug. 16, 1952, pp. 373-374.

Pinkerton et al., What are the concerns about custom-compounded "bioidentical" hormone therapy? Menopause: The Journal of The North American Menopause Society, vol. 21, No. 12, 2014,pp. 1-3.

Pinkerton, J.V., Thomas, S., Use of SERMs for treatment in postmenopausal women, J. Steroid Biochem. Mol. Biol. (2014), Elsevier.

Pisegna, Gisia L, A High-pressure Vibrational Spectroscopic Study of Polymorphism in Steroids . . . , Thesis, McGill University, Dept. of Chem, Nov. 1999, Natl. Lib. of Canada.

Portman, David et al., One-year treatment persistence with local estrogen therapy in postmenopausal women diagnosed as having vaginal atrophy, Menopause, vol. 22, No. 11, 2015, pp. 000/000 (8 pages).

Position Statement, Management of symptomatic vulvovaginal atrophy: 2013 position statement of the North American Menopause Society (NAMS), Menopause, vol. 20, No. 9, pp. 888-902.

Practice Bulletin No. 141, Management of Menopausal Symptoms, Obstetrics & Gynecology, ACOG, vol. 123, No. 1, Jan. 2014, pp. 202-216.

Prajapati, Hetal N, et al., A comparative Evaluation of Mono-, Di- and Triglyceride of Medium Chain Fatty Acids by Lipid/Surfactant/Water, Springerlink.com, pp. 1-21, Apr. 2011.

Prausnitz et al., Transdermal drug delivery, Nat Biotechnol. Nov. 2008 ; 26(11): 1261-1268.

Price, Sarah L, The computational prediction of pharmaceutical crystal structures and polymorphism, Adv. Drug Delivery Reviews, vol. 56 pp. 301-319, 2004, Elsevier.

Product Information Sheet, Body Bl1ance Cream, Tahitian Noni International, 2013, 1 page.

Product Safety Assessment: Diethylene Glycol Monoethyl Ether, Created: Sep. 24, 2007 The Dow Chemical Company Page, 5 pages.

Progesterone, The Merck Index Online, Royal Society of Chemistry, 2013, search Feb. 17, 2014 https://www.rsc.org/Merck-Index/monograph/print/mono1500007889/progesterone?q=authorize.

Progynova TS 100, available online at file:///C:/Users/Call%20Family/Desktop/Progynova%20TS%20100%2012%20Patches_Pack%20%28Estradiol%20Hemihydrate%29.html, 2010.

Provider Data Sheet, About Dried Blood Spot Testing, ZRT Laboratory, 2014, 3 pages.

Rahn et al., Vaginal Estrogen for Genitourinary Syndrome of Menopause A Systematic Review, Obstet Gynecol 2014;124(6):1147-56.

Rao, Rajeswara et al., "Intra Subject Variability of Progesterone 200 mg Soft Capsules in Indian Healthy Adult Postmenopausal Female Subjects under Fasting Conditions," J Bioequiv Availab. 2014, 6: 139-143.

Reisman et al., Topical Application of the Synthetic Triterpenoid RTA 408 Protects Mice from Radiation-Induced Dermatitis, Radiation Research 181, 512-520 (2014).

Rosilio, V, et al., Physical Aging of Progesterone-Loaded Poly(D,L,-lactide-co-glycolide) Microspheres, Pharmaceutical Research, vol. 15(5) pp. 794-799,1998, Plenum Pub. Corp.

Ross et al., Randomized, double-blind, dose-ranging study of the endometrial effects of a vaginal progesterone gel in estrogen-treated postmenopausal women, AnnJ Obstet Gynecol, Oct. 1997, vol. 177, No. 4, pp. 937-941.

Ruan et al., Systemic progesterone therapy—Oral, vaginal, injections and even transdermal? Maturitas 79 (2014) 248-255, Elsevier.

Salem, HF, Sustained-release progesterone nanosuspension following intramuscular injection in ovariectomized rats, International Journal of Nanomedicine 2010:5 943-954, Dove Press.

Salole, Eugene G., Estradiol, Analytical Profiles of Drug Substances, vol. 15, pp. 283-318, 1986.

Salole, Eugene G., The physicochemical properties of oestradiol, Journal of Pharmaceutical & Biomedical Analysis, vol. 5, No. 7, pp. 635-648, 1987.

Santen, R.J., Menopausal hormone therapy and breast cancer, J. Steroid Biochem. Mol. Biol. (2013), Elsevier.

Santen, RJ, Vaginal administration of estradiol: effects of dose, preparation and timing on plasma estradiol levels, CLIMACTERIC 2014;17:1-14.

Sarkar, Bisu, et al., Chemical Stability of Progesterone in Compounded Topical Preparations using PLO Transdermal Cream™ and HRT Cream™ B1se . . . , J Steroids Horm Sci, 4:2, 2013.

Sarrel, et al., The Mortality Toll of Estrogen Avoidance: An Analysis of Excess Deaths Among Hysterectomized Women Aged 50 to 59

(56) References Cited

OTHER PUBLICATIONS

Years, American Journal of Public Health, Research and Practice, e1-e6. Published online ahead of print Jul. 18, 2013.
Satyanarayana, D, et al., Aqueous Solubility Predictions of Aliphatic Alcohols, Alkyl Substituted Benzoates and Steroids, Asian J. Chem., vol. 9 (3) pp. 418-426, 1997.
Scavarelli, Rosa Maria, et al., Progesterone and Hydrate or Solvate, SciFinder, pp. 1-2, Feb. 24, 2014, American Chem. Society.
Schindler, A.E., The "newer" progestogens and postmenopausal hormone therapy (HRT), J. Steroid Biochem.Mol. Biol. (2013), Elsevier.
Schindler, Aldof E. et al., Classification and pharmacology of progestins, Maturitas 46S1 (2003) S7-S16.
Schutte et al., A tissue engineered human endometrial stroma that responds to cues for secretory differentiation, decidualization and menstruation, Fertil Steril. Apr. 2012 ; 97(4): 997-1003, Elsevier.
Schweikart et al., Comparative Uterotrophic Effects of Endoxifen and Tamoxifen in Ovariectomized Sprague-Dawley Rats, Toxicologic Pathology, 42: 1188-1196, 2014.
SciFinder Scholar Prednisone Chemical Properties, SciFinder, 2014, pp. 1-7, National Library of Medicine.
SciFinder Scholar Prednisone Physical Properties, SciFinder, 2014, pp. 1-10, Natioinal Library of Medicine.
SciFinder Scholar Progesterone Experimental Properties, SciFinder, pp. 1-9, Feb. 24, 2014, American Chem. Society.
Serantoni, Foresti, et al., 4-Pregnen-3,20-dione (progesterone, form II), Crystal Structure Comm., vol. 4(1) pp. 189-192, 1975, CAPLUS DataBlse.
Shao et al., Review Open Access Direct effects of metformin in the endometrium: a hypothetical mechanism for the treatment of women with PCOS and endometrial carcinoma, Journal of Experimental & Clinical Cancer Research 2014, 33(1):41, 11 pages.
Sharma, H.C., et al., Physical Properties of Progesterone Selected Refer, SciFinder, pp. 1-5, Feb. 24, 2014, American Chem. Society & US Natl. Lib. of Med.
Shrier et al., "Mucosal Immunity of the Adolescent Female Genital Tract," Journal of Adolescent Health, 2003; 32:183-186.
Shufelt et al., Hormone therapy dose, formulation, route delivery, and risk of cardiovascular events in women: findings from the Women's Health Initiative Observational Study, Menopause: The Journal of the North American Menopause Society, vol. 21, No. 3, 2014, pp. 1-7, 2013.
Siew, Adeline, moderator, Bioavailability Enhancement with Lipid-B1sed Drug-Delivery Systems, Pharmaceutical Technology, Aug. 2014, pp. 28, 30-31.
Sigma-Aldrich, Progesterone-Water Soluble: powder, BioReagent, suitable for cell culture), MSDS available online: http://www.sigmaaldrich.com/catalog/product/sigma/p7556.
Simon et al., Effective Treatment of Vaginal atrophy with an Ultra-low-dose estradiol vaginal tablet, Obstetrics & Gynecology, vol. 112, No. 5, Nov. 2008, pp. 1053-1060.
Simon, James A., What if the Women's Health Initiative had used transdermal estradiol and oral progesterone instead? Menopause: The Journal of The North American Menopause Society, 2014, vol. 21, No. 7, pp. 1-15.
Sitruk-Ware et al., Progestogens in hormonal replacement therapy: new molecules, risks, and benefits, Menopause: The Journal of The North American Menopause Society. vol. 9, No. 1, pp. 6-15, 2002.
Sitruk-Ware, Regine, "Pharmacological profile of progestins," Maturitas 47 (2004) 277-283.
Sitruk-Ware, Regine, Oral Micronized Progesterone—Bioavailability pharmacokinetics, pharmacological and therapeutic implications—A review, Contraception, Oct. 1987, vol. 36, No. 4, pp. 373-402.
Smith et al., Lower Risk of Cardiovascular Events in Postmenopausal Women Taking Oral Estradiol Compared with Oral Conjugated Equine Estrogens, JAMA Internal Medicine, Published online Sep. 30, 2013, E1-E7. jamainternalmedicine.com.
Smyth et al., Summary of Toxicological Data, A 2-Yr Study of Diethylene Glycol Monoethyl Ether in Rats, Fd Cosmet. Toxicol. vol. 2, pp. 641-642, 1964.

Stanczyk et al., Thereaputically equivalent pharmacokinetic profile across three application sistes for AG200-15, a novel low-estrogen dose contraceptive patch, Contraception, 87 (2013) pp. 744-749.
Stanczyk, F.Z. et al., "Percutaneous administration of progesterone: blood levels and endometrial protection," Menopause: The Journal of The North American Menopause Society, 2005, vol. 12, No. 2, pp. 232-237.
Stanczyk, F.Z. et al., Ethinyl estradiol and 17β-estradiol in combined oral contraceptives: pharmacokinetics, pharmacodynamics and risk assessment, Contraception 87 (Jun. 2013) vol. 87, No. 6, pp. 706-727.
Stanczyk, F.Z., "All progestins are not created equal," Steroids 68 (2003) 879-880.
Stanczyk, F.Z., "Treatment of postmenopausal women with topical progesterone creams and gels: are they effective?" Climacteric 2014;17 (Suppl 2):8-11.
Stanczyk, F.Z., Bhavnani, B.R., Current views of hormone therapy for the management and treatment of postmenopausal women, J. Steroid Biochem. Mol. Biol. (2014), Elsevier.
Stein, Emily A, et al., Progesterone Physical Properties, SciFinder, pp. 1-46, Feb. 24, 2014, American Chem. Society & US Natl. Lib. of Med.
Stephenson et al., "Transdermal progesterone: Effects on Menopausal symptoms and on thrombotic, anticoagulant, and inflammatory factors in postmenopausal women," Int J Pharmaceutical Compounding, vol. 12, No. 4, Jul./Aug. 2008, pp. 295-304.
Strickley, Robert T., Solubilizing excipients in oral and injectable formulations, Pharmaceutical Research Feb. 2004, vol. 21, Issue 2, pp. 201-230 (abstract only).
Strocchi, Antonino, Fatty Acid Composition, and Triglyceride Structure of Corn Oil, Hydrogenated Corn Oil, and Corn Oil Margarine, Journal of Food Science, vol. 47, pp. 36-39, 1981.
Struhar, M, et al., Estradiol Benzoate: Preparation of an injection suspension . . . , SciFinder, Cesko-Slovenska Farmacie, vol. 27(6), pp. 245-249, 1978, Bratislava, Czech.
Sullivan et al., "A review of the nonclinical safety of Transcutol®, a highly purified form of diethylene glycol monoethyl ether (DEGEE) used as a pharmaceutical excipient," Food and Chemical Toxicology, 72 (2014) pp. 40-50.
Sun, Jidong, D-Limonene: Safety and Clinical Applications, Alternative Medicine Review vol. 12, No. 3, 2007, pp. 259-264.
Tait, Alex D, Characterization of the Prod. from the Oxidation of Progesterone with Osmium Tetroxide, Dept of Investigative Med., Univ. Cambridge, Gt. Britain pp. 531-542, 1972.
Takacs M. et al., The light sensitivity of corticosteroids in crystalline form, Pharmaceutica acta Helvetiae, vol. 66 (5-6) pp. 137-140, 1991, Hardin Library.
Tan, Melvin S. et al., A Sensitive Method for the Determination of Progesterone in Human Plasma by LC-MS-MS, M1025, Cedra Corporation, Austin, Texas.
Tang et al., Effect of Estrogen and Progesterone on the Development of Endometrial Hyperplasia in the Fischer Rat, Biology of Reproduction 31, 399-413 (1984).
Tas et al., Comparison of antiproliferative effects of metformine and progesterone on estrogen-induced endometrial hyperplasia in rats, Gynecol Endocrinol, Early Online: 1-4, 2013. http://informahealthcare.com/gye.
Tella, S.H., Gallagher, J.C., Prevention and treatment of postmenopausal osteoporosis, J. Steroid Biochem. Mol. Biol. (2013), Elsevier.
Thomas, Joshua, et al., The effect of water solubility of solutes on their flux through human skin in vitro: An . . . , Intl. J. of Pharmaceut., vol. 339 pp. 157-167, 2007, Elsevier.
Thomas, Peter, Characteristics of membrane progestin receptor alpha (mPRa) and progesterone membrane receptor component 1 (PGMRC1) and their roles in mediating rapid progestin actions, Frontiers in Neuroendocrinology 29 (2008) 292-312.
Tripathi, R, et al., Study of Polymorphs of Progesterone by Novel Melt Sonocrystallization Technique: A Technical Note, AAPS PhamSciTech, vol. 11, No. 3, Sep. 2010.
Trommer et al., Overcoming the stratum Corneum: The modulation of Skin Penetration, Skin Pharmacol Physiol 2006;19:106-121.
Tuleu et al., "Comparative Bioavailability Study in Dogs of a Self-Emulsifying Formulation of Progesterone Presented in a Pellet and

(56) References Cited

OTHER PUBLICATIONS

Liquid Form Compared with an Aqueous Suspension of Progesterone," Journal of Pharmaceutical Sciences, vol. 93, No. 6, Jun. 2004, pp. 1495-1502.
Ueda et al., Topical and Transdermal Drug Products, Pharmacopeial Forum, vol. 35(3) [May-Jun. 2009], 750-754.
USP, 401 Fats and Fixed Oils, Chemical Tests, Second Suplement to USP36-NF 31, pp. 6141-6151, 2013.
USP, Certificate-Corn Oil, Lot G0L404, Jul. 2013.
USP, Lauroyl Polyoxylglycerides, Safety Data Sheet, US, 5611 Version #02, pp. 1-9, 2013.
USP, Monographs: Progesterone, USP29, www.pharmacopeia.cn/v29240/usp29nf24s0_m69870.html, search done: Feb. 25, 2014.
USP, Official Monographs, Corn Oil, NF 31, pp. 1970-1971, Dec. 2013.
USP, Official Monographs, Lauroyl Polyoxylglycerides, NF 31, pp. 2064-2066, Dec. 2013.
USP, Official Monographs, Medium Chain Triglycerides, NF 31, pp. 2271-2272, Dec. 2013.
USP, Official Monographs, Mono- and Di-glycerides, NF 31, pp. 2101, Dec. 2013.
U.S. Appl. No. 12/561,515 Jan. 29, 2013 Advisory Action.
Final Office Action dated Oct. 26, 2012 in U.S. Appl. No. 12/561,515.
Notice of Allowance dated Sep. 11, 2013 in U.S. Appl. No. 12/561,515.
Office Action dated Dec. 12, 2011 in U.S. Appl. No. 12/561,515.
U.S. Appl. No. 13/684,002 Mar. 20, 2013 Non-Final Office Action.
U.S. Appl. No. 13/684,002 Jul. 16, 2013 Final Office Action.
U.S. Appl. No. 13/684,002 Dec. 6, 2013 Notice of Allowance.
U.S. Appl. No. 13/843,362 Mar. 16, 2015 Restriction Requirement.
U.S. Appl. No. 13/843,428 Apr. 14, 2015 Restriction Requirement.
U.S. Appl. No. 14/099,545 Feb. 18, 2014 Non-Final Office Action.
U.S. Appl. No. 14/099,545 Jul. 14, 2014 Notice of Allowance.
U.S. Appl. No. 14/099,562 Feb. 20, 2014 Restriction Requirement.
U.S. Appl. No. 14/099,562 Mar. 27, 2014 Non-Final Office Action.
U.S. Appl. No. 14/099,562 Jul. 2, 2014 Final Office Action.
U.S. Appl. No. 14/099,562 Dec. 10, 2014 Notice of Allowance.
U.S. Appl. No. 14/099,571 Mar. 28, 2014 Restriction Requirement.
U.S. Appl. No. 14/099,571 Jul. 15, 2014 Notice of Allowance.
U.S. Appl. No. 14/099,582 Apr. 29, 2014 Restriction Requirement.
U.S. Appl. No. 14/099,582 Jun. 17, 2014 Non-Final Office Action.
U.S. Appl. No. 14/099,582 Nov. 7, 2014 Notice of Allowance.
U.S. Appl. No. 14/099,582 Jan. 22, 2015 Notice of Allowance.
U.S. Appl. No. 14/099,598 May 13, 2014 Restriction Requirement.
U.S. Appl. No. 14/099,598 Jul. 3, 2014 Non-Final Office Action.
U.S. Appl. No. 14/099,598 Dec. 10, 2014 Notice of Allowance.
U.S. Appl. No. 14/099,612 Mar. 20, 2014 Restriction Requirement.
U.S. Appl. No. 14/099,612 Oct. 30, 2014 Non-Final Office Action.
U.S. Appl. No. 14/099,612 Nov. 26, 2014 Notice of Allowance.
U.S. Appl. No. 14/099,623 Mar. 5, 2014 Restriction Requirement.
U.S. Appl. No. 14/099,623 Jul. 18, 2014 Non-Final Office Action.
U.S. Appl. No. 14/099,623 Dec. 15, 2014 Notice of Allowance.
U.S. Appl. No. 14/103,355 Dec. 8, 2014 Non-Final Office Action.
U.S. Appl. No. 14/106,655 Jul. 3, 2014 Restriction Requirement.
U.S. Appl. No. 14/125,554 Dec. 5, 2014 Restriction Requirement.
U.S. Appl. No. 14/125,554_Apr. 14, 2015_Non-Final_Office_Action.
U.S. Appl. No. 14/136,048_Nov. 4, 2014_Restriction_Requirement.
U.S. Appl. No. 14/136,048_Mar. 12, 2015_Non-Final_Office_Action.
U.S. Appl. No. 14/475,814_Oct. 1, 2014_Non-Final_Office_Action.
U.S. Appl. No. 14/475,814_Feb. 13, 2015_Notice_of_Allowance.
U.S. Appl. No. 14/475,864_Feb. 11, 2014_Notice_of_Allowance.
U.S. Appl. No. 14/475,864_Oct. 2, 2014_Non-Final_Office_Action.
U.S. Appl. No. 14/476,040_Mar. 26, 2014_Restriction_Requirement.
U.S. Appl. No. 14/521,230_Dec. 5, 2014_Restriction_Requirement.
U.S. Appl. No. 14/521,230_Feb. 18, 2015_Non-Final_Office_Action.
Utian, Wulf H, et al., Relief of vasomotor symptoms and vaginal atrophy with lower doses of conjugated equine estrogens, Fertility and Sterility, vol. 75(6) pp. 1065, Jun. 2001.
Voegtline et al., Dispatches from the interface of salivary bioscience and neonatal research, Frontiers in Endocrinology, Mar. 2014, vol. 5, article 25, 8 pages.
Waddell et al., Distribution and metabolism of topically applied progesterone in a rat model, Journal of Steroid Biochemistry & Molecular Biology 80 (2002) 449-455.
Waddell et al., The Metabolic Clearance of Progesterone in the Pregnant Rat: Absence of a Physiological Role for the Lung, Biology of Reproduction 40, 1188-1193 (1989).
Walter et al., The role of progesterone in endometrial angiogenesis in pregnant and ovariectomised mice, Reproduction (2005) 129 765-777.
Weber, E.J., Corn Lipids, Cereal Chem., vol. 55(5), pp. 572-584, The American Assoc of Cereal Chem, Sep.-Oct. 1978.
Weber, M.T., et al., Cognition and mood in perimenopause: A systematic review and meta-analysis, J. Steroid Biochem. Mol. Biol. (2013), Elsevier.
Weintraub, Arlene, "Women fooled by untested hormones from compounding pharmacies," Forbes, Feb. 20, 2015; retrieved online at http://onforb.es/1LIUm1V on Feb. 23, 2015, 3 pages.
Whitehead et al., Absorption and metabolism of oral progesterone, The British Medical Journal, vol. 280, No. 6217 (Mar. 22, 1980), pp. 825-827, BMJ Publishing Group.
Wiranidchapong, Chutima, Method of preparation does not affect the miscibility between steroid hormone and polymethacrylate, Thermochimica Acta 485, Elsevier, pp. 57, 2009.
Wood et al., Effects of estradiol with micronized progesterone or medroxyprogesterone acetate on risk markers for breast cancer in postmenopausal monkeys, Breast Cancer Res Treat (2007) 101:125-134.
Wren et al., Effect of sequential transdermal progesterone cream on endometrium, bleeding pattern, and plasma progesterone and salivary progesterone levels in postmenopausal women, Climacteric, 2000, 3(3), pp. 155-160. http://dx.doi.org/10.1080/13697130008500109.
Wu et al., Gene Expression Profiling of the Effects of Castration and Estrogen Treatment in the Rat Uterus, Biology of Reproduction 69, 1308-1317 (2003).
Yalkowsky, Samuel H, & Valvani, Shri C, Solubility and Partitioning I: Solubility of Nonelectrolytes in Water, J. of Pharmaceutical Sciences, vol. 69(8) pp. 912-922, 1980.
Yalkowsky, Samuel H, Handbook of Acqueous Solubility Data, Solutions, pp. 1110-1111, CRC Press, Boca Raton, London, New York, Wash. D.C.
Yue, W., Genotoxic metabolites of estradiol in breast: potential mechanism of estradiol induced carcinogenesis, Journal of Steroid Biochem & Mol Biology, vol. 86 pp. 477-486, 2003.
Zava, David T. et al., Percutaneous absorption of progesterone, Maturitas 77 (2014) 91-92, Elsevier.
Zava, David T., Topical Progesterone Delivery and Levels in Serum, Saliva, Capillary Blood, and Tissues, Script, ZRT Laboratory, pp. 4-5. http://www.zrtiab.com/component/docman/cat_view/10-publications?Itemid.

\* cited by examiner

VAGINAL INSERTED ESTRADIOL PHARMACEUTICAL COMPOSITIONS AND METHODS

CROSS REFERENCE TO RELATED APPLICATIONS

This application is a continuation of U.S. patent application Ser. No. 14/521,002, entitled "VAGINAL INSERTED ESTRADIOL PHARMACEUTICAL COMPOSITIONS AND METHODS", which was filed on Oct. 22, 2014, which claims priority to U.S. Provisional Application Ser. No. 61/932,140, entitled "VAGINAL INSERTED ESTRADIOL PHARMACEUTICAL COMPOSITIONS AND METHODS", which was filed on Jan. 27, 2014; and U.S. Provisional Application Ser. No. 61/894,411, entitled "SOLUBLE ESTRADIOL CAPSULE FOR VAGINAL INSERTION," which was filed on Oct. 22, 2013. U.S. patent application Ser. No. 14/521,002 is also a continuation-in-part of PCT/US2013/46443, entitled "SOLUBLE ESTRADIOL CAPSULE FOR VAGINAL INSERTION", filed Jun. 18, 2013, which claims priority to U.S. Provisional Application Ser. No. 61/745,313, entitled "SOLUBLE ESTRADIOL CAPSULE FOR VAGINAL INSERTION," which was filed on Dec. 21, 2012. U.S. patent application Ser. No. 14/521,002 is also a continuation-in-part of International Application Serial No. PCT/US2013/023309, entitled "TRANSDERMAL HORMONE REPLACEMENT THERAPIES," which was filed Jan. 25, 2013; and U.S. patent application Ser. No. 13/843,362, entitled "TRANSDERMAL HORMONE REPLACEMENT THERAPIES," which was filed Mar. 15, 2013; both of which claim priority to U.S. patent application Ser. No. 13/684,002, entitled "NATURAL COMBINATION HORMONE REPLACEMENT PHARMACEUTICAL COMPOSITIONS AND THERAPIES," which was filed Nov. 21, 2012; which claims priority to; U.S. Provisional Application Ser. No. 61/661,302, entitled "ESTRADIOL PHARMACEUTICAL COMPOSITIONS," which was filed on Jun. 18, 2012; and U.S. Provisional Application Ser. No. 61/662,265, entitled "PROGESTERONE PHARMACEUTICAL COMPOSITIONS," which was filed on Jun. 20, 2012. All aforementioned applications are hereby incorporated by reference herein in their entirety.

BACKGROUND

This application is directed to pharmaceutical compositions, methods, and devices related to hormone replacement therapy.

Postmenopausal women frequently suffer from atrophic vaginitis or vulvar and vaginal atrophy (hereinafter "vulvovaginal atrophy" or "VVA") with symptoms including, for example, vaginal dryness, vaginal odor, vaginal or vulvar irritation or itching, dysuria (pain, burning, or stinging when urinating), dysparuenia (vaginal pain associated with sexual activity), or vaginal bleeding associated with sexual activity. Other symptoms include soreness; with urinary frequency and urgency; urinary discomfort and incontinence also occurring ("estrogen-deficient urinary state(s)"). One symptom of vaginal atrophy is an increased vaginal pH, which creates an environment more susceptible to infections. The mucosal epithelium of the VVA patients also reported to show signs of severe atrophy and upon cytological examination accompanied by an increased number of the parabasal cells and a reduced number of superficial cells.

Each of these VVA-related states manifest symptoms associated with decreased estrogenization of the vulvovaginal tissue, and can even occur in women treated with oral administration of an estrogen-based pharmaceutical drug product. Although VVA is most common with menopausal women, it can occur at any time in a woman's life cycle.

Estrogen treatment has proven to be very successful in controlling menopausal symptoms, including vaginal atrophy (VVA). Several studies have shown that the symptoms connected with vaginal atrophy are often relieved by estrogen treatment given either systemically or topically. The existing treatments have numerous problems, for example compliance issues with patients not completing or continuing treatment due to the problems associated with the form of treatment.

Accordingly, disclosed herein is, among other things, a new soft gel vaginal pharmaceutical composition and dosage form containing solubilized estradiol for the treatment of VVA. The soft gel vaginal pharmaceutical composition has been designed to mitigate common limitations found with other vaginal forms of estradiol. The soft gel vaginal pharmaceutical composition is expected to ease vaginal administration, provide improved safety of insertion, minimize vaginal discharge following administration, and provide a more effective dosage form with improved efficacy, safety and patient compliance.

SUMMARY

According to various aspects and embodiments of this disclosure, a soft gel vaginal pharmaceutical composition as a potential treatment for post-menopausal women suffering with moderate to severe symptoms of VVA is provided.

Provided herein is a pessary comprising: a) a therapeutically effective amount of estradiol; and b) a solubilizing agent comprising a medium chain oil.

In some embodiments, the pessary comprises about 1 µg to about 25 µg of estradiol. For example, the pessary can include about 1 µg to about 10 µg of estradiol; and about 10 µg to about 25 µg of estradiol.

In some embodiments, the estradiol is solubilized.

In some embodiments, the medium chain oil comprises at least one C6-C12 fatty acid or a glycol, monoglyceride, diglyceride, or triglyceride ester thereof.

In some embodiments, the solubilizing agent comprises at least one ester selected from the group consisting of: an ester of caproic fatty acid, an ester of caprylic fatty acid, an ester of capric fatty acid, and combinations thereof. For example, the solubilizing agent can include a caprylic/capric triglyceride.

In some embodiments, the pessary further comprises a capsule. For example, the capsule can be a soft gelatin capsule.

Also provided herein is a pessary comprising: a) a therapeutically effective amount of estradiol, b) a caprylic/capric triglyceride, c) a non-ionic surfactant comprising PEG-6 palmitostearate and ethylene glycol palmitostearate; and d) a soft gelatin capsule.

In some embodiments, a pessary provided herein comprises about 2 µg of estradiol, wherein administration of the pessary to a patient provides, in a plasma sample from the patient: 1) a corrected geometric mean peak plasma concentration ($C_{max}$) of estradiol of about 19 pg*hr/ml to about 29 pg*hr/ml; and 2) a corrected geometric mean area under the curve $(AUC)_{0-24}$ of estradiol of about 75 pg*hr/ml to about 112 pg*hr/ml.

In some embodiments, a pessary provided herein comprises about 25 µg of estradiol, wherein administration of the pessary to a patient provides, in a plasma sample from the patient: 1) a corrected geometric mean peak plasma concentration ($C_{max}$) of estrone of about 9 pg*hr/ml to about 14 pg*hr/ml; and 2) a corrected geometric mean area under the curve (AUC)$_{0-24}$ of estrone of about 43 pg*hr/ml to about 65 pg*hr/ml.

In some embodiments, a pessary provided herein comprises about 25 μg of estradiol, wherein administration of the pessary to a patient provides, in a plasma sample from the patient: 1) a corrected geometric mean peak plasma concentration (C$_{max}$) of estrone sulfate of about 416 pg*hr/ml to about 613 pg*hr/ml; and 2) a corrected geometric mean area under the curve (AUC)$_{0-24}$ of estrone sulfate of about 3598 pg*hr/ml to about 5291 pg*hr/ml.

In some embodiments, a pessary provided herein comprises about 10 μg of estradiol, wherein administration of the pessary to a patient provides, in a plasma sample from the patient: 1) a corrected geometric mean peak plasma concentration (C$_{max}$) of estradiol of about 12 pg*hr/ml to about 18 pg*hr/ml; and 2) a corrected geometric mean area under the curve (AUC)$_{0-24}$ of estradiol of about 42 pg*hr/ml to about 63 pg*hr/ml. In some embodiments, the pessary further provides a corrected geometric mean time to peak plasma concentration (T$_{max}$) of estradiol of about 1 hrs to about 3 hrs.

In some embodiments, a pessary provided herein comprises about 10 μg of estradiol, wherein administration of the pessary to a patient provides, in a plasma sample from the patient: 1) a corrected geometric mean peak plasma concentration (C$_{max}$) of estrone of about 4 pg*hr/ml to about 7 pg*hr/ml; and 2) a corrected geometric mean area under the curve (AUC)$_{0-24}$ of estrone of about 20 pg*hr/ml to about 31 pg*hr/ml. In some embodiments, the pessary further provides a corrected geometric mean time to peak plasma concentration (T$_{max}$) of estrone of about 4 hrs to about 8 hrs.

In some embodiments, a pessary provided herein comprises about 10 μg of estradiol, wherein administration of the pessary to a patient provides, in a plasma sample from the patient: 1) a corrected geometric mean peak plasma concentration (C$_{max}$) of estrone sulfate of about 10 pg*hr/ml to about 16 pg*hr/ml; and 2) a corrected geometric mean area under the curve (AUC)$_{0-24}$ of estrone sulfate of about 56 pg*hr/ml to about 84 pg*hr/ml. In some embodiments, the pessary further provides a corrected geometric mean time to peak plasma concentration (T$_{max}$) of estrone sulfate of about 4 hrs to about 7 hrs.

In some embodiments, a pessary provided herein comprises about 4 μg of estradiol, wherein administration of the pessary to a patient provides, in a plasma sample from the patient: 1) a corrected geometric mean peak plasma concentration (C$_{max}$) of estradiol of about 4 pg*hr/ml to about 8 pg*hr/ml; and 2) a corrected geometric mean area under the curve (AUC)$_{0-24}$ of estradiol of about 16 pg*hr/ml to about 26 pg*hr/ml. In some embodiments, the pessary further provides a corrected geometric mean time to peak plasma concentration (T$_{max}$) of estradiol of about 0.25 hrs to about 2 hrs.

In some embodiments, a pessary provided herein comprises about 4 μg of estradiol, wherein administration of the pessary to a patient provides, in a plasma sample from the patient: 1) a corrected geometric mean peak plasma concentration (C$_{max}$) of estrone of about 1 pg*hr/ml to about 3 pg*hr/ml; and 2) a corrected geometric mean area under the curve (AUC)$_{0-24}$ of estrone of about 8 pg*hr/ml to about 13 pg*hr/ml. In some embodiments, the pessary further provides a corrected geometric mean time to peak plasma concentration (T$_{max}$) of estrone of about 1 hrs to about 4 hrs.

In some embodiments, a pessary provided herein comprises about 4 μg of estradiol, wherein administration of the pessary to a patient provides, in a plasma sample from the patient: 1) a corrected geometric mean peak plasma concentration (C$_{max}$) of estrone sulfate of about 4 pg*hr/ml to about 7 pg*hr/ml; and 2) a corrected geometric mean area under the curve (AUC)$_{0-24}$ of estrone sulfate of about 22 pg*hr/ml to about 34 pg*hr/ml. In some embodiments, the pessary further provides a corrected geometric mean time to peak plasma concentration (T$_{max}$) of estrone sulfate of about 1 hrs to about 3 hrs.

Also provided herein is a pessary comprising about 1 μg to about 25 μg of estradiol, wherein administration of the pessary to a patient provides a corrected geometric mean peak plasma concentration (C$_{max}$) of estradiol that is less than about 30 pg*hr/ml. For example, administration of the pessary to a patient provides a corrected geometric mean peak plasma concentration (C$_{max}$) of estradiol that is less than about 18 pg*hr/ml.

In some embodiments, a pessary comprising about 1 μg to about 25 μg of estradiol is provided, wherein administration of the pessary to a patient provides a corrected geometric mean area under the curve (AUC)$_{0-24}$ of estradiol that is less than about 112 pg*hr/ml. For example, administration of the pessary to a patient provides a corrected geometric mean area under the curve (AUC)$_{0-24}$ of estradiol that is less than about 63 pg*hr/ml.

In some embodiments, a pessary comprising about 1 μg to about 25 μg of estradiol is provided, wherein administration of the pessary to a patient provides a corrected geometric mean peak plasma concentration (C$_{max}$) of estrone that is less than about 14 pg*hr/ml. For example, administration of the pessary to a patient provides a corrected geometric mean peak plasma concentration (C$_{max}$) of estrone that is less than about 7 pg*hr/ml.

In some embodiments, a pessary comprising about 1 μg to about 25 μg of estradiol is provided, wherein administration of the pessary to a patient provides a corrected geometric mean area under the curve (AUC)$_{0-24}$ of estrone that is less than about 65 pg*hr/ml. For example, administration of the pessary to a patient provides a corrected geometric mean area under the curve (AUC)$_{0-24}$ of estrone that is less than about 31 pg*hr/ml.

In some embodiments, a pessary comprising about 1 μg to about 25 μg of estradiol is provided, wherein administration of the pessary to a patient provides a corrected geometric mean peak plasma concentration (C$_{max}$) of estrone sulfate that is less than about 613 pg*hr/ml. For example, administration of the pessary to a patient provides a corrected geometric mean peak plasma concentration (C$_{max}$) of estrone sulfate that is less than about 16 pg*hr/ml.

In some embodiments, a pessary comprising about 1 μg to about 25 μg of estradiol is provided, wherein administration of the pessary to a patient provides a corrected geometric mean area under the curve (AUC)$_{0-24}$ of estrone sulfate that is less than about 5291 pg*hr/ml. For example, administration of the pessary to a patient provides a corrected geometric mean area under the curve (AUC)$_{0-24}$ of estrone sulfate that is less than about 84 pg*hr/ml.

Further provided herein is a pessary comprising about 1 μg to about 25 μg of estradiol, wherein administration of the pessary to the proximal region of the vagina of a patient provides a therapeutically effective concentration of estradiol over 24 hours in the proximal region of the vagina.

This disclosure also provides a method of treating an estrogen-deficient state, the method comprising administering to a patient in need thereof, a pessary as provided herein. In some embodiments, a method of treating vulvovaginal atrophy is provided, the method comprising administering to a patient in need thereof, a pessary as provided herein.

In some embodiments of the methods provided herein, treatment comprises reducing the severity of one or more symptoms selected from the group consisting of: vaginal dryness, dyspareunia, vaginal or vulvar irritation, vaginal or vulvar burning, vaginal or vulvar itching, dysuria, and vaginal bleeding associated with sexual activity.

In some embodiments of the methods provided herein treatment comprises reducing the vaginal pH of the patient. For example, treatment comprises reducing the vaginal pH of the patient to a pH of less than about 5.0.

In some embodiments of the methods provided herein treatment comprises a change in cell composition of the patient. For example, the change in cell composition comprises reducing the number of parabasal vaginal cells or increasing the number of superficial vaginal cells. In some embodiments, the number of parabasal vaginal cells in the patient are reduced by at least about 35% (e.g., at least about 50%). In some embodiments, the number of superficial vaginal cells are increased by at least about 5% (e.g., at least about 35%).

Further provided herein is a method for reducing vaginal discharge following administration of a pessary, the method comprising administering to a patient in need thereof, a pessary provided herein, wherein the vaginal discharge following administration of the pessary is compared to the vaginal discharge following administration of a reference drug.

DRAWINGS

The above-mentioned features and objects of the this disclosure will become more apparent with reference to the following description taken in conjunction with the accompanying drawings wherein like reference numerals denote like elements and in which.

DETAILED DESCRIPTION

Figure 1:
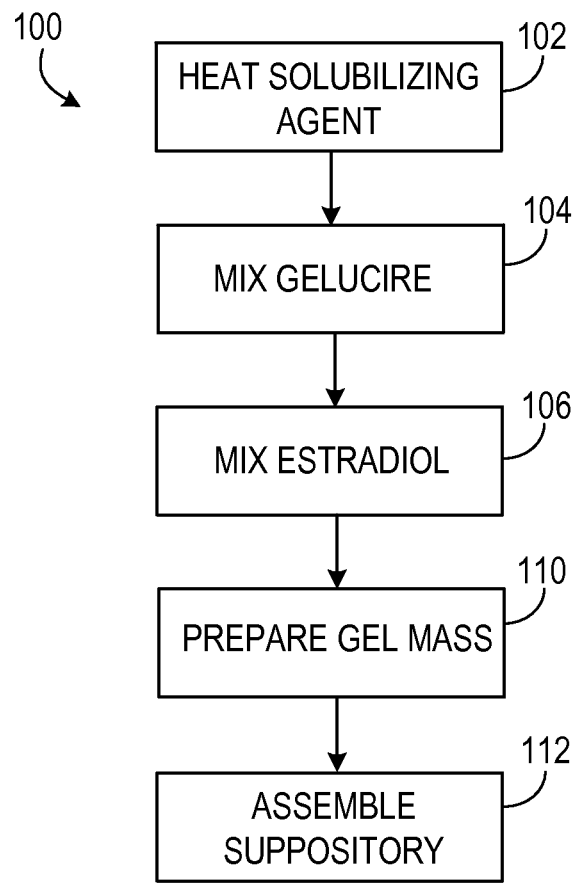
FIG. 1 is a flow diagram illustrating a process in accordance with various embodiments of the invention.

In the following detailed description of embodiments of this disclosure, reference is made to the accompanying drawings in which like references indicate similar elements, and in which is shown by way of illustration specific embodiments in which the this disclosure may be practiced. These embodiments are described in sufficient detail to enable those skilled in the art to practice the this disclosure, and it is to be understood that other embodiments may be utilized and that other changes may be made without departing from the scope of the this disclosure. The following detailed description is, therefore, not to be taken in a limiting sense, and the scope of this disclosure is defined only by the appended claims. As used in this disclosure, the term "or" shall be understood to be defined as a logical disjunction (i.e., and/or) and shall not indicate an exclusive disjunction unless expressly indicated as such with the terms "either," "unless," "alternatively," and words of similar effect.

DEFINITIONS

The term "active pharmaceutical ingredient" ("API") as used herein, means the active compound(s) used in formulating a drug product.

The term "co-administered" as used herein, means that two or more drug products are administered simultaneously or sequentially on the same or different days.

The term "drug product" as used herein means at least one active pharmaceutical ingredient in combination with at least one excipient and provided in unit dosage form.

The term "area under the curve" ("AUC") refers to the area under the curve defined by changes in the blood concentration of an active pharmaceutical ingredient (e.g., estradiol or progesterone), or a metabolite of the active pharmaceutical ingredient, over time following the administration of a dose of the active pharmaceutical ingredient. "$AUC_{0-\infty}$" is the area under the concentration-time curve extrapolated to infinity following the administration of a dose. "$AUC_{0-t}$" is the area under the concentration-time curve from time zero to time t following the administration of a dose, wherein t is the last time point with a measurable concentration.

The term "$C_{max}$" refers to the maximum value of blood concentration shown on the curve that represents changes in blood concentrations of an active pharmaceutical ingredient (e.g., progesterone or estradiol), or a metabolite of the active pharmaceutical ingredient, over time.

The term "$T_{max}$" refers to the time that it takes for the blood concentration an active pharmaceutical ingredient (e.g., estradiol or progesterone), or a metabolite of the active pharmaceutical ingredient, to reach the maximum value.

The term "bioavailability," which has the meaning defined in 21 C.F.R. §320.1(a), refers to the rate and extent to which an API or active ingredient or active moiety is absorbed from a drug product and becomes available at the site of action. For example, bioavailability can be measured as the amount of API in the blood (serum or plasma) as a function of time. Pharmacokinetic (PK) parameters such as AUC, $C_{max}$, or $T_{max}$ may be used to measure and assess bioavailability. For drug products that are not intended to be absorbed into the bloodstream, bioavailability may be assessed by measurements intended to reflect the rate and extent to which the API or active ingredient or active moiety becomes available at the site of action.

The term "bioequivalent," which has the meaning defined in 21 C.F.R. §320.1(e), refers to the absence of a significant difference in the rate and extent to which the API or active ingredient or active moiety in pharmaceutical equivalents or pharmaceutical alternatives becomes available at the site of drug action when administered at the same molar dose under similar conditions in an appropriately designed study. Where there is an intentional difference in rate (e.g., in certain extended release dosage forms), certain pharmaceutical equivalents or alternatives may be considered bioequivalent if there is no significant difference in the extent to which the active ingredient or moiety from each product becomes available at the site of drug action. This applies only if the difference in the rate at which the active ingredient or moiety becomes available at the site of drug action is intentional and is reflected in the proposed labeling, is not essential to the attainment of effective body drug concentrations on chronic use, and is considered medically insignificant for the drug. In practice, two products are considered bioequivalent if the 90% confidence interval of the AUC, $C_{max}$, or optionally $T_{max}$ is within 80.00% to 125.00%.

The term "bio-identical," "body-identical," or "natural" used in conjunction with the hormones disclosed herein, means hormones that match the chemical structure and effect of those that occur naturally or endogenously in the human body. An exemplary natural estrogen is estradiol.

The term "bio-identical hormone" or "body-identical hormone" refers to an active pharmaceutical ingredient that is structurally identical to a hormone naturally or endogenously found in the human body (e.g., estradiol and progesterone).

The term "estradiol" refers to (17β)-estra-1,3,5(10)-triene-3,17-diol. Estradiol is also interchangeably called 17β-estradiol, oestradiol, or E2, and is found endogenously in the human body. As used herein, estradiol refers to the bio-identical or body-identical form of estradiol found in the human body having the structure:

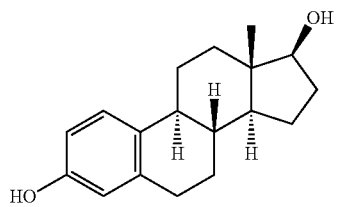

Estradiol is supplied in an anhydrous or hemi-hydrate form. For the purposes of this disclosure, the anhydrous form or the hemihydrate form can be substituted for the other by accounting for the water or lack of water according to well-known and understood techniques.

The term "solubilized estradiol" means that the estradiol or a portion thereof is solubilized or dissolved in the solubilizing agent(s) or the formulations disclosed herein. Solubilized estradiol may include estradiol that is about 80% solubilized, about 85% solubilized, about 90% solubilized, about 95% solubilized, about 96% solubilized, about 97% solubilized, about 98% solubilized, about 99% solubilized or about 100% solubilized. In some embodiments, the estradiol is "fully solubilized" with all or substantially all of the estradiol being solubilized or dissolved in the solubilizing agent. Fully solubilized estradiol may include estradiol that is about 97% solubilized, about 98% solubilized, about 99% solubilized or about 100% solubilized. Solubility can be expressed as a mass fraction (% w/w, which is also referred to as wt %).

The term "progesterone" refers to pregn-4-ene-3,20-dione. Progesterone is also interchangeably called P4 and is found endogenously in the human body. As used herein, progesterone refers to the bio-identical or body-identical form of progesterone found in the human body having the structure:

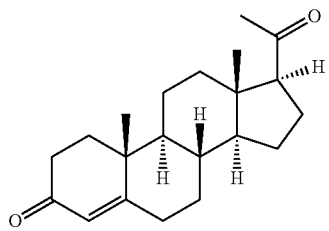

The term "solubilized progesterone" means that the progesterone or a portion thereof is solubilized or dissolved in the solubilizing agent(s) or the formulations disclosed herein. In some embodiments, the progesterone is "partially solubilized" with a portion of the progesterone being solubilized or dissolved in the solubilizing agent and a portion of the progesterone being suspended in the solubilizing agent. Partially solubilized progesterone may include progesterone that is about 1% solubilized, about 5% solubilized, about 10% solubilized, about 15% solubilized, about 20% solubilized, about 30% solubilized, about 40% solubilized, about 50% solubilized, about 60% solubilized, about 70% solubilized, about 80% solubilized, about 85% solubilized, about 90% solubilized or about 95% solubilized. In other embodiments, the progesterone is "fully solubilized" with all or substantially all of the progesterone being solubilized or dissolved in the solubilizing agent. Fully solubilized progesterone may include progesterone that is about 97% solubilized, about 98% solubilized, about 99% solubilized or about 100% solubilized. Solubility can be expressed as a mass fraction (% w/w, which is also referred to as wt %).

The terms "micronized progesterone" and "micronized estradiol," as used herein, include micronized progesterone and micronized estradiol having an X50 particle size value below about 15 microns or having an X90 particle size value below about 25 microns. The term "X50" means that one-half of the particles in a sample are smaller in diameter than a given number. For example, micronized progesterone having an X50 of 5 microns means that, for a given sample of micronized progesterone, one-half of the particles have a diameter of less than 5 microns. Similarly, the term "X90" means that ninety percent (90%) of the particles in a sample are smaller in diameter than a given number.

The term "glyceride" is an ester of glycerol (1,2,3-propanetriol) with acyl radicals of fatty acids and is also known as an acylglycerol. If only one position of the glycerol molecule is esterified with a fatty acid, a "monoglyceride" or "monoacylglycerol" is produced; if two positions are esterified, a "diglyceride" or "diacylglycerol" is produced; and if all three positions of the glycerol are esterified with fatty acids, a "triglyceride" or "triacylglycerol" is produced. A glyceride is "simple" if all esterified positions contain the same fatty acid; whereas a glyceride is "mixed" if the esterified positions contained different fatty acids. The carbons of the glycerol backbone are designated sn-1, sn-2 and sn-3, with sn-2 being in the middle carbon and sn-1 and sn-3 being the end carbons of the glycerol backbone.

The term "solubilizing agent" refers to an agent or combination of agents that solubilize an active pharmaceutical ingredient (e.g., estradiol or progesterone). For example and without limitation, suitable solubilizing agents include medium chain oils and other solvents and co-solvents that solubilize or dissolve an active pharmaceutical ingredient to a desirable extent. Solubilizing agents suitable for use in the formulations disclosed herein are pharmaceutical grade solubilizing agents (e.g., pharmaceutical grade medium chain oils). It will be understood by those of skill in the art that other excipients or components can be added to or mixed with the solubilizing agent to enhance the properties or performance of the solubilizing agent or resulting formulation. Examples of such excipients include, but are not limited to, surfactants, emulsifiers, thickeners, colorants, flavoring agents, etc. In some embodiments, the solubilizing agent is a medium chain oil and, in some other embodiments, the medium chain oil is combined with a co-solvent(s) or other excipient(s).

The term "medium chain" is used to describe the aliphatic chain length of fatty acid containing molecules. "Medium chain" specifically refers to fatty acids, fatty acid esters, or fatty acid derivatives that contain fatty acid aliphatic tails or carbon chains that contain 6 (C6) to 14 (C14) carbon atoms, 8 (C8) to 12 (C12) carbon atoms, or 8 (C8) to 10 (C10) carbon atoms.

The terms "medium chain fatty acid" and "medium chain fatty acid derivative" are used to describe fatty acids or fatty acid derivatives with aliphatic tails (i.e., carbon chains) having 6 to 14 carbon atoms. Fatty acids consist of an unbranched or branched aliphatic tail attached to a carboxylic acid functional group. Fatty acid derivatives include, for example, fatty acid esters and fatty acid containing molecules, including, without limitation, mono-, di- and triglycerides that include components derived from fatty acids. Fatty acid derivatives also include fatty acid esters of ethylene or propylene glycol. The aliphatic tails can be saturated or unsaturated (i.e., having one or more double bonds between carbon atoms). In some embodiments, the aliphatic tails are saturated (i.e., no double bonds between carbon atoms). Medium chain fatty acids or medium chain fatty acid derivatives include those with aliphatic tails having 6-14 carbons, including those that are C6-C14, C6-C12, C8-C14, C8-C12, C6-C10, C8-C10, or others. Examples of medium chain fatty acids include, without limitation, caproic acid, caprylic acid, capric acid, lauric acid, myristic acid, and derivatives thereof.

The term "oil," as used herein, refers to any pharmaceutically acceptable oil, especially medium chain oils, and specifically excluding peanut oil, that can suspend or solubilize bioidentical progesterone or estradiol, including starting materials or precursors thereof, including micronized progesterone or micronized estradiol as described herein.

The term "medium chain oil" refers to an oil wherein the composition of the fatty acid fraction of the oil is substantially medium chain (i.e., C6 to C14) fatty acids, i.e., the composition profile of fatty acids in the oil is substantially medium chain. As used herein, "substantially" means that between 20% and 100% (inclusive of the upper and lower limits) of the fatty acid fraction of the oil is made up of medium chain fatty acids, i.e., fatty acids with aliphatic tails (i.e., carbon chains) having 6 to 14 carbons. In some embodiments, about 25%, about 30%, about 35%, about 40%, about 45%, about 50%, about 55%, about 60%, about 65%, about 70%, about 75%, about 85%, about 90% or about 95% of the fatty acid fraction of the oil is made up of medium chain fatty acids. Those of skill in the art that will readily appreciate that the terms "alkyl content" or "alkyl distribution" of an oil can be used in place of the term "fatty acid fraction" of an oil in characterizing a given oil or solubilizing agent, and these terms are used interchangeable herein. As such, medium chain oils suitable for use in the formulations disclosed herein include medium chain oils wherein the fatty acid fraction of the oil is substantially medium chain fatty acids, or medium chain oils wherein the alkyl content or alkyl distribution of the oil is substantially medium chain alkyls (C6-C12 alkyls). It will be understood by those of skill in the art that the medium chain oils suitable for use in the formulations disclosed herein are pharmaceutical grade (e.g., pharmaceutical grade medium chain oils). Examples of medium chain oils include, for example and without limitation, medium chain fatty acids, medium chain fatty acid esters of glycerol (e.g., for example, mono-, di-, and triglycerides), medium chain fatty acid esters of propylene glycol, medium chain fatty acid derivatives of polyethylene glycol, and combinations thereof.

The term "ECN" or "equivalent carbon number" means the sum of the number of carbon atoms in the fatty acid chains of an oil, and can be used to characterize an oil as, for example, a medium chain oil or a long-chain oil. For example, tripalmitin (tripalmitic glycerol), which is a simple triglyceride containing three fatty acid chains of 16 carbon atoms, has an ECN of 3×16=48. Conversely, a triglyceride with an ECN=40 may have "mixed" fatty acid chain lengths of 8, 16 and 16; 10, 14 and 16; 8, 14 and 18; etc. Naturally occurring oils are frequently "mixed" with respect to specific fatty acids, but tend not to contain both long chain fatty acids and medium chain fatty acids in the same glycerol backbone. Thus, triglycerides with ECN's of 21-42 typically contain predominately medium chain fatty acids; while triglycerides with ECN's of greater than 43 typically contain predominantly long chain fatty acids. For example, the ECN of corn oil triglyceride in the USP would be in the range of 51-54. Medium chain diglycerides with ECN's of 12-28 will often contain predominately medium chain fatty chains, while diglycerides with ECN's of 32 or greater will typically contain predominately long chain fatty acid tails. Monoglycerides will have an ECN that matches the chain length of the sole fatty acid chain. Thus, monoglyceride ECN's in the range of 6-14 contain mainly medium chain fatty acids, and monoglycerides with ECN's 16 or greater will contain mainly long chain fatty acids.

The average ECN of a medium chain triglyceride oil is typically 21-42. For example, as listed in the US Pharmacopeia (USP), medium chain triglycerides have the following composition as the exemplary oil set forth in the table below:

| Fatty-acid Tail Length | % of oil | Exemplary Oil |
| --- | --- | --- |
| 6 | ≤2.0 | 2.0 |
| 8 | 50.0-80.0 | 70.0 |
| 10 | 20.0-50.0 | 25.0 |
| 12 | ≤3.0 | 2.0 |
| 14 | ≤1.0 | 1.0 | and would have an average ECN of 3*[(6*0.02)+(8*0.70)+(10*0.25)+(12*0.02)+(14*0.01)]=25.8. The ECN of the exemplary medium chain triglycerides oil can also be expressed as a range (per the ranges set forth in the USP) of 24.9-27.0. For oils that have mixed mono-, di-, and trigylcerides, or single and double fatty acid glycols, the ECN of the entire oil can be determined by calculating the ECN of each individual component (e.g., C8 monoglycerics, C8 diglycerides, C10 monoglycerides, and C10 monoglycerides) and taking the sum of the relative percentage of the component multiplied by the ECN normalized to a monoglyceride for each component. For example, the oil having C8 and C10 mono- and diglycerides shown in the table below has an ECN of 8.3, and is thus a medium chain oil.

| Fatty-acid Chain Length | % of oil | ECN as % of oil (chain length) × (% in oil) | ECN as % of oil normalized to monoglyceride |
|---|---|---|---|
| C8 monoglyceride | 47 | 8 × 0.47 = 3.76 | 3.76 |
| C10 monoglyceride | 8 | 10 × 0.08 = 0.8 | 0.8 |
| C8 diglyceride | 38 | 2 × (8 × 0.38) = 6.08 | 6.08/2 = 3.04 |
| C10 diglyceride | 7 | 2 × (10 × 0.07) = 1.4 | 1.4/2 = 0.7 |
| OIL ECN (normalized to monoglycerides) | | | 8.3 |

Expressed differently, ECN can be calculated as each chain length in the composition multiplied by its relative percentage in the oil: (8*0.85)+(10*0.15)=8.3.

The term "excipients," as used herein, refers to non-API ingredients such as solubilizing agents, anti-oxidants, oils, lubricants, and others used in formulating pharmaceutical products.

The term "patient" or "subject" refers to an individual to whom the pharmaceutical composition is administered.

The term "pharmaceutical composition" refers to a pharmaceutical composition comprising at least a solubilizing agent and estradiol. As used herein, pharmaceutical compositions are delivered, for example via pessary (i.e., vaginal suppository), or absorbed vaginally.

The term "progestin" means any natural or man-made substance that has pharmacological properties similar to progesterone.

The term "reference listed drug product" ("RLD") means VAGIFEM® (estradiol vaginal tablets) or ESTRACE® vaginal cream.

The terms "treat," "treating," and "treatment" refer to any indicia of success in the treatment or amelioration of an injury, disease, or condition, including any objective or subjective parameter such as abatement; remission; diminishing of symptoms or making the injury, disease, or condition more tolerable to the patient; slowing in the rate of degeneration or decline; or improving a patient's physical or mental well-being. The treatment or amelioration of symptoms can be based on objective or subject parameters, including the results of a physical examination, neuropsychiatric examinations, or psychiatric evaluation.

The terms "atrophic vaginitis," "vulvovaginal atrophy," "vaginal atrophy," and "VVA" are used herein interchangeably. The molecular morphology of VVA is well known in the medical field.

Introduction

Provided herein are pharmaceutical compositions comprising solubilized estradiol designed to be absorbed vaginally. The pharmaceutical compositions disclosed herein are designed to be absorbed and have their therapeutic effect locally, e.g., in vaginal or surrounding tissue. Further disclosed herein are data demonstrating efficacy of the pharmaceutical compositions disclosed, as well as methods relating to the pharmaceutical compositions. Generally, the pharmaceutical compositions disclosed herein are useful in VVA, dysparuenia, and other indications caused by decrease or lack of estrogen.

Additional aspects and embodiments of this disclosure include: providing increased patient ease of use while potentially minimizing certain side effects from inappropriate insertion, minimizing incidence of vulvovaginal mycotic infection compared to incidence of vulvovaginal mycotic infection due to usage of other vaginally applied estradiol products; and, improved side effect profile (e.g., pruritus) compared to the reference drug: VAGIFEM® (estradiol vaginal tablets, Novo Nordisk; Princeton, N.J.).

Pharmaceutical Composition

Functionality

According to embodiments, the pharmaceutical compositions disclosed herein are alcohol-free or substantially alcohol-free. The pharmaceutical compositions offer provide for improved patient compliance because of improvements over the prior offering. According to embodiments, the pharmaceutical compositions disclosed herein are encapsulated in soft gelatin capsules, which improve comfort during use. According to embodiments, the pharmaceutical compositions are substantially liquid, which are more readily absorbed in the vaginal tissue, and also are dispersed over a larger surface area of the vaginal tissue.

Estradiol

According to embodiments, the pharmaceutical compositions disclosed herein are for vaginal insertion in a single or multiple unit dosage form. According to embodiments, the estradiol in the pharmaceutical compositions is at least about: 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% solubilized. According to embodiments and where the estradiol is not 100% solubilized, the remaining estradiol is present in a micronized (crystalline) form that is absorbable by the body and retains biological functionality, either in its micronized form or in another form which the micronized form is converted to after administration.

According to embodiments, all or some of the estradiol is solubilized in a solubilizing agent during manufacturing process. According to embodiments, all or some of the estradiol is solubilized following administration (e.g., the micronized portion where the estradiol is not 100% solubilized is solubilized in a body fluid after administration). According to embodiments, because the estradiol is solubilized, the solubilizing agents taught herein, with or without additional excipients other than the solubilizing agents, are liquid or semi-solid. To the extent the estradiol is not fully solubilized at the time of administration/insertion, the estradiol should be substantially solubilized at a body temperature (average of 37° C.) and, generally, at the pH of the vagina (ranges from 3.8 to 4.5 in healthy patients; and 4.6 to 6.5 in VVA patients).

According to embodiments, the estradiol can be added to the pharmaceutical compositions disclosed herein as estradiol, estradiol hemihydrate, or other grade estradiol forms used in pharmaceutical compositions or formulations.

According to embodiments, estradiol dosage strengths vary. Estradiol (or estradiol hemihydrate, for example, to the extent the water content of the estradiol hemihydrate is accounted for) dosage strength of is from at least about 1 microgram (μg or μg) to at least about 50 μg. Specific dosage embodiments contain at least about: 1 μg, 2 μg, 3 μg, 4 μg, 5 μg, 6 μg, 7 μg, 8 μg, 9 μg, 10 μg, 11 μg, 12 μg, 13 μg, 14 μg, 15 μg, 16 μg, 17 μg, 18 μg, 19 μg, 20 μg, 21 μg, 22 μg, 23 μg, 24 μg, 25 μg, 26 μg, 27 μg, 28 μg, 29 μg, 30 μg, 31 μg, 32 μg, 33 μg, 34 μg, 35 μg, 36 μg, 37 μg, 38 μg, 39 μg, 40 μg, 41 μg, 42 μg, 43 μg, 44 μg, 45 μg, 46 μg, 47 μg, 48 μg, 49 μg, or 50 μg estradiol. According to embodiments, the pharmaceutical compositions contain at least about 2.5 μg; 4 μg 6.25 μg, 7.5 μg, 12.5 μg, 18.75 μg of estradiol. According to embodiments, the pharmaceutical compositions contain from about 1 μg to about 10 μg, from 3 μg to 7 μg, from about 7.5 μg to 12.5 μg, from about 10 μg to about 25 μg, about 1 μg, about 2.5 μg, from about 23.5 µg to 27.5 µg, from about 7.5 µg to 22.5 µg, from 10 µg to 25 µg of estradiol. The lowest clinically effective dose of estradiol is used for treatment of VVA and other indications set forth herein. In some embodiments, the estradiol dosage is about 4 µg. In one embodiment, the estradiol dosage is about 10 µg. In another embodiment, the estradiol dosage is about 25 µg.

Solvent System

According to embodiments, the solvent system that solubilizes the estradiol are medium chain fatty acid based solvents, together with other excipients. According to embodiments, the solvent system comprises non-toxic, pharmaceutically acceptable solvents, co-solvents, surfactants, and other excipients suitable for vaginal delivery or absorption.

According to embodiments, oils having medium chain fatty acids as a majority component are used as solubilizing agents to solubilize estradiol. According to embodiments, the solubilizing agents comprise medium chain fatty acid esters (e.g., esters of glycerol, ethylene glycol, or propylene glycol) or mixtures thereof. According to embodiments, the medium chain fatty acids comprise chain lengths from C6 to C14. According to embodiments the medium chain fatty acids comprise chain lengths from C6 to C12. According to embodiments the medium chain fatty acids substantially comprise chain lengths from C8-C10. ECN's for medium chain oils will be in the range of 21-42 for triglycerides, 12-28 for diglycerides, and 6-14 for monoglycerides.

According to embodiments, the medium chain fatty acids are saturated. According to embodiments, the medium chain fatty acids are predominantly saturated, i.e., greater than about 60% or greater than about 75% saturated.

According to embodiments, estradiol is soluble in the solubilizing agent at room temperature, although it may be desirable to warm certain solubilizing agents during manufacture to improve viscosity. According to embodiments, the solubilizing agent is liquid at between room temperature and about 50° C., at or below 50° C., at or below 40° C., or at or below 30° C.

According to embodiments, the solubility of estradiol in the medium chain oil, medium chain fatty acid, or solubilizing agent (or oil/surfactant) is at least about 0.01 wt %, 0.02 wt %, 0.05 wt %, 0.06 wt %, 0.08 wt %, 0.1 wt %, 0.2 wt %, 0.3 wt %, 0.4 wt %, 0.5 wt %, 0.6 wt %, 0.7 wt %, 0.8 wt %, 0.9 wt %, 1.0 wt %, or higher.

According to embodiments, medium chain solubilizing agents include, for example and without limitation saturated medium chain fatty acids: caproic acid (C6), enanthic acid (C7), caprylic acid (C8), pelargonic acid (C9), capric acid (C10), undecylic acid (C11), lauric acid (C12), tridecylic acid (C13), or myristic acid (C14). According to embodiments, the solubilizing agent comprises oils made of these free medium chain fatty acids, oils of medium chain fatty acid esters of glycerin, propylene glycol, or ethylene glycol, or combinations thereof. These examples comprise predominantly saturated medium chain fatty acids (i.e., greater than 50% of the fatty acids are medium chain saturated fatty acids). According to embodiments, predominantly C6 to C12 saturated fatty acids are contemplated. According to embodiments, the solubilizing agent is selected from at least one of a solvent or co-solvent.

According to embodiments, glycerin based solubilizing agents include: mono-, di-, or triglycerides and combinations and derivatives thereof. Exemplary glycerin based solubilizing agents include MIGLYOLs®, which are caprylic/capric triglycerides (SASOL Germany GMBH, Hamburg). MIGLYOLs includes MIGLYOL 810 (caprylic/capric triglyceride), MIGLYOL 812 (caprylic/capric triglyceride), MIGLYOL 816 (caprylic/capric triglyceride), and MIGLYOL 829 (caprylic/capric/succinic triglyceride). Other caprylic/capric triglyceride solubilizing agents are likewise contemplated, including, for example: caproic/caprylic/capric/lauric triglycerides; caprylic/capric/linoleic triglycerides; caprylic/capric/succinic triglycerides. According to embodiments, CAPMUL MCM, medium chain mono- and di-glycerides, is the solubilizing agent. Other and triglycerides of fractionated vegetable fatty acids, and combinations or derivatives thereof can be the solubilizing agent, according to embodiments. For example, the solubilizing agent can be 1,2,3-propanetriol (glycerol, glycerin, glycerine) esters of saturated coconut and palm kernel oil and derivatives thereof.

Ethylene and propylene glycols (which include polyethylene and polypropylene glycols) solubilizing agents include: glyceryl mono- and di-caprylates; propylene glycol monocaprylate (e.g., CAPMUL® PG-8 (the CAPMUL brands are owned by ABITEC, Columbus, Ohio)); propylene glycol monocaprate (e.g., CAPMUL PG-10); propylene glycol mono- and dicaprylates; propylene glycol mono- and dicaprate; diethylene glycol mono ester (e.g., TRANSCUTOL®, 2-(2-Ethoxyethoxyl)ethanol, GATTEFOSSÉ SAS); and diethylene glycol monoethyl ether. Other combinations of mono- and di-esters of propylene glycol or ethylene glycol are expressly contemplated are the solubilizing agent.

According to embodiments, the solubilizing agent comprises combinations of mono- and di-propylene and ethylene glycols and mono-, di-, and triglyceride combinations. According to embodiments, polyethylene glycol glyceride (GELUCIRE®, GATTEFOSSÉ SAS, Saint-Priest, France) can be used herein as the solubilizing agent or as a surfactant. For example, GELUCIRE 44/14 (PEG-32 glyceryl laurate EP), a medium chain fatty acid esters of polyethylene glycol, is a polyethylene glycol glyceride composed of mono-, di- and triglycerides and mono- and diesters of polyethylene glycol.

According to embodiments, commercially available fatty acid glycerol and glycol ester solubilizing agents are often prepared from natural oils and therefore may comprise components in addition to the fatty acid esters that predominantly comprise and characterize the solubilizing agent. Such other components may be, e.g., other fatty acid mono-, di-, and triglycerides; fatty acid mono- and diester ethylene or propylene glycols, free glycerols or glycols, or free fatty acids, for example. In some embodiments, when an oil/solubilizing agent is described herein as a saturated $C_8$ fatty acid mono- or diester of glycerol, the predominant component of the oil, i.e., >50 wt % (e.g., >75 wt %, >85 wt % or >90 wt %) is caprylic monoglycerides and caprylic diglycerides. For example, the Technical Data Sheet by ABITEC for CAPMUL MCM C8 describes CAPMUL MCM C8 as being composed of mono and diglycerides of medium chain fatty acids (mainly caprylic) and describes the alkyl content as ≤1% C6, ≥95% C8, ≤5% C10, and ≤1.5% C12 and higher.

For example, MIGLYOL 812 is a solubilizing agent that is generally described as a C8-C10 triglyceride because the fatty acid composition is at least about 80% triglyceride esters of caprylic acid (C8) and capric acid (C10). However, it also comprises small amounts of other fatty acids, e.g., less than about 5% of caproic acid (C6), lauric acid (C12), and myristic acid (C14). The product information sheet for various MIGLYOLs illustrate the various fatty acid components as follows:

| Tests | 810 | 812 | 818 | 829 | 840 |
|---|---|---|---|---|---|
| Caproic acid (C6:0) | max. 2.0 | max. 2.0 | max. 2 | max. 2 | max. 2 |
| Caprylic acid (C8:0) | 65.0-80.0 | 50.0-65.0 | 45-65 | 45-55 | 65-80 |
| Capric acid (C10:0) | 20.0-35.0 | 30.0-45.0 | 30-45 | 30-40 | 20-35 |
| Lauric acid (C12:0) | max. 2 | max. 2 | max. 3 | max. 3 | max. 2 |
| Myristic acid (C14:0) | max. 1.0 | max. 1.0 | max. 1 | max. 1 | max. 1 |
| Linoleic acid (C18:2) | — | — | 2-5 | — | — |
| Succinic acid | — | — | — | 15-20 | — |
| ECN | 25.5-26.4 | 26.1-27 | 26.52-28.56 | 26-27.6 | 25.5-26.4 |

According to embodiments, anionic or non-ionic surfactants may be used in pharmaceutical compositions containing solubilized estradiol. Ratios of solubilizing agent(s) to surfactant(s) vary depending upon the respective solubilizing agent(s) and the respective surfactant(s) and the desired physical characteristics of the resultant pharmaceutical composition. For example and without limitation, CAPMUL MCM and a non-ionic surfactant may be used at ratios including 65:35, 70:30, 75:25, 80:20, 85:15 and 90:10. Other non-limiting examples include: CAPMUL MCM and GELUCIRE 39/01 used in ratios including, for example and without limitation, 6:4, 7:3, and 8:2; CAPMUL MCM and GELUCIRE 43/01 used in ratios including, for example and without limitation, 7:3, and 8:2; CAPMUL MCM and GELUCIRE 50/13 used in ratios including, for example and without limitation, 7:3, and 8:2, and 9:1.

Other Excipients

According to embodiments, the pharmaceutical composition further comprises a surfactant. The surfactant can be a nonionic surfactant, cationic surfactant, anionic surfactant, or mixtures thereof. Suitable surfactants include, for example, water-insoluble surfactants having a hydrophilic-lipophilic balance (HLB) value less than 12 and water-soluble surfactants having a HLB value greater than 12. Surfactants that have a high HLB and hydrophilicity, aid the formation of oil-water droplets. The surfactants are amphiphilic in nature and are capable of dissolving or solubilizing relatively high amounts of hydrophobic drug compounds.

Non-limiting examples, include, Tween, Dimethylacetamide (DMA), Dimethyl sulfoxide (DMSO), Ethanol, Glycerin, N-methyl-2-pyrrolidone (NMP), PEG 300, PEG 400, Poloxamer 407, Propylene glycol, Phospholipids, Hydrogenated soy phosphatidylcholine (HSPC), Distearoylphosphatidylglycerol (DSPG), L-α-dimyristoylphosphatidylcholine (DMPC), L-α-dimyristoylphosphatidylglycerol (DMPG), Polyoxyl 35 castor oil (CREMOPHOR EL, CREMOPHOR ELP), Polyoxyl 40 hydrogenated castor oil (Cremophor RH 40), Polyoxyl 60 hydrogenated castor oil (CREMOPHOR RH 60), Polysorbate 20 (TWEEN 20), Polysorbate 80 (TWEEN 80), d-α-tocopheryl polyethylene glycol 1000 succinate (TPGS), Solutol HS-15, Sorbitan monooleate (SPAN 20), PEG 300 caprylic/capric glycerides (SOFTIGEN 767), PEG 400 caprylic/capric glycerides (LABRASOL), PEG 300 oleic glycerides (LABRAFIL M-1944CS), Polyoxyl 35 Castor oil (ETOCAS 35), Glyceryl Caprylate (Mono- and Diglycerides) (IMWITOR), PEG 300 linoleic glycerides (LABRAFIL M-2125CS), Polyoxyl 8 stearate (PEG 400 monosterate), Polyoxyl 40 stearate (PEG 1750 monosterate), and combinations thereof. Additionally, suitable surfactants include, for example, polyoxyethylene derivative of sorbitan monolaurate such as polysorbate, caprylcaproyl macrogol glycerides, polyglycolyzed glycerides, and the like.

According to embodiments, the non-ionic surfactant is selected from one or more of glycerol and polyethylene glycol esters of long chain fatty acids, for example, lauroyl macrogol-32 glycerides or lauroyl polyoxyl-32 glycerides, commercially available as GELUCIRE, including, for example, GELUCIRE 39/01 (glycerol esters of saturated C12-C18 fatty acids), GELUCIRE 43/01 (hard fat NF/JPE) and GELUCIRE 50/13 (stearoyl macrogol-32 glycerides EP, stearoyl polyoxyl-32 glycerides NF, stearoyl polyoxylglycerides (USA FDA IIG)). These surfactants may be used at concentrations greater than about 0.01%, and typically in various amounts of about 0.01%-10.0%, 10.1%-20%, and 20.1%-30%. In some embodiments, surfactants may be used at concentrations of about 1% to about 10% (e.g., about 1% to about 5%, about 2% to about 4%, about 3% to about 8%).

According to embodiments, non-ionic surfactants include, for example and without limitation: one or more of oleic acid, linoleic acid, palmitic acid, and stearic acid. According to embodiments, non-ionic surfactants comprise polyethylene sorbitol esters, including polysorbate 80, which is commercially available under the trademark TWEEN® 80 (polysorbate 80) (Sigma Aldrich, St. Louis, Mo.). Polysorbate 80 comprises approximately 60%-70% oleic acid with the remainder comprising primarily linoleic acids, palmitic acids, and stearic acids. Polysorbate 80 may be used in amounts ranging from about 5 to 50%, and according to embodiments, about 30% of the pharmaceutical composition total mass.

According to embodiments, the non-ionic surfactant includes PEG-6 palmitostearate and ethylene glycol palmitostearate, which are available commercially as TEFOSE® 63 (GATTEFOSSÉ SAS, Saint-Priest, France), which can be used with, for example, CAPMUL MCM having ratios of MCM to TEFOSE 63 of, for example, 8:2 or 9:1. According to embodiments, other solubilizing agents/non-ionic surfactants combinations include, for example, MIGLYOL 812: GELUCIRE 50/13 or MIGLYOL 812:TEFOSE 63.

According to embodiments, the surfactant can be an anionic surfactant, for example: ammonium lauryl sulfate, dioctyl sodium sulfosuccinate, perfluoro-octane sulfonic acid, potassium lauryl sulfate, or sodium stearate. Cationic surfactants are also contemplated.

According to embodiments, non-ionic or anionic surfactants can be used alone with at least one solubilizing agent or can be used in combination with other surfactants. Accordingly, such surfactants, or any other excipient as set forth herein, may be used to solubilize estradiol. The combination of solubilizing agent, surfactant, and other excipients should be designed whereby the estradiol is absorbed into the vaginal tissue. According to embodiments, the pharmaceutical composition will result in minimal vaginal discharge.

According to embodiments, the pharmaceutical composition further comprises at least one thickening agent. Generally, a thickening agent is added when the viscosity of the pharmaceutical composition results less than desirable absorption. According to embodiments, the surfactant(s) disclosed herein may also provide thickening of the pharmaceutical composition that, upon release, will aid the estradiol in being absorbed by the vaginal mucosa while minimizing vaginal discharge. Examples of thickening agents include: hard fats; propylene glycol; a mixture of hard fat EP/NF/JPE, glyceryl ricinoleate, ethoxylated fatty alcohols (ceteth-20, steareth-20) EP/NF (available as OVUCIRE® 3460, GATTEFOSSÉ, Saint-Priest, France); a mixture of hard fat EP/NF/JPE, glycerol monooleate (type 40) EP/NF (OVUCIRE WL 3264; a mixture of hard fat EP/NF/JPE, glyceryle monooleate (type 40) EP/NF (OVUCIRE WL 2944); a non-ionic surfactant comprising PEG-6 stearate, ethylene glycol palmitostearate, and PEG-32 stearate; TEFOSE 63 or a similar product; and a mixture of various hard fats (WITEPSOL®, Sasol Germany GmbH, Hamburg, Germany). Other thickening agents such as the alginates, certain gums such as xanthan gums, agar-agar, iota carrageenans, kappa carrageenans, etc. Several other compounds can act as thickening agents like gelatin, and polymers like HPMC, PVC, and CMC. According to embodiments, the viscosity of pharmaceutical compositions in accordance with various embodiments may comprise from about 50 cps to about 1000 cps at 25° C. A person of ordinary skill in the art will readily understand and select from suitable thickening agents.

According to embodiments, the thickening agent is a non-ionic surfactant. For example, polyethylene glycol saturated or unsaturated fatty acid ester or diester is the non-ionic surfactant thickening agent. In embodiments, the non-ionic surfactant comprises a polyethylene glycol long chain (C16-C20) fatty acid ester and further comprises an ethylene glycol long chain fatty acid ester, such as PEG-fatty acid esters or diesters of saturated or unsaturated C16-C18 fatty acids, e.g., oleic, lauric, palmitic, and stearic acids. In embodiments, the non-ionic surfactant comprises a polyethylene glycol long chain saturated fatty acid ester and further comprises an ethylene glycol long chain saturated fatty acid ester, such as PEG- and ethylene glycol-fatty acid esters of saturated C16-C18 fatty acids, e.g., palmitic and stearic acids. Such non-ionic surfactant can comprise PEG-6 stearate, ethylene glycol palmitostearate, and PEG-32 stearate, such as but not limited to TEFOSE 63.

According to embodiments, the non-ionic surfactant used as a thickening agent is not hydrophilic and has good emulsion properties. An illustrative example of such surfactant is TEFOSE 63, which has a hydrophilic-lipophilic balance (HLB) value of about 9-10.

According to embodiments, the pharmaceutical composition further comprises one or more mucoadherent agents to improve vaginal absorption of the estradiol. For example, a mucoadherent agent can be present to aid the pharmaceutical composition with adherence to the mucosa upon activation with water. According to embodiments, polycarbophil is the mucoadherent agent. According to embodiments, other mucoadherent agents include, for example and without limitation: poly (ethylene oxide) polymers having a molecular weight of from about 100,000 to about 900,000; chitosans carbopols including polymers of acrylic acid crosslinked with allyl sucrose or allyl pentaerythritol; polymers of acrylic acid and C10-C30 alkyl acrylate crosslinked with allyl pentaerythritol; carbomer homopolymer or copolymer that contains a block copolymer of polyethylene glycol and a long chain alkyl acid ester; and the like. According to embodiments, various hydrophilic polymers and hydrogels may be used as the mucoadherent agent. According to certain embodiments, the polymers or hydrogels can swell in response to contact with vaginal tissue or secretions, enhancing moisturizing and mucoadherent effects. The selection and amount of hydrophilic polymer may be based on the selection and amount of solubilizing agent. In some embodiments, the pharmaceutical composition includes a hydrophilic polymer but optionally excludes a gelling agent. In embodiments having a hydrogel, from about 5% to about 10% of the total mass may comprise the hydrophilic polymer. In further embodiments, hydrogels may be employed. A hydrogel may comprise chitosan, which swell in response to contact with water. In various embodiments, a cream pharmaceutical composition may comprise PEG-90 M. In some embodiments, a mucoadherent agent is present in the pharmaceutical formulation, in the soft gel capsule, or both.

According to embodiments, the pharmaceutical compositions include one or more thermoreversible gels, typically of the hydrophilic nature including for example and without limitation, hydrophilic sucrose and other saccharide-based monomers (U.S. Pat. No. 6,018,033, which is incorporated by reference).

According to embodiments, the pharmaceutical composition further comprises a lubricant. In some embodiments, a lubricant can be present to aid in formulation of a dosage form. For example, a lubricant may be added to ensure that capsules or tablets do not stick to one another during processing or upon storage. Any suitable lubricant may be used. For example, lecithin, which is a mixture of phospholipids, is the lubricant.

According to embodiments, the pharmaceutical composition further comprises an antioxidant. Any suitable anti-oxidant may be used. For example, butylated hydroxytoluene, butylated hydroxyanisole, and Vitamin E TPGS.

According to embodiments, the pharmaceutical composition comprises about 20% to about 80% solubilizing agent by weight, about 0.1% to about 5% lubricant by weight, and about 0.01% to about 0.1% antioxidant by weight.

The choice of excipient will depend on factors such as, for example, the effect of the excipient on solubility and stability. Additional excipients used in various embodiments may include colorants and preservatives. Examples of colorants include FD&C colors (e.g., blue No. 1 and Red No. 40), D&C colors (e.g., Yellow No. 10), and opacifiers (e.g., Titanium dioxide). According to embodiments, colorants, comprise about 0.1% to about 2% of the pharmaceutical composition by weight. According to embodiments, preservatives in the pharmaceutical composition comprise methyl and propyl paraben, in a ratio of about 10:1, and at a proportion of about 0.005% and 0.05% by weight.

Generally, the solubilizing agents, excipients, other additives used in the pharmaceutical compositions described herein, are non-toxic, pharmaceutically acceptable, compatible with each other, and maintain stability of the pharmaceutical composition and the various components with respect to each other. Additionally, the combination of various components that comprise the pharmaceutical compositions will maintain will result in the desired therapeutic effect when administered to a subject.

Solubility of Estradiol

According to embodiments, solubilizing agents comprising mixtures of medium chain fatty acid glycerides, e.g., $C_6$-$C_{12}$, $C_8$-$C_{12}$, or $C_8$-$C_{10}$ fatty acid mono- and diglycerides or mono-, di-, and triglycerides dissolve estradiol. As illustrated in the Examples, good results were obtained with solubilizing agents that are predominantly a mixture of C8-C10 saturated fatty acid mono- and diglycerides, or medium chain triglycerides (e.g., Miglyol 810 or 812). Longer chain glycerides appear to be not as well suited for dissolution of estradiol.

A solubilizing agent comprising propylene glycol monocaprylate (e.g., CAPRYOL) and 2-(2-Ethoxyethoxyl)ethanol (e.g., TRANSCUTOL) solubilized estradiol well.

Manufacture of the Pharmaceutical Composition

According to embodiments, the pharmaceutical composition is prepared via blending estradiol with a pharmaceutically acceptable solubilizing agent, including for example and without limitation, at least one medium chain fatty acid such as medium chain fatty acids consisting of at least one mono-, di-, or triglyceride, or derivatives thereof, or combinations thereof. According to embodiments, the pharmaceutical composition also comprises at least one glycol or derivatives thereof or combinations thereof or combinations of at least one glyceride and glycol. The glycol(s) may be used as solubilizing agents or to adjust viscosity and, thus, may be considered thickening agents, as discussed further herein. Optionally added are other excipients including, for example and without limitation, anti-oxidants, lubricants, and the like. According to embodiments, the pharmaceutical composition comprises sufficient solubilizing agent to fully solubilize the estradiol. It is expressly understood, however, the other volumes of solubilizing agent can be used depending on the level of estradiol solubilization desired. Persons of ordinary skill in the art will know and understand how to determine the volume of solubilizing agent and other excipients depending on the desired percent of estradiol to be solubilized in the pharmaceutical composition.

In illustrative embodiments, GELUCIRE 44/14 (lauroyl macrogol-32 glycerides EP, lauroyl polyoxyl-32 glycerides NF, lauroyl polyoxylglycerides (USA FDA IIG)) is heated to about 65° C. and CAPMUL MCM is heated to about 40° C. to facilitate mixing of the oil and non-ionic surfactant, although such heating is not necessary to dissolve the estradiol.

Specific Examples disclosed herein provide additional principles and embodiments illustrating the manufactures of the pharmaceutical compositions disclosed herein.

Delivery Vehicle

Generally, the pharmaceutical compositions described herein delivered intravaginally inside of a delivery vehicle, for example a capsule. According to embodiments, the capsules are soft capsules made of materials well known in the pharmaceutical arts, for example, gelatin. However, according to embodiments, the delivery vehicle is integral with the pharmaceutical composition (i.e., the pharmaceutical composition is the delivery vehicle). In such embodiments the pharmaceutical compositions is a gel, cream, ointment, tablet, or other preparation that is directly applied and absorbed vaginally.

According to embodiments, pharmaceutical compositions disclosed herein are contained in capsules, such as soft gelatin capsules. According to embodiments, the capsules contain one or more of the following: hydrophilic gel-forming bioadhesive (e.g., mucoadhesive) agents; a lipophilic agent; a gelling agent for the lipophilic agent, or a hydrodispersible agent. According to embodiments, the hydrophilic gel-forming bioadhesive agent is carboxyvinylic acid; hydroxypropylcellulose; carboxymethylcellulose; gelatin; xanthane gum; guar gum; aluminum silicate; or mixtures thereof. According to embodiments, the lipophilic agent is a liquid triglyceride; solid triglyceride (e.g., with a melting point of about 35° C.); carnauba wax; cocoa butter; or mixtures thereof. According to embodiments, the gelling agent is a hydrophobic colloidal silica. According to embodiments, the hydrodispersible agent is: polyoxyethylene glycol; polyoxyethylene glycol 7-glyceryl-cocoate; or mixtures thereof.

According to embodiments, the delivery vehicle is designed for ease of insertion. According to embodiments, the delivery vehicle is sized whereby it can be comfortably inserted into the vagina. According to embodiments, the delivery vehicle is prepared in a variety of geometries. For example, the delivery vehicle is shaped as a tear drop, a cone with frustoconical end, a cylinder, a cylinder with larger "cap" portion, or other shapes suitable for and that ease insertion into the vagina. According to embodiments, delivery vehicle is used in connection with an applicator. According to other embodiments, delivery vehicle is inserted digitally.

Figure 2:
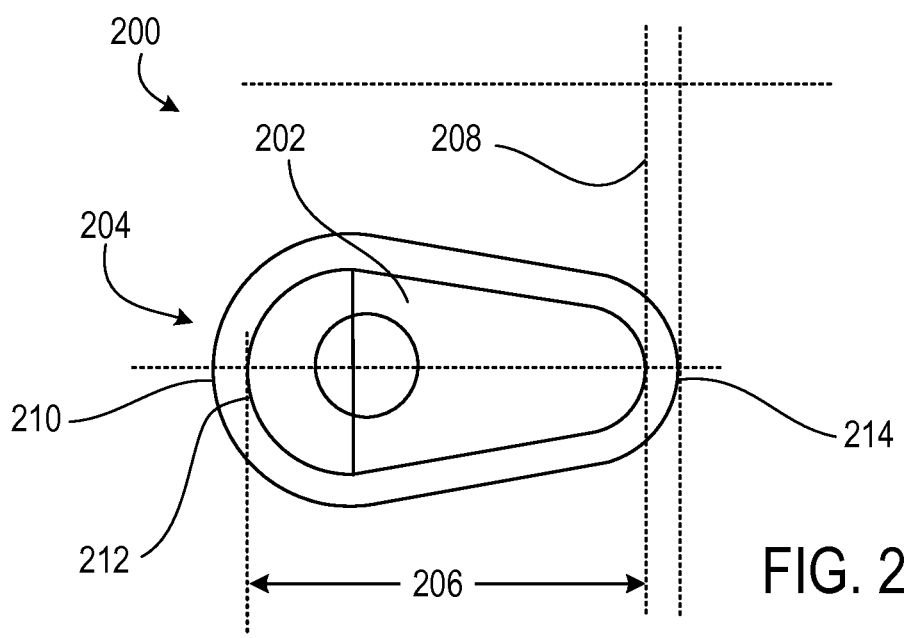
FIG. 2 illustrates a suppository in accordance with various embodiments of the invention.
Figure 3:
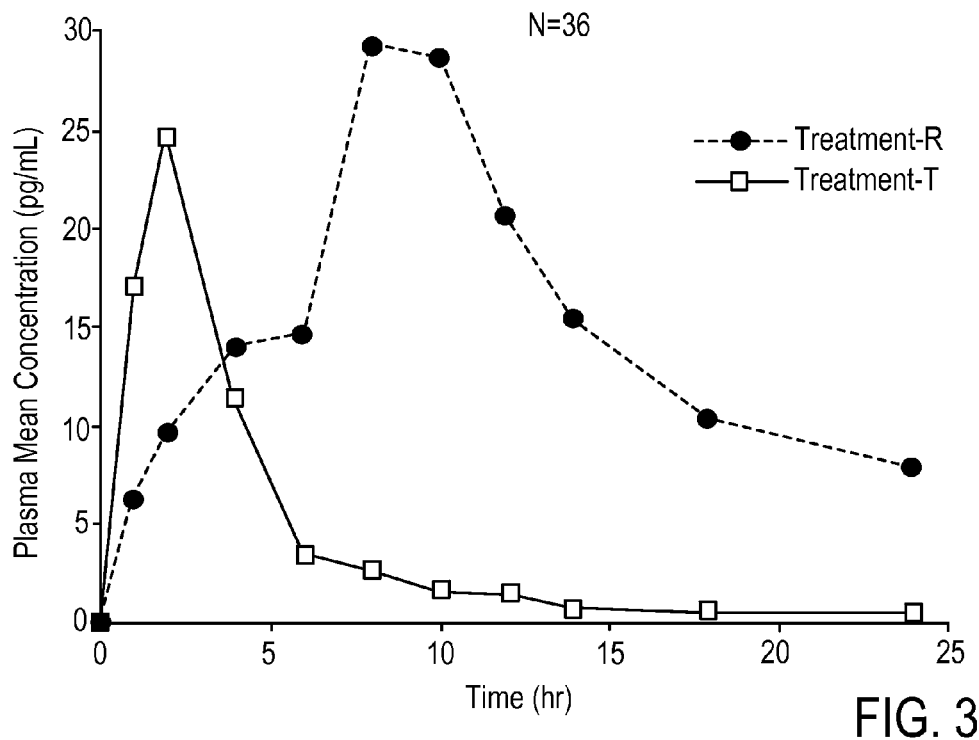
FIG. 3 is a linear plot of mean plasma estradiol-baseline adjusted concentrations versus time (N=36)
Figure 4:
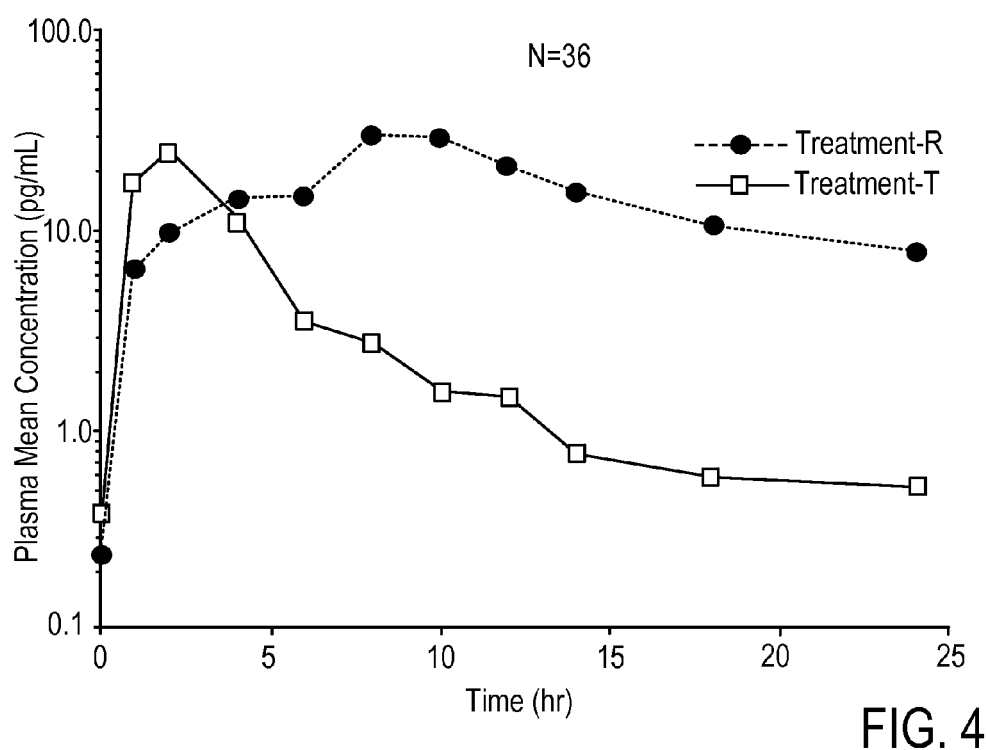
FIG. 4 is a semi-logarithmic plot of mean plasma estradiol-baseline adjusted concentrations versus time (N=36)
Figure 5:
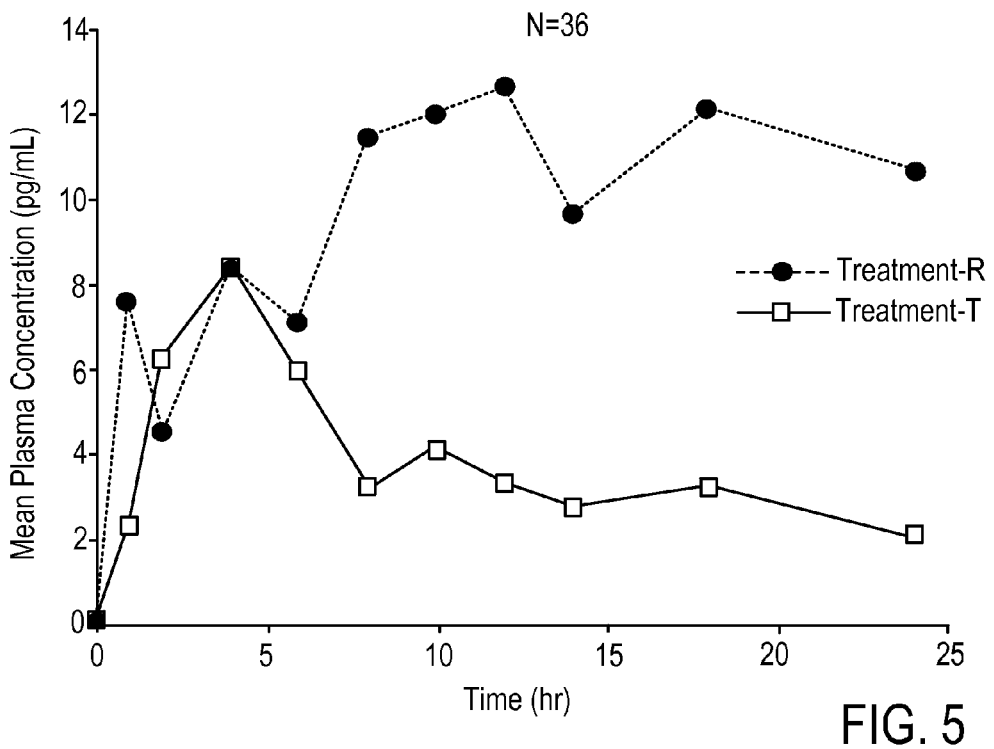
FIG. 5 is a linear plot of mean plasma estrone-baseline adjusted concentrations versus time (N=36)
Figure 6:
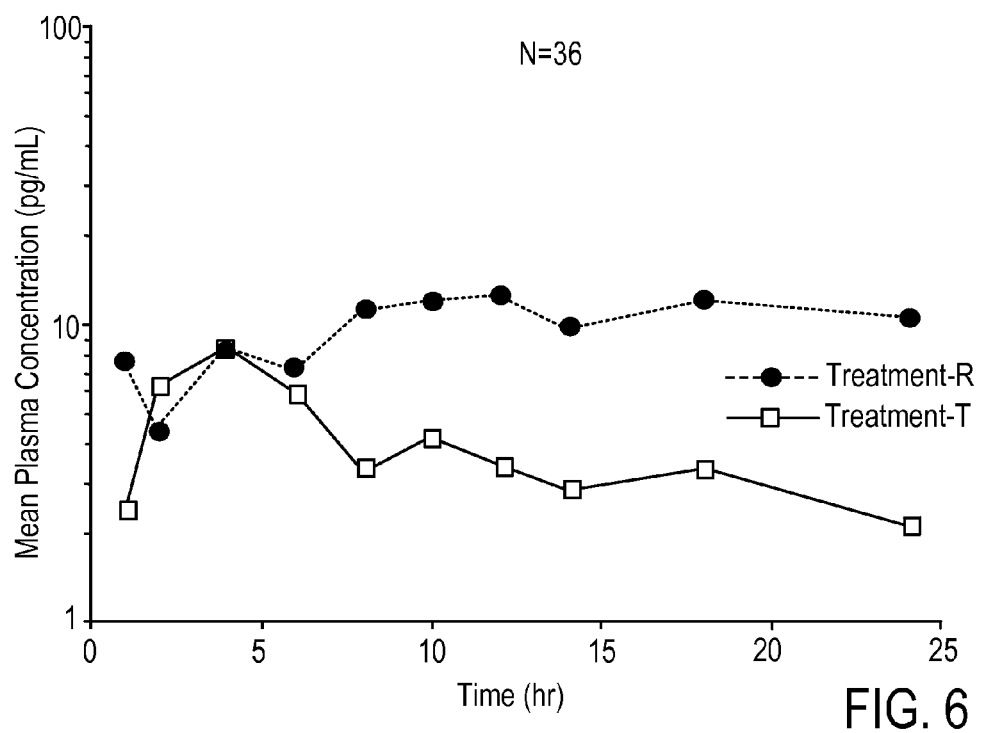
FIG. 6 is a semi-logarithmic plot of mean plasma estrone-baseline adjusted concentrations versus time (N=36)
Figure 7:
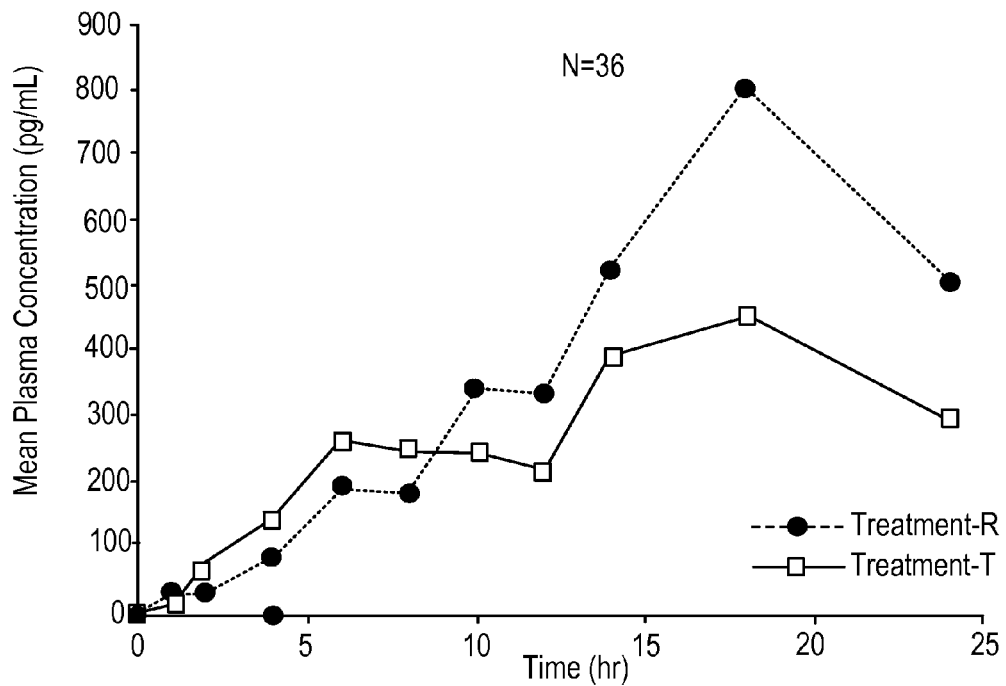
FIG. 7 is a linear plot of mean plasma estrone sulfate-baseline adjusted concentrations versus time (N=36)
Figure 8:
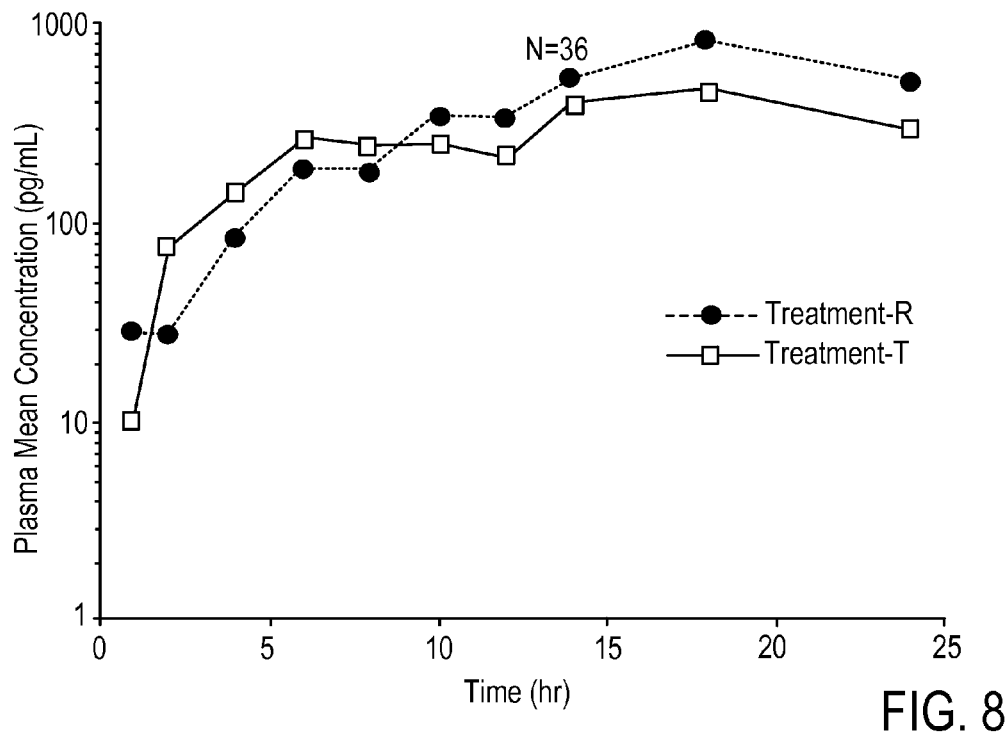
FIG. 8 is a semi-logarithmic plot of mean plasma estrone sulfate-baseline adjusted concentrations versus time (N=36)
Figure 9:
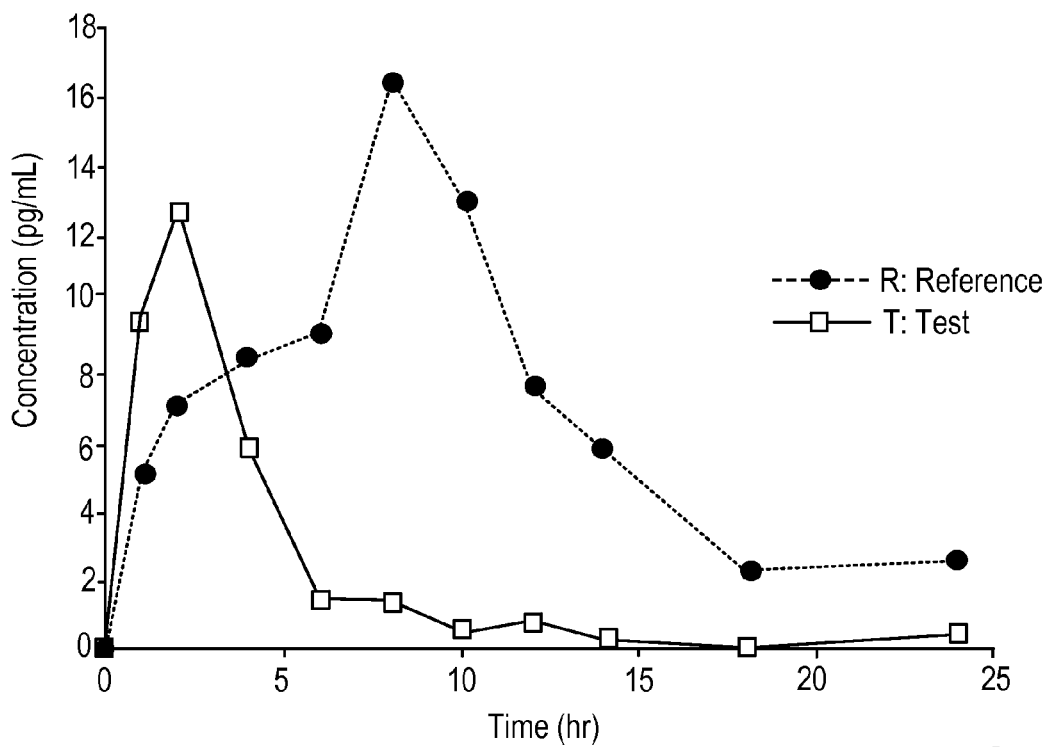
FIG. 9 is a linear plot of mean plasma estradiol-baseline adjusted concentrations versus time (N=34)
Figure 10:
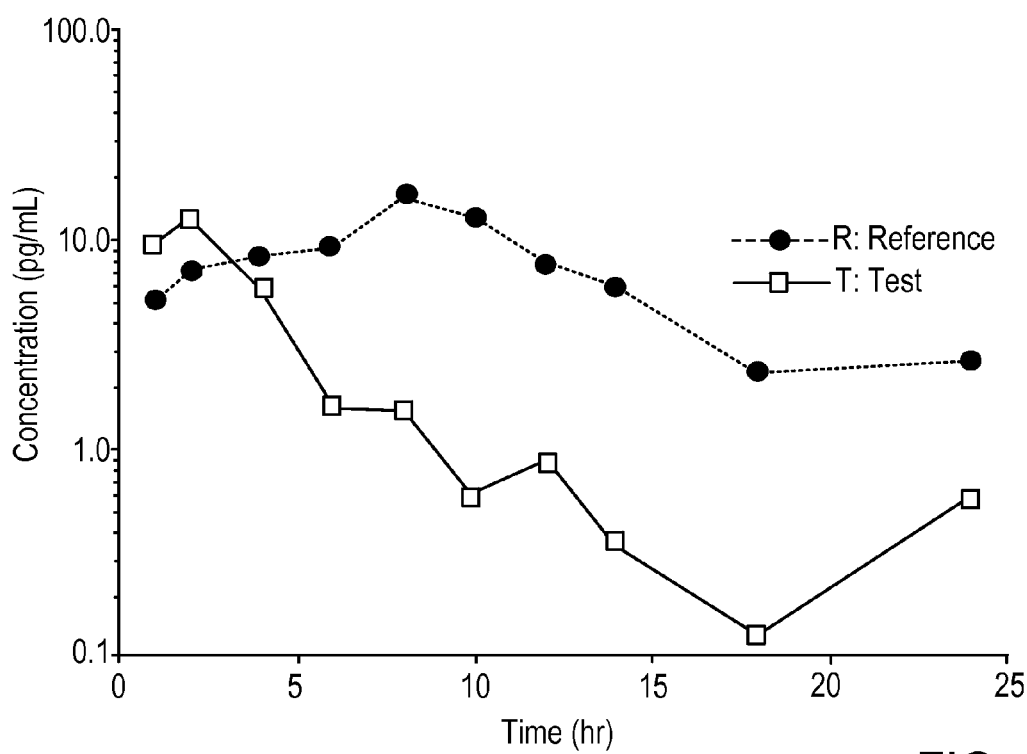
FIG. 10 is a semi-logarithmic plot of mean plasma estradiol-baseline adjusted concentrations versus time (N=34)
Figure 11:
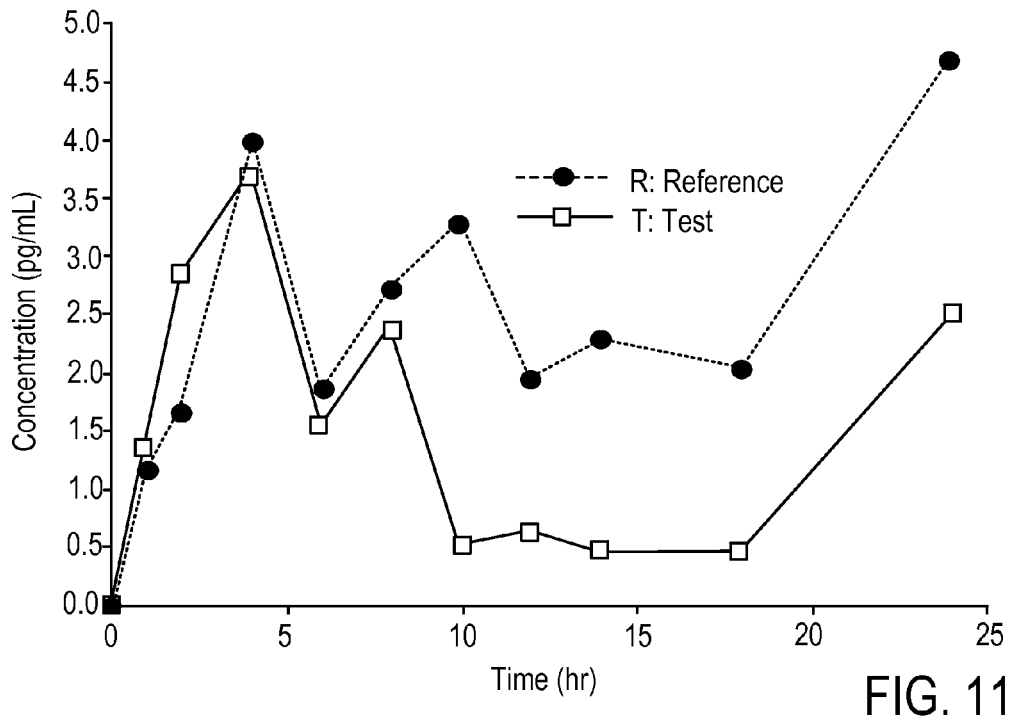
FIG. 11 is a linear plot of mean plasma estrone-baseline adjusted concentrations versus time (N=33)
Figure 12:
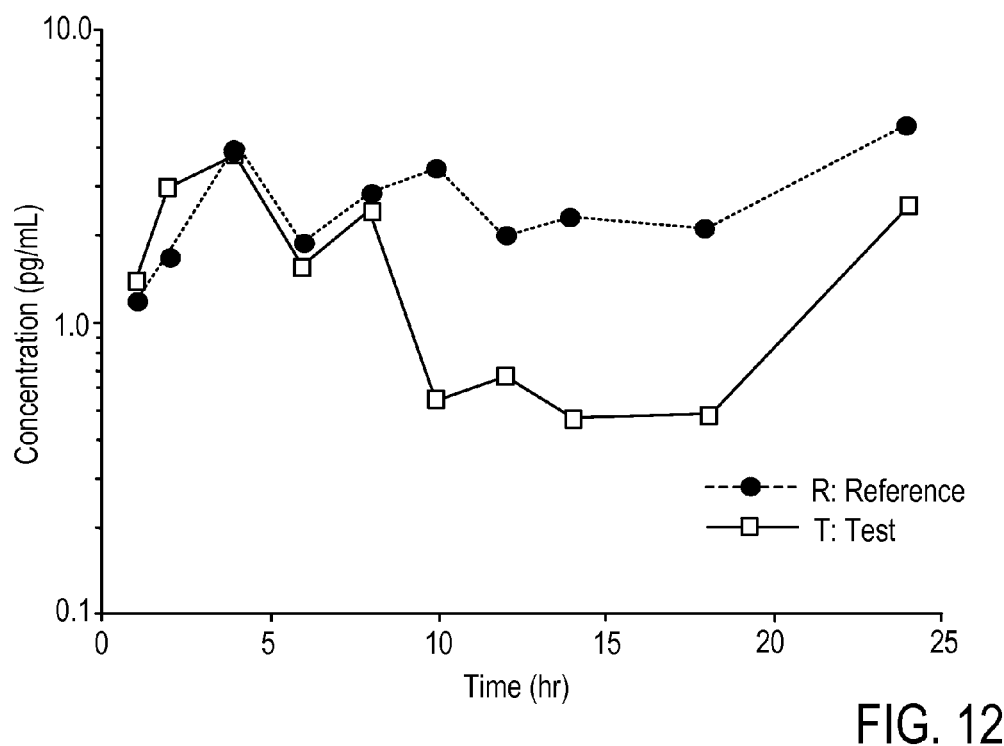
FIG. 12 is a semi-logarithmic plot of mean plasma estrone-baseline adjusted concentrations versus time (N=33)
Figure 13:
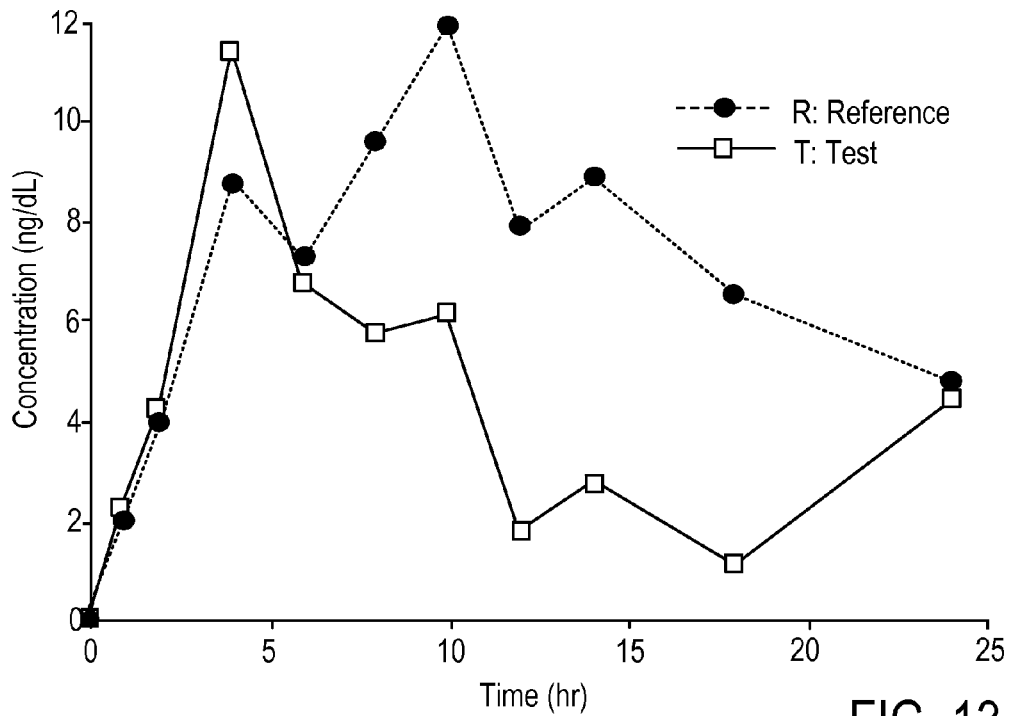
FIG. 13 is a linear plot of mean plasma estrone sulfate-baseline adjusted concentrations versus time (N=24)
Figure 14:
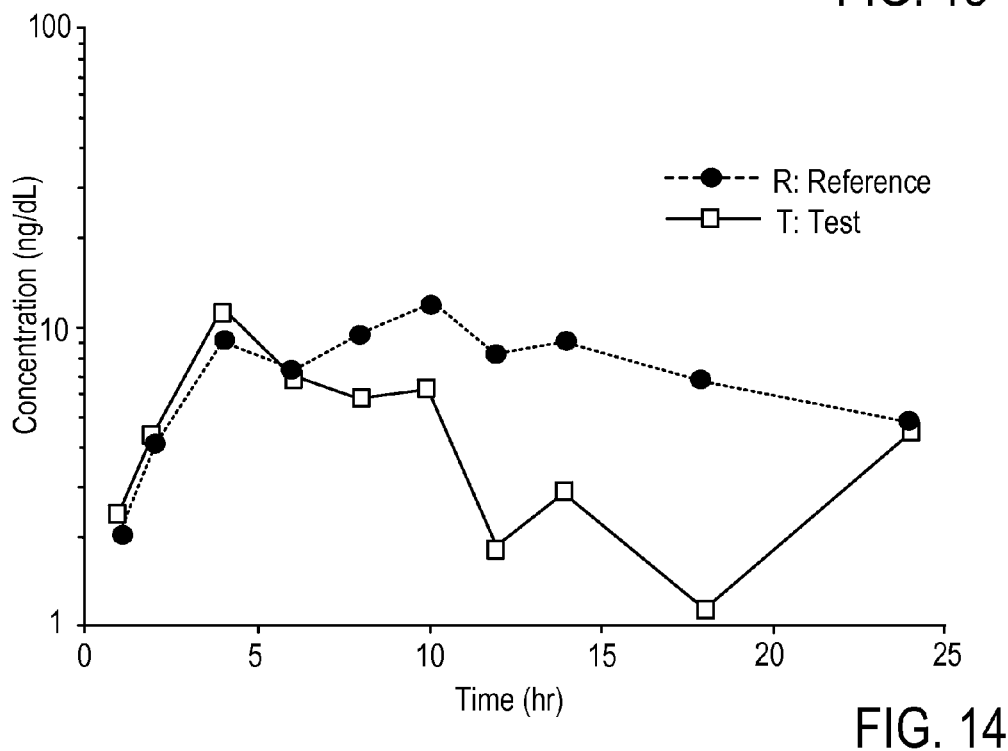
FIG. 14 is a semi-logarithmic plot of mean plasma estrone sulfate-baseline adjusted concentrations versus time (N=24).

With reference to FIG. 2, delivery vehicle 200 comprises pharmaceutical composition 202 and capsule 204. Width 208 represents the thickness of capsule 204, for example about 0.108 inches. The distance from one end of delivery vehicle 200 to another is represented by distance 206, for example about 0.690 inches. The size of delivery vehicle 200 may also be described by the arc swept by a radius of a given length. For example, arc 210, which is defined by the exterior of gelatin 204, is an arc swept by a radius of about 0.189 inches. Arc 212, which is defined by the interior of capsule 204, is an arc swept by a radius of about 0.0938 inches. Arc 214, which is defined by the exterior of gelatin 204 opposite arc 210, is an arc swept by a radius of about 0.108 inches. Suitable capsules of other dimensions may be provided. According to embodiments, capsule 204 has dimensions the same as or similar to the ratios as provided above relative to each other.

According to embodiments, the delivery vehicle is designed to remaining in the vagina until the pharmaceutical compositions are released. According to embodiments, delivery vehicle dissolves intravaginally and is absorbed into the vaginal tissue with the pharmaceutical composition, which minimizes vaginal discharge. In such embodiments, delivery mechanism is made from constituents that are non-toxic, for example, gelatin.

Design Factors for Vaginally Inserted Pharmaceutical Compositions

According to embodiments, the pharmaceutical composition is designed to maximize favorable characteristics that lead to patient compliance (patients that discontinue treatment prior to completion of the prescribed course of therapy), without sacrificing efficacy. Favorable characteristics include, for example, lack of or reduction of irritation relative to other hormone replacement pessaries, lack of or reduction in vaginal discharge of the pharmaceutical composition and delivery vehicle relative to other hormone replacement pessaries, lack of or reduction of pharmaceutical composition or delivery vehicle residue inside the vagina, ease of administration compared to other hormone replacement pessaries, or improved efficacy of drug product relative to otherwise similar pharmaceutical compositions.

According to embodiments, the pharmaceutical composition is non-irritating or minimizes irritation. Patient irritation comprises pain, pruritis (itching), soreness, excessive discharge, swelling, or other similar conditions. Patient irritation results in poor compliance. Non-irritating or reduced irritation pharmaceutical compositions are measured relative to competing hormone pessaries, including tablets, creams, or other intravaginal estrogen delivery forms.

According to embodiments, the pharmaceutical compositions does not result in systemic exposure (e.g., blood circulation of estradiol), which improves safety. According to other embodiments, the pharmaceutical compositions disclosed herein result in significantly reduced systemic exposure (e.g., blood circulation of estradiol) when compared to RLDs.

According to embodiments, the pharmaceutical composition does not leave residue inside the vagina. Rather, the pharmaceutical composition and delivery vehicle are substantially absorbed or dispersed without resulting in unabsorbed residue or unpleasant sensations of non-absorbed or non-dispersed drug product. Measurement of lack of residue is relative to other vaginally inserted products or can be measured objectively with inspection of the vaginal tissues. For example, certain other vaginally inserted products contain starch which can result in greater discharge from the vagina following administration than. In some embodiments, the pharmaceutical compositions provided herein provide a lower amount, duration, or frequency of discharge following administration compared to other vaginally inserted products (e.g., compressed tablets).

According to embodiments, the pharmaceutical composition improves vaginal discharge compared to other pessaries, including pessaries that deliver hormones. Ideally, vaginal discharge is eliminated, minimized, or improved compared to competing products.

According to embodiments, the pharmaceutical compositions disclosed herein are inserted digitally. According to embodiments, the pharmaceutical compositions are digitally inserted approximately two inches into the vagina without a need for an applicator. According to embodiments, the pharmaceutical compositions are designed to be also inserted with an applicator, if desired. According to some embodiments, because the site of VVA is in the proximal region of the vagina (towards the vaginal opening), the pharmaceutical compositions disclosed herein are designed to be inserted in the proximal portion of the vagina.

Through extensive experimentation, various medium chain fatty acid esters of glycerol and propylene glycol demonstrated one or more favorable characteristics for development as a human drug product. According to embodiments, the solubilizing agent was selected from at least one of a solvent or co-solvent. Suitable solvents and co-solvents include any mono-, di- or triglyceride and glycols, and combinations thereof.

According to embodiments, the pharmaceutical composition is delivered via a gelatin capsule delivery vehicle. According to these embodiments, the pharmaceutical composition is a liquid pharmaceutical composition. According to embodiments, the delivery vehicle is a soft capsule, for example a soft gelatin capsule. Thus, the pharmaceutical composition of such embodiments is encapsulated in the soft gelatin capsule or other soft capsule.

According to embodiments, the pharmaceutical composition comprises estradiol that is at least about 80% solubilized in a solubilizing agent comprising one or more C6 to C14 medium chain fatty acid mono-, di-, or triglycerides and, optionally, a thickening agent. According to embodiments, the pharmaceutical composition comprises estradiol that is at least about 80% solubilized one or more C6 to C12 medium chain fatty acid mono-, di-, or triglycerides, e.g., one or more C6 to C14 triglycerides, e.g., one or more C6 to C12 triglycerides, such as one or more C8-C10 triglycerides. These embodiments specifically contemplate the estradiol being at least 80% solubilized. These embodiments specifically contemplate the estradiol being at least 90% solubilized. These embodiments specifically contemplate the estradiol being at least 95% solubilized. These embodiments specifically contemplate the estradiol being fully solubilized.

As noted above, liquid pharmaceutical compositions are liquid at room temperature or at body temperature. For example, in some embodiments, a pharmaceutical composition provided herein is a liquid formulation contained within a soft gel capsule. Gels, hard fats, or other solid forms that are not liquid at room or body temperature are less desirable in embodiments of the pharmaceutical composition that are liquid.

The thickening agent serves to increase viscosity, e.g., up to about 10,000 cP (10,000 mPa-s), typically to no more than about 5000 cP, and more typically to between about 50 and 1000 cP. In embodiments, the non-ionic surfactant, e.g., GELUCIRE or TEFOSE, may be solid at room temperature and require melting to effectively mix with the solubilizing agent. However, in these embodiments, the resultant pharmaceutical composition remains liquid, albeit with greater viscosity, not solid.

According to embodiments, the pharmaceutical composition comprises estradiol, the medium chain solubilizing agent, and the thickening agent as the ingredients delivered via a soft capsule delivery vehicle. Other ingredients, e.g., colorants, antioxidants, preservatives, or other ingredients may be included as well. However, the addition of other ingredients should be in amounts that do not materially change the solubility of the estradiol, the pharmacokinetics of the pharmaceutical composition, or efficacy of the pharmaceutical composition. Other factors that should be considered when adjusting the ingredients of the pharmaceutical composition include the irritation, vaginal discharge, intravaginal residue, and other relevant factors, for example those that would lead to reduced patient compliance. Other contemplated ingredients include: oils or fatty acid esters, lecithin, mucoadherent agents, gelling agents, dispersing agents, or the like.

Methods

According to embodiments, the pharmaceutical compositions disclosed herein can be used for the treatment of VVA, including the treatment of at least one VVA symptom including: vaginal dryness, vaginal or vulvar irritation or itching, dysuria, dyspareunia, and vaginal bleeding associated with sexual activity, among others. According to embodiments the methods of treatment are generally applicable to females.

According to embodiments, the pharmaceutical compositions disclosed herein can be used for the treatment of estrogen-deficient urinary states. According to embodiments, the pharmaceutical compositions disclosed herein can be used for the treatment of dysparuenia, or vaginal bleeding associated with sexual activity.

According to embodiments, treatment of the VVA, estrogen-deficient urinary states, and dysparuenia and vaginal bleeding associated with sexual activity occurs by administering the pharmaceutical compositions intravaginally. According to embodiments where the delivery vehicle is a capsule, the patient obtains the capsule and inserts the capsule into vagina, where the capsule dissolves and the pharmaceutical composition is releases into the vagina where it is absorbed into the vaginal tissue. In some embodiments, the pharmaceutical composition is completely absorbed into the vaginal tissue. In some embodiments, the pharmaceutical composition is substantially absorbed into the vaginal tissue (e.g., at least about 80% by weight, at least about 85% by weight, at least about 90% by weight, at least about 95% by weight, at least about 97% by weight, at least about 98% by weight, or at least about 99% by weight of the composition is absorbed). According to embodiments, the capsule is inserted about two inches into the vagina digitally, however the depth of insertion is generally any depth that allows for adsorption of substantially all of the pharmaceutical composition. According to embodiments, the capsule can also be applied using an applicator that deposits the capsule at an appropriate vaginal depth as disclosed herein.

According to embodiments where the pharmaceutical composition is a cream, gel, ointment, or other similar preparation, the pharmaceutical composition is applied digitally, as is well known and understood in the art.

Upon release of the pharmaceutical composition in the vagina, estradiol is locally absorbed. For example, following administration of the pessary to the proximal region of the vagina of a patient provides a therapeutically effective concentration of estradiol over 24 hours in the proximal region of the vagina.

According to embodiments, the timing of administration of the pharmaceutical composition of this disclosure may be conducted by any safe means as prescribed by an attending physician. According to embodiments, a patient will administer the pharmaceutical composition (e.g., a capsule) intravaginally each day for 14 days, then twice weekly thereafter.

According to embodiments, the pharmaceutical compositions are vaginally administered with co-administration of an orally administered estrogen-based (or progestin-based or progestin- and estrogen-based) pharmaceutical drug product, or patch, cream, gel, spray, transdermal delivery system or other parenterally-administered estrogen-based pharmaceutical drug product, each of which can include natural, biosimilar, or synthetic or other derived estrogens or progestins. According to embodiments, modulation of circulating estrogen levels provided via the administration of the pharmaceutical compositions disclosed herein, if any, are not intended to be additive to any co-administered estrogen product and its associated circulating blood levels. According to other embodiments, co-administrated estrogen products are intended to have an additive effect as would be determined by the patient physician.

According to embodiments, the efficacy and safety of the pharmaceutical compositions described herein in the treatment of the symptoms of VVA may be determined. According to embodiments, the size, effect, cytology, histology, and variability of the VVA may be determined using various endpoints to determine efficacy and safety of the pharmaceutical compositions described herein or as otherwise accepted in the art, at present or as further developed. On source of endpoints is with the US Food and Drug Administration's (FDA) published guidelines for treatment of VVA with estradiol.

Measurement of Efficacy

According to embodiments, administration of the pharmaceutical compositions described herein resulted in treatment of the VVA, as well as improvement of one or more of the associated symptoms. Patients with VVA experience shrinking of the vaginal canal in both length and diameter and the vaginal canal has fewer glycogen-rich vaginal cells to maintain moisture and suppleness. In addition, the vaginal wall can become thin, pale, dry, or sometimes inflamed (atrophic vaginitis). These changes can manifest as a variety of symptoms collectively referred to as VVA. Such symptoms include, without limitations, an increase in vaginal pH; reduction of vaginal epithelial integrity, vaginal secretions, or epithelial surface thickness; pruritis; vaginal dryness; dyspareunia (pain or bleeding during sexual intercourse); urinary tract infections; or a change in vaginal color. According to embodiments, efficacy is measured as a reduction of vulvar and vaginal atrophy in a patient back to premenopausal conditions. According to embodiments, the change is measured as a reduction in the severity of one or more atrophic effects measured at baseline (screening, Day 1) and compared to a measurement taken at Day 15 (end of treatment). Severity of the atrophic effect may be measured using a scale of 0 to 3 where, for example, none=0, mild=1, moderate=2, or severe=3. Such scoring is implemented to evaluate the pre-treatment condition of patients; to determine the appropriate course of a treatment regime; such as dosage, dosing frequency, and duration, among others; and post-treatment outcomes.

One of the symptoms of VVA is increased vaginal pH. In further aspects of this disclosure, treatment with the pharmaceutical compositions described herein resulted in a decrease in vaginal pH. A decrease in vaginal pH is measured as a decrease from the vaginal pH at baseline (screening) to the vaginal pH at Day 15, according to embodiments. In some embodiments, a pH of 5 or greater may be associated with VVA. In some embodiments, pH is measured using a pH indicator strip placed against the vaginal wall. In some embodiments, a change in vaginal pH is a change in a patient's vaginal pH to a pH of less than about pH 5.0. In some embodiments, a subject's vaginal pH may be less than about pH 4.9, pH 40.8, pH 4.7, pH 40.6, pH 4.5, pH 4.4, pH 4.3, pH 40.2, pH 4.1, pH 4.0, pH 3.9, pH 3.8, pH 3.7, pH 3.6, or pH 3.5.

According to embodiments, treatment with the pharmaceutical compositions described herein resulted in improvements in the vaginal Maturation Index. The Maturation Index is measured as a change in cell composition. According to embodiments and as related to VVA, a change in cell composition is measured as the change in percent of composition or amount of parabasal vaginal cells, intermediate cells, and superficial vaginal cells, such as a change in the composition or amount of parabasal vaginal cells compared with or, relative to, a change in superficial vaginal cells. A subject having VVA symptoms often has an increased number of parabasal cells and a reduced number of superficial cells (e.g., less than about 5%) compared with women who do not suffer from VVA. Conversely, a subject having decreasing VVA symptoms, or as otherwise responding to treatment, may demonstrate an improvement in the Maturation Index, specifically a decrease in the amount of parabasal cells or an increase in the amount of superficial cells compared to baseline (screening). In embodiments, a decrease in parabasal cells is measured as a reduction in the percent of parabasal cells; the percent reduction may be at least about an 85%, 80%, 75%, 70%, 65%, 60%, 55%, 50%, 45%, 40%, 35%, 30%, 25%, 20%, 15% or 10% reduction in the number of parabasal cells. In embodiments, a percent reduction may be at least about a 54% reduction in the number of parabasal cells. In embodiments, an increase in superficial cells is measured as an increase in the percent of superficial cells; the percent increase in superficial cells may be at least about 5%, 10%, 15%, 20%, 25%, 30%, 35%, 40%, 45%, or 50% increase in the number of superficial cells. In further embodiments, a percent increase may be at least about a 35% increase in the number of superficial cells.

In some embodiments, an improvement in the Maturation Index is assessed as a change over time. For example, as a change in cell composition measured at a baseline (screening) at Day 1 compared to the cell composition measured at Day 15. The change in cell composition may also be assessed as a change in the amount of parabasal cells over time, optionally in addition to measuring changes in parabasal cells and superficial cells as described above. Such cells may be obtained from the vaginal mucosal epithelium through routine gynecological examination and examined by means of a vaginal smear.

In various further aspects of this disclosure, treatment with the pharmaceutical compositions described herein resulted in any of: an increase in superficial cells; a decrease in parabasal cells; and an increase in intermediate cells.

In further aspects of this disclosure, samples may be collected to determine hormone levels, in particular, estradiol levels. In some embodiments, blood samples may be taken from a subject and the level of estradiol measured (pg/ml). In some embodiments, estradiol levels may be measured at 0 hours (for example, at time of first treatment), at 1 hour (for example, post first treatment), at 3 hours, and at 6 hours. In some embodiments, samples may be taken at day 8 (for example, post first treatment) and at day 15 (for example, one day post the last treatment on day 14). In some embodiments, descriptive statistics of plasma estradiol concentrations at each sampling time and observed $C_{max}$ and $T_{max}$ values may be measured and the AUC calculated.

In some embodiments, a pessary can comprise about 25 μg of estradiol. In such cases, administration of the pessary to a patient can provide, in a plasma sample from the patient, parameters including one or more parameters selected from: 1) a corrected geometric mean peak plasma concentration ($C_{max}$) of estradiol of about 19 pg*hr/ml to about 29 pg*hr/ml (e.g., 19.55 pg*hr/ml to about 28.75 pg*hr/ml); or 2) a corrected geometric mean area under the curve $(AUC)_{0-24}$ of estradiol of about 75 pg*hr/ml to about 112 pg*hr/ml (e.g., 75.82 pg*hr/ml to about 111.50). In some embodiments, administration of the pessary to a patient provides, in a plasma sample from the patient, one or more parameters selected from: 1) a corrected geometric mean peak plasma concentration ($C_{max}$) of estrone of about 9 pg*hr/ml to about 14 pg*hr/ml (e.g., 9.17 pg*hr/ml to about 13.49 pg*hr/ml); and 2) a corrected geometric mean area under the curve $(AUC)_{0-24}$ of estrone of about 43 pg*hr/ml to about 65 pg*hr/ml (e.g., 43.56 pg*hr/ml to about 64.06 pg*hr/ml). In some embodiments, administration of the pessary to a patient provides, in a plasma sample from the patient, provides one or more parameters selected from: 1) a corrected geometric mean peak plasma concentration ($C_{max}$) of estrone sulfate of about 416 pg*hr/ml to about 613 pg*hr/ml (e.g., 416.53 pg*hr/ml to about 612.55 pg*hr/ml); and 2) a corrected geometric mean area under the curve $(AUC)_{0-24}$ of estrone sulfate of about 3598 pg*hr/ml to about 5291 pg*hr/ml (e.g., 3598.04 pg*hr/ml to about 5291.24 pg*hr/ml).

In some embodiments, a pessary can comprise about 10 μg of estradiol. In such cases, administration of the pessary to a patient can provide, in a plasma sample from the patient, one or more parameters selected from: 1) a corrected geometric mean peak plasma concentration ($C_{max}$) of estradiol of about 12 pg*hr/ml to about 18 pg*hr/ml (e.g., 12.22 pg*hr/ml to about 17.98 pg*hr/ml); 2) a corrected geometric mean area under the curve $(AUC)_{0-24}$ of estradiol of about 42 pg*hr/ml to about 63 pg*hr/ml (e.g., 42.18 pg*hr/ml to about 62.02 pg*hr/ml); and 3) a corrected geometric mean time to peak plasma concentration ($T_{max}$) of estradiol of about 1 hrs to about 3 hrs (e.g., 1.49 hrs to about 2.19 hrs). In some embodiments, administration of the pessary to a patient provides, in a plasma sample from the patient, one or more parameters selected from: 1) a corrected geometric mean peak plasma concentration ($C_{max}$) of estrone of about 4 pg*hr/ml to about 7 pg*hr/ml (e.g., 4.38 pg*hr/ml to about 6.44 pg*hr/ml); 2) a corrected geometric mean area under the curve $(AUC)_{0-24}$ of estrone of about 20 pg*hr/ml to about 31 pg*hr/ml (e.g., 20.60 pg*hr/ml to about 30.30 pg*hr/ml); and 3) a corrected geometric mean time to peak plasma concentration ($T_{max}$) of estrone of about 4 hrs to about 8 hrs (e.g., 4.99 hrs to about 7.34 hrs). In some embodiments, administration of the pessary to a patient provides, in a plasma sample from the patient, one or more parameters selected from: 1) a corrected geometric mean peak plasma concentration ($C_{max}$) of estrone sulfate of about 10 pg*hr/ml to about 16 pg*hr/ml (e.g., 10.34 pg*hr/ml to about 15.20 pg*hr/ml); 2) a corrected geometric mean area under the curve $(AUC)_{0-24}$ of estrone sulfate of about 56 pg*hr/ml to about 84 pg*hr/ml (e.g., 56.61 pg*hr/ml to about 83.25 pg*hr/ml); and 3) a corrected geometric mean time to peak plasma concentration ($T_{max}$) of estrone sulfate of about 4 hrs to about 7 hrs (e.g., 40.67 hrs to about 6.86 hrs).

In some embodiments, a pessary can comprise about 4 μg of estradiol. In such cases, administration of the pessary to a patient can provide, in a plasma sample from the patient, one or more parameters selected from: 1) a corrected geometric mean peak plasma concentration ($C_{max}$) of estradiol of about 4 pg*hr/ml to about 8 pg*hr/ml; 2) a corrected geometric mean area under the curve $(AUC)_{0-24}$ of estradiol of about 16 pg*hr/ml to about 26 pg*hr/ml; and 3) a corrected geometric mean time to peak plasma concentration ($T_{max}$) of estradiol of about 0.25 hrs to about 2 hrs. In some embodiments, administration of the pessary to a patient provides, in a plasma sample from the patient, one or more parameters selected from: 1) a corrected geometric mean peak plasma concentration ($C_{max}$) of estrone of about 1 pg*hr/ml to about 3 pg*hr/ml; 2) a corrected geometric mean area under the curve $(AUC)_{0-24}$ of estrone of about 8 pg*hr/ml to about 13 pg*hr/ml; and 3) a corrected geometric mean time to peak plasma concentration ($T_{max}$) of estrone of about 1 hrs to about 4 hrs. In some embodiments, administration of the pessary to a patient provides, in a plasma sample from the patient, one or more parameters selected from: 1) a corrected geometric mean peak plasma concentration ($C_{max}$) of estrone sulfate of about 4 pg*hr/ml to about 7 pg*hr/ml; 2) a corrected geometric mean area under the curve $(AUC)_{0-24}$ of estrone sulfate of about 22 pg*hr/ml to about 34 pg*hr/ml; and 3) a corrected geometric mean time to peak plasma concentration ($T_{max}$) of estrone sulfate of about 1 hrs to about 3 hrs.

A pharmaceutical composition provided herein can result in substantially local delivery of estradiol. For example, plasma concentrations of estradiol, estrone, and estrone sulfate measured in the plasma of a patient following administration of a pharmaceutical composition as provided herein be statistically similar to those measured following administration of a placebo formulation (i.e. a similar formulation lacking the estradiol). Accordingly, in some embodiments, the plasma concentrations of estradiol, estrone, or estrone sulfate measured following administration of a pharmaceutical composition provided herein may be low compared to RLD formulations.

In some embodiments, a pessary can include about 1 μg to about 25 μg of estradiol. Upon administration the pessary to a patient, a plasma sample from the patient can provide a corrected geometric mean peak plasma concentration ($C_{max}$) of estradiol that is less than about 30 pg*hr/ml. For example, administration of the pessary to a patient provides a corrected geometric mean peak plasma concentration ($C_{max}$) of estradiol that is less than about 18 pg*hr/ml. In some embodiments, administration of the pessary to a patient provides a corrected geometric mean area under the curve $(AUC)_{0-24}$ of estradiol that is less than about 112 pg*hr/ml. For example, administration of the pessary to a patient provides a corrected geometric mean area under the curve $(AUC)_{0-24}$ of estradiol that is less than about 63 pg*hr/ml.

In some embodiments, administration of the pessary to a patient provides a corrected geometric mean peak plasma concentration ($C_{max}$) of estrone that is less than about 14 pg*hr/ml. For example, administration of the pessary to a patient provides a corrected geometric mean peak plasma concentration ($C_{max}$) of estrone that is less than about 7 pg*hr/ml. In some embodiments, administration of the pessary to a patient provides a corrected geometric mean area under the curve ($AUC)_{0-24}$ of estrone that is less than about 65 pg*hr/ml. For example, administration of the pessary to a patient provides a corrected geometric mean area under the curve ($AUC)_{0-24}$ of estrone that is less than about 31 pg*hr/ml.

In some embodiments, administration of the pessary to a patient provides a corrected geometric mean peak plasma concentration ($C_{max}$) of estrone sulfate that is less than about 613 pg*hr/ml. For example, administration of the pessary to a patient provides a corrected geometric mean peak plasma concentration ($C_{max}$) of estrone sulfate that is less than about 16 pg*hr/ml. In some embodiments, administration of the pessary to a patient provides a corrected geometric mean area under the curve ($AUC)_{0-24}$ of estrone sulfate that is less than about 5291 pg*hr/ml. For example, administration of the pessary to a patient provides a corrected geometric mean area under the curve ($AUC)_{0-24}$ of estrone sulfate that is less than about 84 pg*hr/ml.

In further aspects of this disclosure, capsule disintegration may be determined. In some embodiments, delivery vehicle disintegration or absorption (presence or absence of the delivery vehicle after administration) at day 1 of treatment (for example, at 6 hours post first treatment) and at day 15 (for example, one day post the last treatment on day 14).

Statistical Measurements

According to embodiments, pharmacokinetics of the pharmaceutical composition disclosed herein are measured using statistical analysis. According to embodiments, Analysis of Variance ("ANOVA") or Analysis of CoVariance ("ANCOVA") are used to evaluate differences between a patient receiving treatment with a pharmaceutical composition comprising an active pharmaceutical composition (for example, a pharmaceutical composition comprising estradiol) and a patient receiving treatment with a placebo (for example, the same pharmaceutical composition but without estradiol) or a reference drug. A person of ordinary skill in the art will understand how to perform statistical analysis of the data collected.

EXAMPLES

The following examples are of pharmaceutical compositions, delivery vehicles, and combinations thereof. Methods of making are also disclosed. Data generated using the pharmaceutical compositions disclosed herein are also disclosed.

Example 1

Pharmaceutical Composition

In embodiments, estradiol is procured and combined with one or more pharmaceutically acceptable solubilizing agents. The estradiol is purchased as a pharmaceutical grade ingredient, often as micronized estradiol, although other forms can also be used. In embodiments, the pharmaceutical composition comprises estradiol in a dosage strength of from about 1 µg to about 50 µg. In embodiments, the pharmaceutical composition comprises 10 µg of estradiol. In embodiments, the pharmaceutical composition comprises 25 µg of estradiol.

In embodiments, the estradiol is combined with pharmaceutically acceptable solubilizing agents, and, optionally, other excipients, to form a pharmaceutical composition. In embodiments, the solubilizing agent is one or more of CAPMUL MCM, MIGLYOL 812, GELUCIRE 39/01, GELUCIRE 43/01, GELUCIRE 50/13, and TEFOSE 63.

GELUCIRE 39/01 and GELUCIRE 43/01 each have an HLB value of 1. GELUCIRE 50/13 has an HLB value of 13. TEFOSE 63 has an HLB value of between 9 and 10.

Various combinations of pharmaceutically acceptable solubilizing agents were combined with estradiol and examined as shown in Table 1.

TABLE 1

Capmul MCM ("MCM"), Gelucire 39/01 ("39/01"), Gelucire 43/01("43/01"), Gelucire 50/13("50/13"), and Tefose ("Tefose 63")

| # | Vehicle system | Ratio | Physical state @ Room Temperature | Physical state @ 37° C. after ~30 minutes | Viscosity (cps) | Melting Time @ 37° C. | Dispersion in water 37° C. |
|---|---|---|---|---|---|---|---|
| 1 | MCM:39/01 | 8:2 | Solid | Clear liquid | 50 @ 37° C. | Start: 6 min Finish: 12 min | Small oil drops on top |
| 2 | MCM:39/01 | 7:3 | Solid | Clear liquid | | Start: 9 min Finish: 19 min | |
| 3 | MCM:39/01 | 6:4 | Solid | Clear liquid | | Start: 20 min Finish: 32 min | |
| 4 | MCM:43/01 | 8:2 | Solid | Liquid with solid particles | | | |
| 5 | MCM:43/01 | 7:3 | Solid | Liquid with solid particles | | | |
| 6 | MCM:50/13 | 9:1 | Liquid/ cloudy | Liquid/cloudy | 140@ 25° C. | Clear after 20 min | Uniformly cloudy dispersion |
| 7 | MCM:50/13 | 8:2 | Liquid/ cloudy | Liquid/cloudy | 190@ 25° C. | | Uniformly cloudy dispersion |
| 8 | MCM:50/13 | 7:3 | Semisolid | Semisolid | | | |
| 9 | MCM:TEFOSE 63 | 9:1 | Semisolid | Liquid/cloudy | 150@ 25° C. | Start: 1 min Finish: 5 min | Uniformly cloudy dispersion |

TABLE 1-continued

Capmul MCM ("MCM"), Gelucire 39/01 ("39/01"), Gelucire 43/01("43/01"), Gelucire 50/13("50/13"), and Tefose ("Tefose 63")

| # | Vehicle system | Ratio | Physical state @ Room Temperature | Physical state @ 37° C. after ~30 minutes | Viscosity (cps) | Melting Time @ 37° C. | Dispersion in water 37° C. |
|---|---|---|---|---|---|---|---|
| 10 | MCM:TEFOSE 63 | 8:2 | Semisolid | Semisolid | 240@ 25° C. | | Uniformly cloudy dispersion |
| 11 | MCM:TEFOSE 63 | 7:3 | Semisolid | Semisolid | 380@ 25° C. | Semisolid after 30 min at 37° C., doesn't melt at 41° C. | Uniformly cloudy dispersion |
| 12 | MIGLYOL 812:50/13 | 9:1 | Semisolid | Semisolid | 140@ 25° C. | | 2 phases, oil on top |
| 13 | MIGLYOL 812:TEFOSE 63 | 9:1 | Liquid/cloudy | Liquid/cloudy | 90@ 25° C. | Start: 1 min Finish: 5 min | 2 phases, oil on top |

Pharmaceutical compositions in Table 1 that were liquid or semisolid at room temperature were tested using a Brookfield viscometer (Brookfield Engineering Laboratories, Middleboro, Mass.) at room temperature. Pharmaceutical compositions appearing in Table 1 that were solid at ambient temperature were tested using a Brookfield viscometer at 37° C.

Pharmaceutical compositions appearing in Table 1 that were solid at room temperature were assessed at 37° C. to determine their melting characteristics. The viscosity of the gels can be important during encapsulation of the formulation. For example, in some cases, it is necessary to warm the formulation prior to filing of the gelatin capsules. In addition, the melting characteristics of the composition can have important implications following administration of the formulation into the body. For example, in some embodiments, the formulation will melt at temperatures below about 37° C. Pharmaceutical Composition 11 (Capmul MCM/Tefose 63), for example, did not melt at 37° C. or 41° C.

A dispersion assessment of the pharmaceutical compositions appearing in Table 1 was performed. The dispersion assessment was performed by transferring 300 mg of each vehicle system in 100 ml of 37° C. water, without agitation, and observing for mixing characteristics. Results varied from formation of oil drops on the top to separation of phases to uniform, but cloudy dispersions. Generally speaking, it is believed that formulations able to readily disperse in aqueous solution will have better dispersion characteristics upon administration. It was surprisingly found, however, as shown below in Examples 7-9, that formulations that did not readily disperse in aqueous solution (e.g., Formulation 13) and instead formed two phases upon introduction to the aqueous solution were found to be the most effective when administered to the human body.

Example 2

Delivery Vehicle

In embodiments, the pharmaceutical composition is delivered in a gelatin capsule delivery vehicle. The gelatin capsule delivery vehicle comprises, for example, gelatin (e.g., Gelatin, NF (150 Bloom, Type B)), hydrolyzed collagen (e.g., GELITA®, GELITA AG, Eberbach, Germany), glycerin, sorbitol special, or other excipients in proportions that are well known and understood by persons of ordinary skill in the art. Sorbitol special may be obtained commercially and may tend to act as a plasticizer and humectant.

A variety of delivery vehicles were developed, as show in Table 2, Gels A through F. In Table 2, each delivery vehicle A through F differs in the proportion of one or more components.

TABLE 2

Gelatin Capsule Delivery Vehicles

| Ingredient | A % w/w | B % w/w | C % w/w | D % w/w | E % w/w | F % w/w |
|---|---|---|---|---|---|---|
| Gelatin, NF (150 Bloom, Type B) | 41.0 | 41.0 | 41.0 | 41.0 | 43.0 | 43.0 |
| Glycerin 99.7%, USP | 6.0 | 6.0 | 6.0 | 6.0 | 18.0 | 18.0 |
| Sorbitol Special, USP | 15.0 | 15.0 | 15.0 | 15.0 | | |
| GELITA ® (hydrolyzed collagen) | 3 | | | | 3.0 | |
| Citric acid | | 0.1 | 0.5 | 1 | | 0.1 |
| Purified Water | 35.0 | 37.9 | 37.5 | 37.0 | 36.0 | 38.9 |
| Total | 100.0 | 100.0 | 100.0 | 100.0 | 100.0 | 100.0 |
| Dissolution gel strips, Avg of 3 (500 ml DH2O, 50 rpm @ 37° C.) | 48 min (42, 45, 58) | 50 min (50, 51, 50) | 75 min (76, 75, 74) | 70 min (70, 71, 70) | | |
| Dissolution gel strips, Avg of 3 (500 ml pH 4 buffer, 50 rpm @ 37° C.) | 70 min | | | | 78 min | 82 min |

Each delivery vehicle A through F was prepared at a temperature range from about 45° C. to about 85° C. Each molten delivery vehicle A through F was cast into a film, dried, and cut into strips. The strips were cut into uniform pieces weighing about 0.5 g, with about 0.5 mm thickness. Strips were placed into a USP Type 2 dissolution vessel in either water or pH 4 buffer solution and the time for them to completely dissolve was recorded (see TABLE 2). Delivery vehicle A had the fastest dissolution in both water and pH 4 buffer solution.

Example 3

Pharmaceutical Compositions and Delivery Vehicle

Various combinations of the pharmaceutical compositions from TABLE 1 and from TABLE 2 were prepared. The combinations are shown in TABLE 3.

TABLE 3

| Trial | Pharmaceutical Composition | Ratio | Batch Size g | Delivery Vehicle |
|---|---|---|---|---|
| 1 | MCM:39/01 | 8:2 | 750 | A |
| 2 | MCM:50/13 | 8:2 | 750 | A |
| 3 | MCM:TEFOSE 63 | 8:2 | 750 | A |
| 4 | MCM:TEFOSE 63 | 8:2 | 750 | B |
| 5 | MIGLYOL 812:TEFOSE 63 | 9:1 | 750 | A |

Each aliquot of the pharmaceutical compositions of Table 3 about 300 mg to about 310 mg. Batch size was as listed in TABLE 3. To encapsulate the vehicle system, each 300 mg to about 310 mg pharmaceutical composition aliquot was encapsulated in about 200 mg of the gelatin capsule delivery vehicle. Thus, for example, in Trial 1, the pharmaceutical composition denoted by MCM: 39/01 was encapsulated in gelatin capsule delivery vehicle A for a total encapsulated weight of about 500 mg to about 510 mg. The aliquot size is arbitrary depending on the concentration of the estradiol and the desired gelatin capsule delivery vehicle size. Artisans will readily understand how to adjust the amount of estradiol in the pharmaceutical composition to accommodate a given size of delivery vehicle, when the delivery vehicle encapsulates the pharmaceutical composition.

Example 4

Estradiol Solubility

In various experiments, solubilizing agents were tested to determine whether they were able to solubilize 2 mg of estradiol for a total pharmaceutical composition weight of 100 mg. The solubilizing agents were considered suitable if estradiol solubility in the solubilizing agent was greater than or equal to about 20 mg/g. Initial solubility was measured by dissolving micronized estradiol into various solubilizing agents until the estradiol was saturated (the estradiol/solubilizing agent equilibrated for three days), filtering the undissolved estradiol, and analyzing the resulting pharmaceutical composition for estradiol concentration by HPLC.

TABLE 4

| Solubility of Solubilizing Agents | |
|---|---|
| Ingredient | Solubility (mg/g) |
| PEG 400 | 105* |
| Propylene Glycol | 75* |

TABLE 4-continued

| Solubility of Solubilizing Agents | |
|---|---|
| Ingredient | Solubility (mg/g) |
| Polysorbate 80 | 36* |
| TRANSCUTOL HP | 141 |
| CAPMUL PG8 | 31.2 |

(*denotes literature reference)

Example 5

Pharmaceutical Compositions

The following pharmaceutical compositions are contemplated.

Gel Mass

| Ingredient | % w/w | Qty/Batch (kg) |
|---|---|---|
| Gelatin 150 Bloom Limed Bone, NF | 41.00 | 82.00 |
| Hydrolyzed Gelatin | 3.00 | 6.00 |
| Glycerin 99.7% | 6.00 | 12.00 |
| Sorbitol Special, NF | 15.00 | 30.00 |
| Opatint White G-18006 | 1.20 | 2.40 |
| Opatine Red DG-15001 | 0.06 | 0.12 |
| Purified Water, USP | 33.74 | 67.48 |
| Total | 100.00 | 200.00 Kg |

Pharmaceutical Composition 1: 10 µg Estradiol

| Ingredients | Qty/Capsule (mg) | % w/w | Qty/Batch |
|---|---|---|---|
| Estradiol hemihydrate micronized, USP | 0.010 | 0.003 | 0.10 g |
| CAPMUL ® MCM, NF (Glyceryl Caprylate/Caprate or Medium Chain Mono- and Diglycerides) | 240.0 | 79.997 | 2.40 kg |
| GELUCIRE ® 50/13 (stearoyl polyoxyl-32 glycerides NF) | 60.0 | 20.0 | 600.0 g |
| Total | 300.0 | 100.0 | 3.0 kg |

Pharmaceutical Composition 2: 10 µg Estradiol

| Ingredients | Qty/Capsule (mg) | % w/w | Qty/Batch |
|---|---|---|---|
| Estradiol hemihydrate micronized, USP | 0.010 | 0.003 | 0.10 g |
| MIGLOYL ® 812 (medium chain triglyceride) | 270.0 | 89.997 | 2.70 kg |
| TEFOSE ® 63 (mixture of PEG-6 stearate or ethylene glycol palmitostearate or PEG-32 stearate; polyoxyl 6 and polyoxyl 32 palmitostearate/glycol stearate) | 30.0 | 10.0 | 300.0 g |
| Total | 300.0 | 100.0 | 3.00 kg |

Pharmaceutical Composition 3: 25 µg Estradiol

| Ingredients | Qty/Capsule (mg) | % w/w | Qty/Batch |
|---|---|---|---|
| Estradiol hemihydrate micronized, USP | 0.026* | 0.009 | 0.26 g |
| MIGLOYL ® 812 (medium chain triglyceride) | 270.0 | 89.991 | 2.70 kg |

-continued

| Ingredients | Qty/Capsule (mg) | % w/w | Qty/Batch |
|---|---|---|---|
| TEFOSE ® 63 (mixture of PEG-6 stearate or ethylene glycol palmitostearate or PEG-32 stearate; polyoxyl 6 and polyoxyl 32 palmitostearate/glycol stearate) | 30.02 | 10.0 | 300.0 g |
| Total | 300.0 | 100.0 | 3.00 kg |

*1.0 mg estradiol is equivalent to 1.03 mg estradiol hemihydrate

Pharmaceutical Composition 4: 4 µg Estradiol

| Ingredients | Qty/Capsule (mg) | % w/w | Qty/Batch |
|---|---|---|---|
| Estradiol hemihydrate micronized, USP | 0.0041* | 0.001 | 0.041 g |
| MIGLOYL ® 812 (medium chain triglyceride) | 269.99 | 89.999 | 2700.0 g |
| TEFOSE ® 63 (mixture of PEG-6 stearate or ethylene glycol palmitostearate or PEG-32 stearate; polyoxyl 6 and polyoxyl 32 palmitostearate/glycol stearate) | 30.0 | 10.0 | 300.0 g |
| Total | 300.0 | 100.0 | 3000.0 g |

*1.0 mg estradiol is equivalent to 1.03 mg estradiol hemihydrate

Example 6

Process

FIG. 1 illustrates an embodiment of a method making pharmaceutical composition comprising estradiol solubilized in CapmulMCM/Gelucire solubilizing agent encapsulated in a soft gelatin delivery vehicle 100. In operation 102, the CapmulMCM is heated to 40° C.±5° C. Heating may be accomplished through any suitable means. The heating may be performed in any suitable vessel, such as a stainless steel vessel. Other pharmaceutical compositions can be made using the same general method by substituting various excipients, including the solubilizing agent.

In operation 104, GELUCIRE is mixed with the CapmulMCM to form the finished solubilizing agent. As used herein, any form of GELUCIRE may be used in operation 104. For example, one or more of GELUCIRE 39/01, GELUCIRE 43/01, GELUCIRE 50/13 may be used in operation 104. Mixing is performed as would be known to persons of ordinary skill in the art, for example by impeller, agitator, stirrer, or other like devices used to mix pharmaceutical compositions. Operation 104 may be performed under an inert or relatively inert gas atmosphere, such as nitrogen gas. Mixing may be performed in any vessels that are known to persons of ordinary skill in the art, such as a stainless steel vessel or a steel tank.

In operation 106 estradiol is mixed into the solubilizing agent. In embodiments, the estradiol in micronized when mixed into the solubilizing agent. In other embodiments, the estradiol added is in a non-micronized form. Mixing may be facilitated by an impeller, agitator, stirrer, or other like devices used to mix pharmaceutical compositions. Operation 106 may be performed under an inert or relatively inert gas atmosphere, such as nitrogen gas.

In embodiments, however, the addition of estradiol may be performed prior to operation 104. In that regard, operations 104 and 106 are interchangeable with respect to timing or can be performed contemporaneously with each other.

In operation 110, the gelatin delivery vehicle is prepared. Any of the gelatin delivery vehicles described herein may be used in operation no. In embodiments, gelatin, hydrolyzed collagen, glyercin, and other excipients are combined at a temperature range from about 45° C. to about 85° C. and prepared as a film. Mixing may occur in a steel tank or other container used for preparing gelatin delivery vehicles. Mixing may be facilitated by an impellor, agitator, stirrer, or other devices used to combine the contents of gelatin delivery vehicles. Operation 110 may be performed under an inert or relatively inert gas atmosphere, such as nitrogen gas. In embodiments, the gelatin delivery vehicle mixture is degassed prior to being used to encapsulate the pharmaceutical composition.

In operation 112, the gelatin delivery vehicle encapsulates the pharmaceutical composition, according to protocols well known to persons of ordinary skill in the art. In operation 112, a soft gelatin capsule delivery vehicle is prepared by combining the pharmaceutical composition made in operation 106 with the gelatin delivery vehicle made in operation no. The gelatin may be wrapped around the material, partially or fully encapsulating it or the gelatin can also be injected or otherwise filled with the pharmaceutical composition made in operation 106.

In embodiments, operation 112 is completed in a suitable die to provide a desired shape. Vaginal soft gel capsules may be prepared in a variety of geometries. For example, vaginal soft gel capsules may be shaped as a tear drop, a cone with frustoconical end, a cylinder, a cylinder with larger "cap" portion as illustrated in FIG. 2, or other shapes suitable for insertion into the vagina. The resulting pharmaceutical composition encapsulated in the soft gelatin delivery vehicle may be inserted digitally or with an applicator.

Example 7

Study of Estradiol Pharmaceutical Composition on the Improvement of Vulvovaginal Atrophy (VVA)

The objective of this study was designed to evaluate the efficacy and safety of a pharmaceutical composition comprising 10 µg estradiol (i.e., Pharmaceutical Composition 2) in treating moderate to severe symptoms of VVA associated with menopause after 14 days of treatment, and to estimate the effect size and variability of vulvovaginal atrophy endpoints. In addition, the systemic exposure to estradiol from single and multiple doses of the pharmaceutical composition was investigated.

This study was a phase 1, randomized, double-blind, placebo-controlled trial to evaluate safety and efficacy of the pharmaceutical composition in reducing moderate to severe symptoms of vaginal atrophy associated with menopause and to investigate the systemic exposure to estradiol following once daily intravaginal administrations of a pharmaceutical composition for 14 days.

Postmenopausal subjects who met the study entry criteria were randomized to one of two treatment groups (pharmaceutical composition or placebo). During the screening period subjects were asked to self-assess the symptoms of VVA, including vaginal dryness, vaginal or vulvar irritation or itching, dysuria, vaginal pain associated with sexual activity, and vaginal bleeding associated with sexual activity. Subjects with at least one self-assessed moderate to severe symptom of VVA identified by the subject as being most bothersome to her were eligible to participate in the study.

Clinical evaluations were performed at the following time points:
Screening Period (up to 28 days);
Visit 1—Randomization/Baseline (day 1);
Visit 2—Interim (day 8); and
Visit 3—End of the treatment (day 15).

Eligible subjects were randomized in a 1:1 ratio to receive either pharmaceutical composition comprising estradiol 10 µg or a matching placebo vaginal softgel capsule, and self-administered their first dose of study medication at the clinical facility under the supervision of the study personnel. Serial blood samples for monitoring of estradiol level were collected at 0.0, 1.0, 3.0, and 6.0 hours relative to first dose administration on day 1. Subjects remained at the clinical site until completion of the 6-hour blood draw and returned to clinical facility for additional single blood draws for measurement of estradiol concentration on day 8 (before the morning dose) and day 15. Subjects were provided with enough study medication until the next scheduled visit and were instructed to self-administer their assigned study treatment once a day intravaginally at approximately the same time (±1 hour) every morning. Each subject was provided with a diary in which she was required to daily record investigational drug dosing dates and times. Subjects returned to clinical facility on day 8 for interim visit and on day 15 for end of treatment assessments and post study examinations. Capsule disintegration state was assessed by the investigator at day 1 (6 hours post-dose) and day 15.

The study involved a screening period of up to 28 days before randomization and treatment period of 14 days. Selection of dosage strength (estradiol 10 µg) and treatment regimen (once daily for two weeks) was based on the FDA findings on safety and efficacy of the RLD.

Number of Subjects (Planned and Analyzed)

Up to 50 (25 per treatment group) postmenopausal female subjects 40 to 75 years old with symptoms of moderate to severe VVA were randomized. 50 subjects were enrolled, 48 subjects completed the study, and 48 subjects were analyzed.

Diagnosis and Main Criteria for Inclusion

Fifty female subjects were enrolled in the study. Postmenopausal female subjects 40 to 75 years of age, with a mean age was 62.3 years were enrolled. Subjects' mean weight (kg) was 71.2 kg with a range of 44.5-100 kg. Subjects' mean height (cm) was 162.6 cm with a range of 149.9-175.2 cm, and the mean BMI (kg/m$^2$) was 26.8 kg/m$^2$ with a range of 19-33 kg/m$^2$. Criteria of inclusion in the study included: self-identification of at least one moderate to severe symptom of VVA, for example, vaginal dryness, dysparuenia, vaginal or vulvar irritation, burning, or itching, dysuria, vaginal bleeding associated with sexual activity, that was identified by the subject as being most bothersome to her; ≤5% superficial cells on vaginal smear cytology; vaginal pH>5.0; and estradiol level ≤50 pg/ml. Subject who were judged as being in otherwise generally good health on the basis of a pre-study physical examination, clinical laboratory tests, pelvic examination, and mammography were enrolled.

Estradiol 10 µg or Placebo, Dose, and Mode of Administration

Subjects were randomly assigned (in 1:1 allocation) to self-administer one of the following treatments intravaginally once daily for 14 days:
Treatment A: The pharmaceutical composition of Example 5 (Pharmaceutical Composition 2: 10 µg estradiol); or
Treatment B: Placebo vaginal softgel capsule, containing the same formulation as Treatment A, except for the 10 µg of estradiol.

The estradiol formulation was a tear drop shaped light pink soft gel capsule. Treatment B had the same composition, appearance, and route of administration as the Treatment A, but contained no estradiol.

Duration of Treatment

The study involved a screening period of up to 28 days before randomization and a treatment period of 14 days.

Criteria for Evaluation

Efficacy Endpoints:

Change from baseline (screening) to day 15 in the Maturation Index (percent of parabasal vaginal cells, superficial vaginal cells, and intermediate vaginal cells) of the vaginal smear. Data for this endpoint are shown in Tables 6-8.

Change from baseline (screening) to day 15 in vaginal pH. Data for this endpoint are shown in Table 9.

Change from baseline (randomization) to day 15 in severity of the most bothersome symptoms: (1) vaginal dryness; (2) vaginal or vulvar irritation, burning, or itching; (3) dysuria; (4) dysparuenia; (5) vaginal bleeding associated with sexual activity. Data for this endpoint are shown in Tables 13 and 15.

Change from baseline (randomization) to day 15 in investigator's assessment of the vaginal mucosa. Data for this endpoint are shown in Tables 18-21.

Unless otherwise noted, the efficacy endpoints were measured as a change-from Visit 1—Randomization/Baseline (day 1) to Visit 3—End of the treatment (day 15), except for vaginal bleeding which was expressed as either treatment success or failure.

Other endpoints include:
Vital signs, weight, changes in physical exam, pelvic and breast exam, and adverse events were evaluated as part of the safety endpoints.
Concentration of estradiol at each sampling time.
Peak concentration of estradiol on day 1 and sampling time at which peak occurred.
Delivery vehicle disintegration to measure the amount of residual delivery vehicle remains in the vagina post treatment.

Results from the assessment of plasma concentrations of estradiol are presented in Table 5.

TABLE 5

Safety Results: The descriptive statistics for Day 1 plasma estradiol $C_{max}$ and $T_{max}$ are provided below.

| | Estradiol 10 µg | | Placebo | |
|---|---|---|---|---|
| | $C_{max}$ | $T_{max}$ | $C_{max}$ | $T_{max}$ |
| N | 24 | 24 | 26 | 26 |
| Mean ± SD | 30.7 ± 7.47 | 2.12 ± 1.73 | 27.5 ± 17.26 | 4.00 ± 2.68 |
| Geometric Mean | 29.9 | — | 24.7 | — |
| Median | 29.8 | 1.00 | 22.1 | 6.00 |
| Min, Max | 19.7, 52.3 | 1.00, 6.00 | 15.1, 90.0 | 0.00, 6.00 |
| CV % | 24.3% | 81.3% | 62.9% | 67.1% |

Other Endpoints:
Maturation Index Results

Vaginal cytology data was collected as vaginal smears from the lateral vaginal walls according to standard procedures to evaluate vaginal cytology at screening and Visit 3—End of treatment (day 15). The change in the Maturation Index was assessed as a change in cell composition measured at Visit 1—Baseline (day 1) compared to the cell composition measured at Visit 3—End of treatment (day 15). The change in percentage of superficial, parabasal, and intermediate cells obtained from the vaginal mucosal epithelium from a vaginal smear was recorded. Results from these assessments are presented in Tables 6, 7, and 8.

TABLE 6

Primary Efficacy Analysis Results of Change from Baseline (Screening) to Day 15 in the Maturation Index of the Vaginal Smear
(Percent Parabasal Cells)

| Population | Statistics | Estradiol 10 μg | Placebo | Difference Between Treatment Means | 90% CI for Difference | Estradiol 10 μg vs. Placebo P-value |
|---|---|---|---|---|---|---|
| Intent-to-Treat | N | 24 | 24 | — | — | — |
| | Least-Squares Mean | −54.4 | −4.80 | −49.6 | (−60.4, −38.8) | <0.0001 |
| | Mean ± SD | −53.8 ± 39.7 | −5.4 ± 22.3 | — | — | — |
| | Median | −60.0 | −5.0 | — | — | — |
| | Min, Max | −100.0 0.0 | −60.0, 60.0 | — | — | — |

[1] Confidence interval for the estradiol 10 μg-Placebo from ANCOVA with treatment as a fixed effect and baseline as a covariate.
[2] P-value for treatment comparison from ANCOVA with treatment as a fixed effect and baseline as a covariate.

TABLE 7

Primary Efficacy Analysis Results of Change from Baseline (Screening) to Day 15 in the Maturation Index of the Vaginal Smear
(Superficial Cells)

| Population | Statistics | Estradiol 10 μg | Placebo | Difference Between Treatment Means | 90% CI for Difference | Estradiol 10 μg vs. Placebo P-value |
|---|---|---|---|---|---|---|
| Intent-to-Treat | N | 24 | 24 | — | — | — |
| | Least-Squares Mean | 35.2 | 8.75 | 26.5 | (15.4, 37.6) | 0.0002 |
| | Mean ± SD | 35.2 ± 26.4 | 8.8 ± 18.7 | — | — | — |
| | Median | 40.0 | 0.0 | — | — | — |
| | Min, Max | 0.0, 80.0 | 0.0, 90.0 | — | — | — |

[1] Confidence interval for the estradiol 10 μg-Placebo from ANOVA with treatment as a fixed effect.
[2] P-value for treatment comparison from ANOVA with treatment as a fixed effect.

TABLE 8

Primary Efficacy Analysis Results of Change from Baseline (Screening) to Day 15 in the Maturation Index of the Vaginal Smear
(Intermediate Cells)

| Population | Statistics | Estradiol 10 μg | Placebo | Difference Between Treatment Means | 90% CI for Difference | Estradiol 10 μg vs. Placebo P-value[2] |
|---|---|---|---|---|---|---|
| Intent-to-Treat | N | 24 | 24 | — | — | — |
| | Least-Squares Mean | 18.7 | −3.54 | 22.3 | (11.1, 33.5) | 0.0017 |
| | Mean ± SD | 18.5 ± 42.7 | −3.3 ± 21.6 | — | — | — |
| | Median | 22.5 | −5.0 | — | — | — |
| | Min, Max | −60.0, 100.0 | −60.0, 20.0 | — | — | — |

[1] Confidence interval for the estradiol 10 μg-Placebo from ANCOVA with treatment as a fixed effect and baseline as a covariate.
[2] P-value for treatment comparison from ANCOVA with treatment as a fixed effect and baseline as a covariate.

Change in pH Results

Vaginal pH was measured at Screening and Visit 3—End of treatment (day 15). The pH measurement was obtained by pressing a pH indicator strip against the vaginal wall. The subjects entering the study were required to have a vaginal pH value greater than 5.0 at screening. pH values were recorded on the subject's case report form. The subjects were advised not to have sexual activity and to refrain from using vaginal douching within 24 hours prior to the measurement. Results from these assessments are presented in Table 9.

TABLE 9

Primary Efficacy Analysis Results of Change from Baseline (Screening) to Day 15 in Vaginal pH

| Population | Statistics | Estradiol 10 μg | Placebo | Difference Between Treatment Means | 90% CI for Difference[1] | Estradiol 10 μg vs. Placebo P-value[2] |
|---|---|---|---|---|---|---|
| Intent-to-Treat | N | 24 | 24 | — | — | — |
| | Least-Squares Mean | −0.974 | −0.339 | −0.635 | (−0.900, −0.368) | 0.0002 |
| | Mean ± SD | −0.917 ± 0.686 | −0.396 ± 0.659 | — | — | — |
| | Median | −1.00 | −0.500 | — | — | — |
| | Min, Max | −2.00, 0.500 | −1.50, 0.500 | — | — | — |

[1]Confidence interval for the estradiol 10 μg-Placebo from ANCOVA with treatment as a fixed effect and baseline as a covariate.
[2]P-value for treatment comparison from ANCOVA with treatment as a fixed effect and baseline as a covariate.

Most Bothersome Symptoms Data

Subjects were asked to specify the symptom that she identified as the "most bothersome symptom." During the screening period all of the subjects were provided with a questionnaire to self-assess the symptoms of VVA: (1) vaginal dryness; (2) vaginal or vulvar irritation, burning, or itching; (3) dysuria; (4) dysparuenia; (5) vaginal bleeding associated with sexual activity. Each symptom, with the exception of vaginal bleeding associated with sexual activity, was measured on a scale of 0 to 3, where 0=none, 1=mild, 2=moderate, and 3=severe. Vaginal bleeding associated with sexual activity was measured in a binary scale: N=no bleeding; Y=bleeding. The subject's responses were recorded. All randomized subjects were also provided a questionnaire to self-assess the symptoms of VVA at Visit 1—Randomization/Baseline (day 1) and at Visit 3—End of the treatment (day 15). Subjects recorded their self-assessments daily in a diary and answers were collected on days 8 and 15 (end of treatment). Pre-dose evaluation results obtained at Visit 1 were considered as baseline data for the statistical analyses. Data from these assessments are presented in Tables 10 and 11.

TABLE 10

Baseline Characteristics for Vaginal Atrophy Symptoms (ITT Population)

| VVA Symptom | Statistics | Estradiol 10 μg | Placebo | Estradiol 10 μg vs. Placebo P-value[1] |
|---|---|---|---|---|
| Vaginal dryness | N of Subjects | 24 | 24 | — |
| | Mean | 2.292 | 2.375 | 0.68231 |
| Vaginal or vulvar irritation/burning/itching | N of Subjects | 24 | 24 | — |
| | Mean | 0.875 | 1.333 | 0.08721 |
| Pain, burning or stinging when urinating | N of Subjects | 24 | 24 | — |
| | Mean | 0.583 | 0.625 | 0.87681 |
| Vaginal pain associated with sexual activity | N of Subjects[2] | 12 | 12 | — |
| | Mean | 2.083 | 2.333 | 0.54281 |
| Vaginal bleeding associated with sexual activity | N of Subjects[2] | 12 | 12 | — |
| | Percent[3] | 25.00 | 33.33 | 0.31463 |

[1]P-value for treatment comparison from ANOVA/ANCOVA with treatment as a fixed effect and Baseline as a covariate when appropriate.
[2]N = number of subjects sexually active at baseline.
[3]Percent of subjects with bleeding, evaluated using Fisher's Exact Test.

TABLE 11

Additional Efficacy Analysis Results of Change from Baseline (Randomization) to Day 15 in Severity of Vaginal Atrophy Symptoms

| Symptom | Statistical Method[1] | Least-Squares Mean Estradiol 10 μg | Placebo | Difference Between Treatment Means | 90% CI for Difference[2] | Estradiol 10 μg vs. Placebo P-value |
|---|---|---|---|---|---|---|
| Vaginal dryness | ANCOVA | 0.980 | 0.729 | 0.251 | (−0.706, 0.204) | 0.3597 |
| Vaginal or vulvar Irritation/buring/itching | ANCOVA | 0.694 | 0.514 | 0.180 | (−0.549, 0.189) | 0.4159 |
| Pain/Burning/Stinging (Urination) | ANCOVA | 0.391 | 0.359 | 0.032 | (−0.263, 0.200) | 0.8185 |
| Vaginal pain associated with sexual activity | ANOVA | 0.800 | 0.500 | 0.300 | (−1.033, 0.433) | 0.4872 |

[1]ANOVA model contained a fixed effect for treatment. ANCOVA added baseline as a covariate to the model.
[2]Confidence interval for the difference between estradiol 10 μg and Placebo treatment least-squares means.

Changes to the most bothersome symptom from the baseline was scored according to the evaluation of VVA symptoms generally set forth above. Tables 13 and 14 show a comparison between the pharmaceutical composition 1 and placebo generally for most bothersome symptom and vaginal atrophy symptom. It is noteworthy to point out that these measurement demonstrated a trend of improvement, though not statistically significant, at day 15.

TABLE 13

Primary Efficacy Analysis Results of Change from Baseline (Randomization) to Day 15 in Severity of the Most Bothersome VVA

| Population | Statistics | Estradiol 10 μg | Placebo | Difference Between Treatment Means | 90% CI for Difference[1] | Estradiol 10 μg vs. Placebo P-value[2] |
|---|---|---|---|---|---|---|
| Intent-to-Treat | N | 24 | 24 | — | — | — |
| | Least-Squares Mean | −1.043 | −1.042 | −0.002 | (−0.497, 0.493) | 0.9951 |
| | Mean ± SD | −1.043 ± 0.928 | −1.042 ± 1.08 | — | — | — |
| | Median | −1.00 | −1.00 | — | — | — |
| | Min, Max | −3.00, 0.00 | −3.00, 0.00 | — | — | — |

[1]Confidence interval for the estradiol 10 μg-Placebo from ANOVA with treatment as a fixed effect.
[2]P-value for treatment comparison from ANOVA with treatment as a fixed effect.

TABLE 14

Additional Efficacy Analysis Results of Change from Baseline (Randomization) to Day 15 in Severity of Vaginal Atrophy Symptoms Symptom

| Symptom | Statistical Method[1] | Least-Squares Mean TX-12-004-HR | Placebo | Difference Between Treatment Means | 90% CI for Difference[2] | TX-12-004-HR vs. Placebo P-value |
|---|---|---|---|---|---|---|
| Dryness | ANCOVA | −0.980 | −0.729 | −0.251 | (−0.706, 0.204) | 0.3597 |
| Irritation | ANCOVA | −0.694 | −0.514 | −0.180 | (−0.549, 0.189) | 0.4159 |
| Pain (Sex) | ANOVA | −0.800 | −0.500 | −0.300 | (−1.033, 0.433) | 0.4872 |
| Pain/Burning/Stinging (Urination) | ANCOVA | −0.391 | −0.359 | −0.032 | (−0.263, 0.200) | 0.8185 |

[1]ANOVA model contained a fixed effect for treatment. ANCOVA added baseline as a covariate to the model.
[2]Confidence interval for the difference between TX-12-004-HR and Placebo treatment least-squares means.

With respect to the most bothersome symptoms data presented in Tables 13 and 14, the period over which the data was measured is generally considered insufficient to make meaningful conclusions. However, the trends observed as part of this study suggest that the data will show improvement of the most bothersome symptoms when data for a longer time period is collected.

The absence or presence of any vaginal bleeding associated with sexual activity was also measured as one of the most bothersome symptoms. The data for vaginal bleeding associated with sexual activity is reported in Table 15.

TABLE 15

Primary Efficacy Analysis Results of Change from Baseline (Randomization) to Day 15 in Vaginal Bleeding Associated with Sexual Activity

| | | Baseline (Randomization) and Day 15 Summary of Vaginal Bleeding | | | |
|---|---|---|---|---|---|
| Treatment | N* | Bleeding/ No Bleeding (Success)[2] | Bleeding/ Bleeding (Failure) | No Bleeding/ Bleeding (Failure) | No Bleeding/ No Bleeding (NC) |
| Estradiol 10 µg | 10 | 2 (100%) | 0 | 0 | 8 |
| Placebo | 10 | 1 (20%) | 3 | 1 | 5 |
| P-Value for Estradiol 10 µg vs. Placebo[1] | | 0.1429 | — | — | — |

*N = Total number of patients within each treatment group who were sexually active at both Baseline and Day 15 and provided a response at both visits.
NC = No Change - not considered in the statistical comparison.
[1]P-value for treatment comparison from Fisher's Exact Test.
[2]Percent is based on the number of subjects classified as either a Success or a Failure (N = 2 for estradiol 10 µg; N = 5 for Placebo Estradiol Level/Pharmacokinetics Data In this study, the systemic exposure to estradiol following once daily intravaginal administration of estradiol 10 µg for 14 days was investigated. Descriptive statistics of the plasma estradiol concentrations taken at each sampling time and the observed $C_{max}$ and $T_{max}$ values were recorded in Tables 16 and 17. No statistically significant difference in the systemic concentration of estradiol 10 µg versus the placebo group was observed, which suggests the estradiol is not carried into the blood stream where it will have a systemic effect. Rather, it remains in localized tissues; the effect of estradiol is therefore believed be local to the location of administration (i.e., the vagina). The lower limits of detection of the assays used to measure the pharmacokinetic data may have affected the measured the accuracy of the pk values presented. Additional pk studies were performed with more accurate assays in Examples 8 and 9.

For the purpose of monitoring the estradiol level during the study blood samples were collected at 0.0, 1.0, 3.0, and 6.0 hours relative to dosing on day 1; prior to dosing on day 8; and prior to dosing on day 15. Efforts were made to collect blood samples at their scheduled times. Sample collection and handling procedures for measurement of estradiol blood level was performed according to procedure approved by the sponsor and principal investigator. All baseline and post-treatment plasma estradiol concentrations were determined using a validated bioanalytical (UPLC-MS/MS) methods. These data are shown in Tables 16 and 17.

TABLE 16

Descriptive Statistics of Estradiol Concentrations (pg/ml) at Each Sampling Time

| | Sampling Time | | | | | |
|---|---|---|---|---|---|---|
| Treatment | 0 Hour | 1 Hour | 3 Hours | 6 Hours | Pre-dose Day 8 | Pre-dose Day 15 |
| Estradiol 10 µg | | | | | | |
| N | 24 | 24 | 24 | 24 | 24 | 22 |
| Mean ± SD | 20.1 ± 5.74 | 28.7 ± 5.89 | 25.7 ± 5.71 | 23.4 ± 7.91 | 21.4 ± 9.28 | 23.4 ± 8.72 |
| Median | 20.2 | 28.9 | 24.7 | 22.3 | 20.7 | 20.7 |
| Min, Max | 2.63, 38.3 | 18.8, 43.9 | 19.3, 47.5 | 3.31, 52.3 | 2.09, 52.2 | 17.9, 54.7 |
| Placebo | | | | | | |
| N | 26 | 26 | 26 | 26 | 25 | 24 |
| Mean ± SD | 20.5 ± 4.29 | 21.0 ± 6.14 | 19.0 ± 5.92 | 26.9 ± 17.36 | 29.9 ± 22.51 | 28.1 ± 16.80 |
| Median | 20.8 | 20.8 | 20.9 | 21.7 | 21.6 | 21.1 |
| Min, Max | 4.03, 29.1 | 3.19, 41.2 | 3.15, 26.9 | 15.1, 90.0 | 15.0, 116.2 | 14.7, 81.3 |

TABLE 17

Descriptive Statistics of Estradiol $C_{max}$ and $T_{max}$ on Day 1

|  | Estradiol 10 µg | | Placebo | |
| --- | --- | --- | --- | --- |
|  | $C_{max}$ | $T_{max}$ | $C_{max}$ | $T_{max}$ |
| N | 24 | 24 | 26 | 26 |
| Mean ± SD | 30.7 ± 7.47 | 2.12 ± 1.73 | 27.5 ± 17.26 | 4.00 ± 2.68 |
| Geometric Mean | 29.9 | — | 24.7 | — |
| Median | 29.8 | 1.00 | 22.1 | 6.00 |
| Min, Max | 19.7, 52.3 | 1.00, 6.00 | 15.1, 90.0 | 0.00, 6.00 |
| CV % | 24.3% | 81.3% | 62.9% | 67.1% |

Assessment of Vaginal Mucosa Data

The investigators rated the vaginal mucosal appearance at day 1 (pre-dose) and day 15. Vaginal color, vaginal epithelial integrity, vaginal epithelial surface thickness, and vaginal secretions were evaluated according to the following degrees of severity: none, mild, moderate, or severe using scales 0 to 3, where 0=none, 1=mild, 2=moderate, and 3=severe. Results from these investigators rated assessments are presented in Tables 18, 19, 20, and 21.

TABLE 18

Primary Efficacy Analysis Results of Change from Baseline (Randomization) to Day 15 in Investigator's Assessment of the Vaginal Mucosa (Assessment of Vaginal Color)

| Population | Statistics | Estradiol 10 µg | Placebo | Difference Between Treatment Means | 90% CI for Difference[1] | Estradiol 10 µg vs. Placebo P-value[2] |
| --- | --- | --- | --- | --- | --- | --- |
| Intent-to-Treat | N | 24 | 24 | — | — | — |
|  | Least-squares Mean | −0.199 | −0.009 | −0.191 | (−0.434, 0.052) | 0.1945 |
|  | Mean ± SD | −0.333 ± 0.565 | 0.125 ± 0.741 |  |  |  |
|  | Median | 0.00 | 0.00 | — | — | — |
|  | Min, Max | −2.00, 0.00 | −1.00, 2.00 | — | — | — |

[1]Confidence interval for the estradiol 10 µg-Placebo from ANCOVA with treatment as a fixed effect and baseline as a covariate.
[2]P-value for treatment comparison from ANCOVA with treatment as a fixed effect and baseline as a covariate.

TABLE 19

Primary Efficacy Analysis Results of Change from Baseline (Randomization) to Day 15 in Investigator's Assessment of the Vaginal Mucosa (Assessment of Vaginal Epithelial Integrity)

| Population | Statistics | Estradiol 10 µg | Placebo | Difference Between Treatment Means | 90% CI for Difference[1] | Estradiol 10 µg vs. Placebo P-value[2] |
| --- | --- | --- | --- | --- | --- | --- |
| Intent-to-Treat | N | 24 | 24 | — | — | — |
|  | Least-squares Mean | −0.342 | 0.176 | −0.518 | (−0.726, −0.311) | 0.0001 |
|  | Mean ± SD | −0.417 ± 0.584 | 0.250 ± 0.442 |  |  |  |
|  | Median | 0.00 | 0.00 | — | — | — |
|  | Min, Max | −1.00, 1.00 | 0.00, 1.00 | — | — | — |

[1]Confidence interval for the estradiol 10 µg-Placebo from ANCOVA with treatment as a fixed effect and baseline as a covariate.
[2]P-value for treatment comparison from ANCOVA with treatment as a fixed effect and baseline as a covariate.

TABLE 20

Primary Efficacy Analysis Results of Change from Baseline (Randomization) to Day 15 in Investigator's Assessment of the Vaginal Mucosa (Assessment of Vaginal Epithelial Surface Thickness)

| Population | Statistics | Estradiol 10 µg | Placebo | Difference Between Treatment Means | 90% CI for Difference[1] | Estradiol 10 µg vs. Placebo P-value[2] |
| --- | --- | --- | --- | --- | --- | --- |
| Intent-to-Treat | N | 24 | 24 | — | — | — |

TABLE 20-continued

Primary Efficacy Analysis Results of Change from Baseline (Randomization) to Day 15 in Investigator's Assessment of the Vaginal Mucosa (Assessment of Vaginal Epithelial Surface Thickness)

| Population | Statistics | Estradiol 10 μg | Placebo | Difference Between Treatment Means | 90% CI for Difference[1] | Estradiol 10 μg vs. Placebo P-value[2] |
|---|---|---|---|---|---|---|
| | Least-squares Mean | −0.034 | −0.133 | 0.099 | (−0.024, 0.221) | 0.1820 |
| | Mean ± SD | −0.125 ± 0.338 | −0.042 ± 0.550 | — | — | — |
| | Median | 0.00 | 0.00 | — | — | — |
| | Min, Max | −1.00, 0.00 | −1.00, 1.00 | — | — | — |

[1] Confidence interval for the estradiol 10 μg-Placebo from ANCOVA with treatment as a fixed effect and baseline as a covariate.
[2] P-value for treatment comparison from ANCOVA with treatment as a fixed effect and baseline as a covariate.

TABLE 21

Primary Efficacy Analysis Results of Change from Baseline (Randomization) to Day 15 in Investigator's Assessment of the Vaginal Mucosa (Assessment of Vaginal Secretions)

| Population | Statistics | Estradiol 10 μg | Placebo | Difference Between Treatment Means | 90% CI for Difference[1] | Estradiol 10 μg vs. Placebo P-value[2] |
|---|---|---|---|---|---|---|
| Intent-to-Treat | N | 24 | 24 | — | — | — |
| | Least-squares Mean | −0.643 | −0.274 | −0.369 | (−0.661, −0.076) | 0.0401 |
| | Mean ± SD | −0.792 ± 0.779 | −0.125 ± 0.741 | — | — | — |
| | Median | −1.00 | 0.00 | — | — | — |
| | Min, Max | −2.00, 1.00 | −2.00, 2.00 | — | — | — |

[1] Confidence interval for the estradiol 10 μg-Placebo from ANCOVA with treatment as a fixed effect and baseline as a covariate.
[2] P-value for treatment comparison from ANCOVA with treatment as a fixed effect and baseline as a covariate.

Delivery Vehicle Disintegration Data

Assessment of capsule disintegration in the vagina (presence or absence) at Day 1 (6 hours after dosing) and Day 15. Results of this assessment is presented in Table 22.

TABLE 22

Capsule Disintegration State in the Vagina on Day 1 and Day 15

| | Estradiol 10 μg | | Placebo | |
|---|---|---|---|---|
| | Day 1 | Day 15 | Day 1 | Day 15 |
| No evidence of capsule present | 23 (95.8%) | 24 (100.0%) | 26 (100.0%) | 24 (92.3%) |
| Evidence of capsule present | 0 (0.0%) | 0 (0.0%) | 0 (0.0%) | 0 (0.0%) |
| Assessment not done | 1 (4.2%) | 0 (0.0%) | 0 (0.0%) | 22 (7.7%) |

Serum hormone level data was collected to measure the serum concentrations of estradiol. These data were used for screening inclusion and were determined using standard clinical chemistry methods.

Appropriateness of Measurements

The selection of the efficacy measurements used in this study was based on FDA's recommendations for studies of estrogen and estrogen/progestin drug products for the treatment of moderate to severe vasomotor symptoms associated with the menopause and moderate to severe symptoms of vulvar and vaginal atrophy associated with the menopause (*Food and Drug Administration, Guidance for Industry, Estrogen and Estrogen/Progestin Drug Products to Treat Vasomotor Symptoms and Vulvar and Vaginal Atrophy Symptoms—Recommendations for Clinical Evaluation*. January 2003, hereby incorporated by reference).

Standard clinical, laboratory, and statistical procedures were utilized in the trial. All clinical laboratory procedures were generally accepted and met quality standards.

Statistical Methods:

Efficacy:

Analysis of variance (ANOVA) was used to evaluate the change from baseline differences between the subjects receiving estradiol 10 μg and placebo capsules for all efficacy endpoints, except for vaginal bleeding, to estimate the effect size and variability of the effect. In some cases, for example, for some vaginal atrophy symptoms, the change from baseline (post dose response) was correlated with the baseline value (p<0.05), so baseline was included as a covariate to adjust for this correlation (Analysis of Covariance, ANCOVA). The 90% confidence intervals on the differences between estradiol 10 µg and placebo endpoint means were determined to evaluate the effect size. The change from baseline in vaginal bleeding associated with sexual activity was evaluated in terms of the proportion of subjects who had treatment success or failure. Any subject reporting bleeding at baseline who did not report bleeding at Day 15 was considered to have been successfully treated. Any subject reporting bleeding at day 15 was considered a treatment failure, regardless of whether they reported baseline bleeding or not. Subjects reporting no bleeding at both baseline and day 15 were classified as no-change and were excluded from the statistical evaluation. The difference in the proportion of subjects with success between the two treatment groups was statistically evaluated using Fisher's Exact Test. Results of this difference in proportion are presented in Table 10.

Measurements of Treatment Compliance

Subjects were required to complete a diary in order to record treatment compliance. Diaries were reviewed for treatment compliance at day 8 and day 15 visits. A total of 45 subjects (21 subjects in the estradiol 10 µg group and 24 subjects in the placebo group) were 100% compliant with the treatment regimen.

Due to the investigative nature of the study, no adjustments were made for multiplicity of endpoints.

Safety:

The frequency and severity of all adverse events were summarized descriptively by treatment group.

Results: All forty eight (48) subjects who completed the study were included in the primary efficacy analyses. The results of efficacy analyses are presented throughout Tables 5, 6, and 7.

Conclusions

Efficacy

The two-week treatment with pharmaceutical composition 10 µg led to a statistically significant greater mean decrease in percent of parabasal cells than did placebo treatment (54% vs. 5%, p<0.0001), as illustrated in Table 6. At the same time, a significantly greater mean increase in the percent of superficial cells was observed with the pharmaceutical composition (35%) than with the placebo capsules (9%), with the difference being highly statistically significant (p=0.0002), as illustrated in Table 7. The difference in pH reduction between the pharmaceutical composition (0.97 units) compared to that for the placebo (0.34 units) was only slightly greater than 0.5 units, but the difference was detected as statistically significant (p=0.0002), as illustrated in Table 9.

While the decrease in severity of the most bothersome symptom was essentially the same (~1 unit) for both pharmaceutical composition and placebo, the reductions in the severity of the individual symptoms of vaginal dryness, irritation and pain during sexual activity were all marginally better for the active treatment than for the placebo treatment. None of the differences between the two treatments, all of which were ≤0.3 units, were detected as statistically significant. There was no difference between the two treatments in regard to reduction of pain/burning/stinging during urination (~0.4 unit reduction). The length of the study was not long enough to show a separation between the most bothersome symptoms in the pharmaceutical composition and placebo. However, the trends of most bothersome symptoms suggest that with a suitable period of time, significantly significant differences between the two treatments would be observed.

The two-week treatment with estradiol 10 µg capsules showed no statistically detectable difference in regard to reduction of severity from baseline according to the investigator's assessment of vaginal color or vaginal epithelial surface thickness. Pharmaceutical composition capsules did demonstrate a statistically significant greater reduction than did placebo in severity of atrophic effects on vaginal epithelial integrity (−0.34 vs. 0.18, p=0.0001) and vaginal secretions (−0.64 vs. −0.27, p=0.0401).

Descriptive statistical analyses (mean, median, geometric mean, standard deviation, CV, minimum and maximum, $C_{max}$, and $T_{max}$) were conducted on the estradiol concentrations at each sampling time, the peak concentration on day 1 and the time of peak concentration. Results from this assessment are presented in Tables 16 and 17.

A pharmaceutical composition comprising estradiol 10 µg outperformed placebo treatment in regard to improvement in the Maturation Index, reduction in vaginal pH, reduction in the atrophic effects on epithelial integrity and vaginal secretions. The lack of statistical significance between the two treatments in regard to reduction of severity for the most bothersome symptom, and the individual vaginal atrophy symptoms of dryness, irritation, pain associated with sexual activity, and pain/burning/stinging during urination, is not unexpected given the small number of subjects in the study and the short duration of therapy. Too few subjects in the study had vaginal bleeding associated with sexual activity to permit any meaningful evaluation of this vaginal atrophy symptom.

Of the 48 subjects enrolled in the study, 45 subjects were 100% compliant with the treatment regimen. Of the remaining three subjects, one removed herself from the study due to personal reasons and the other two subjects each missed one dose due to an adverse event.

Safety

Although the Day 1 mean plasma estradiol peak concentration for the pharmaceutical composition was somewhat higher than that for the Placebo (ratio of geometric means=1.21:Test Product (estradiol 10 µg) 21%>Placebo), no statistically significant difference was determined. However, the assay methods were questionable, resulting in questionable pk data. Additional pk studies were performed in Examples 8 and 9.

There were no serious adverse events in the study.

Overall, the pharmaceutical composition comprising estradiol 10 µg was well tolerated when administered intravaginally in once daily regimen for 14 days.

Example 8 pk Study (25 µg Formulation)

A pk study was undertaken to compare the 25 µg formulation disclosed herein (Pharmaceutical Composition 3) to the RLD. The results of the pk study for estradiol are summarized in Table 23. The p values for these data demonstrate statistical significance, as shown in Table 24.

TABLE 23

Statistical Summary of the Comparative Bioavailability Data for Unscaled Average BE studies of Estradiol, Least Square Geometric Means of Estradiol, Ratio of Means and 90% Confidence Intervals, Fasting/Fed Bioequivalence Study (Study No.: ESTR-1K-500-12); Dose 25 µg estradiol

| Parameter | Test | N | RLD | N | Ratio (%) | 90% C.I. |
|---|---|---|---|---|---|---|
| $C_{max}$ (pg/mL) | 23.0839 | 36 | 42.7024 | 36 | 54.06 | 44.18-66.14 |
| $AUC_{0-24}$ (pg · hr/mL) | 89.2093 | 36 | 292.0606 | 36 | 30.54 | 23.72-39.34 |

TABLE 24

P-values for table 23

| Effect | P-Value $C_{max}$ | $AUC_{0-24}$ |
|---|---|---|
| Treatment | <.0001 | <.0001 |
| Sequence | 0.4478 | 0.5124 |
| Period | 0.4104 | 0.7221 |

As illustrated in Table 23, baseline adjusted pk data illustrates that the formulations disclosed herein unexpectedly show a 54% decrease in $C_{max}$ and a 31% decrease in the AUC relative to the RLD. This result is desirable because the estradiol is intended only for local absorption. These data suggest a decrease in the circulating levels of estradiol relative to the RLD. Moreover, it is noteworthy to point out that the $C_{max}$ and AUC levels of estradiol relative to placebo are not statistically differentiable, which suggests that the formulations disclosed herein have a negligible systemic effect. As shown in Table 24, there was no significant difference between the test and reference products due to sequence and period effects. However, there was a significant difference due to treatment effect for both $C_{max}$ and AUC.

Pharmacokinetics for circulating total estrone, a metabolite of estradiol, is show in Table 25. These data show that the total circulating estrone for the formulations disclosed herein resulted in a 55% decrease in the $C_{max}$ for circulating estrone, and a 70% decrease in the AUC for circulating estrone.

TABLE 25

Statistical Summary of the Comparative Bioavailability Data for Unscaled Average BE studies of Estrone, Least Square Geometric Means, Ratio of Means and 90% Confidence Intervals, Fasting/Fed Bioequivalence Study (Study No.: ESTR-1K-500-12); Dose 25 µg estradiol

| Parameter | Test | N | RLD | N | Ratio (%) | 90% C.I. |
|---|---|---|---|---|---|---|
| $C_{max}$ (pg/mL) | 10.7928 | 36 | 23.5794 | 36 | 45.77 | 32.95 to 63.59 |
| $AUC_{0-24}$ (pg · hr/mL) | 51.2491 | 36 | 165.4664 | 36 | 30.97 | 19.8-48.45 |

TABLE 26

P-values for table 25

| Effect | P-Value $C_{max}$ | $AUC_{0-24}$ |
|---|---|---|
| Treatment | 0.0002 | <.0001 |
| Sequence | 0.1524 | 0.0464 |
| Period | 0.0719 | 0.0118 |

There was a significant difference between test and reference products due to treatment effect whereas there was no significant difference due to sequence and period effects for $C_{max}$. For AUC, there was a significant difference between test and reference products due to treatment, sequence, and period effects.

pk for circulating total estrone sulfate is shown in Table 27. These data show that the total circulating estrone sulfate for the pharmaceutical compositions disclosed herein resulted in a 33% decrease in the $C_{max}$ and a 42% decrease in the AUC for circulating estrone sulfate.

TABLE 27

Statistical Summary of the Comparative Bioavailability Data for Unscaled Average BE studies of Estrone Sulfate, Least Square Geometric Means of Estrone Sulfate, Ratio of Means and 90% Confidence Intervals, Fasting/Fed Bioequivalence Study (Study No.: ESTR-1K-500-12); Dose 25 µg estradiol

| Parameter | Test | N | RLD | N | Ratio (%) | 90% C.I. |
|---|---|---|---|---|---|---|
| $C_{max}$ (pg/mL) | 490.0449 | 36 | 730.5605 | 36 | 67.08 | 53.84-83.57 |
| $AUC_{0-24}$ (pg · hr/mL) | 4232.9914 | 36 | 7323.0827 | 36 | 57.80 | 43.23-77.29 |

TABLE 28

P-values for table 27

| Effect | P-Value $C_{max}$ | $AUC_{0-24}$ |
|---|---|---|
| Treatment | 0.0042 | 0.0031 |
| Sequence | 0.5035 | 0.9091 |
| Period | 0.1879 | 0.8804 |

There was a significant difference between test and reference products due to treatment effect whereas there was no significant difference due sequence and period effects for both $C_{max}$ and AUC.

Example 9 pk Study (10 µg Formulation)

A pk study was undertaken to compare the 10 µg formulation disclosed herein (Pharmaceutical Composition 2) to the RLD. The results of the pk study for estradiol are summarized in Table 29-40, and FIGS. 9-14.

A pk study was undertaken to compare pharmaceutical compositions disclosed herein having 10 µg of estradiol to the RLD. The results of the pk study for estradiol are summarized in tables 29-34, which demonstrate that the pharmaceutical compositions disclosed herein more effectively prevented systemic absorption of the estradiol. Table 35 shows that the pharmaceutical compositions disclosed herein had a 28% improvement over the RLD for systemic blood concentration $C_{max}$ and 72% AUC improvement over the RLD.

TABLE 29

Summary of Pharmacokinetic Parameters of Test product (T) of Estradiol - Baseline adjusted (N = 34)

| Pharmacokinetic Parameter | Arithmetic Mean ± Standard Deviation | Coefficient of Variation | Median | Minimum | Maximum |
|---|---|---|---|---|---|
| $C_{max}$ (pg/mL) | 15.7176 ± 7.9179 | 50.3761 | 13.9000 | 6.5000 | 49.6000 |
| $AUC_{0-24}$ (pg · hr/mL) | 53.0100 ± 19.5629 | 36.9041 | 49.9750 | 24.3000 | 95.1500 |
| $t_{max}$ (hr) | 1.98 ± 1.29 | 65.34 | 2.00 | 1.00 | 8.05 |

TABLE 30

Summary of Pharmacokinetic Parameters of Reference product (R) of Estradiol - Baseline adjusted (N = 34)

| Pharmacokinetic Parameter | Arithmetic Mean ± Standard Deviation | Coefficient of Variation | Median | Minimum | Maximum |
|---|---|---|---|---|---|
| $C_{max}$ (pg/mL) | 24.1882 ± 11.9218 | 49.2877 | 24.1500 | 1.0000 | 55.3000 |
| $AUC_{0-24}$ (pg · hr/mL) | 163.8586 ± 72.0913 | 43.9960 | 158.0375 | 2.0000 | 304.8500 |
| $t_{max}$ (hr) | 10.53 ± 5.58 | 52.94 | 8.06 | 2.00 | 24.00 |

TABLE 31

Geometric Mean of Test Product (T) and Reference product (R) of Estradiol - Baseline adjusted (N = 34)

| Pharmacokinetic Parameter | Geometric Mean Test Product (T) | Geometric Mean Reference Product (R) |
|---|---|---|
| $C_{max}$ (pg/mL) | 14.3774 | 20.3837 |
| $AUC_{0-24}$ (pg · hr/mL) | 49.6231 | 132.9218 |
| $t_{max}$ (hr) | 1.75 | 9.28 |

TABLE 32

Statistical Results of Test product (T) versus Reference product (R) for Estradiol - Baseline adjusted (N = 34)

| Pharmacokinetic Parameter | Geometric Least Square Mean Test Product (T) | Geometric Least Square Mean Reference Product (R) | Intra Subject CV % | T/R Ratio % | 90% Confidence Interval |
|---|---|---|---|---|---|
| $C_{max}$ (pg/mL) | 14.4490 | 20.1980 | 60.68 | 71.54* | 56.82-90.08 |
| $AUC_{0-24}$ (pg · hr/mL) | 49.7310 | 131.0400 | 70.64 | 37.95* | 29.21-49.31 |

*Comparison was detected as statistically significant by ANOVA ($\alpha = 0.05$).

TABLE 33

Summary of Pharmacokinetic Parameters of Test product (T) of Estrone - Baseline adjusted (N = 33)

| Pharmacokinetic Parameter | Arithmetic Mean ± Standard Deviation | Coefficient of Variation | Median | Minimum | Maximum |
|---|---|---|---|---|---|
| $C_{max}$ (pg/mL) | 6.8485 ± 6.5824 | 96.1149 | 5.4000 | 1.3000 | 36.3000 |
| $AUC_{0-24}$ (pg · hr/mL) | 34.7051 ± 27.9541 | 80.5476 | 30.8500 | 3.3500 | 116.7500 |
| $t_{max}$ (hr) | 9.12 ± 8.83 | 96.80 | 4.00 | 1.00 | 24.00 |

TABLE 34

Summary of Pharmacokinetic Parameters of Reference product (R) of Estrone - Baseline adjusted (N = 33)

| Pharmacokinetic Parameter | Arithmetic Mean ± Standard Deviation | Coefficient of Variation | Median | Minimum | Maximum |
|---|---|---|---|---|---|
| $C_{max}$ (pg/mL) | 8.8333 ± 7.1469 | 80.9086 | 6.7000 | 2.7000 | 30.3000 |
| $AUC_{0-24}$ (pg · hr/mL) | 63.0042 ± 46.5484 | 73.8814 | 51.2800 | 8.8000 | 214.0000 |
| $t_{max}$ (hr) | 11.16 ± 7.24 | 64.95 | 10.00 | 4.00 | 24.00 |

TABLE 35

Geometric Mean of Test Product (T) and Reference product (R) of Estrone - Baseline adjusted (N = 33)

| Pharmacokinetic Parameter | Geometric Mean Test Product (T) | Geometric Mean Reference Product (R) |
|---|---|---|
| $C_{max}$ (pg/mL) | 5.1507 | 6.9773 |
| $AUC_{0-24}$ (pg · hr/mL) | 24.2426 | 48.2377 |
| $t_{max}$ (hr) | 5.87 | 9.07 |

TABLE 36

Statistical Results of Test product (T) versus Reference product (R) for Estrone - Baseline adjusted (N = 33)

| Pharmacokinetic Parameter | Geometric Least Square Mean Test Product (T) | Geometric Least Square Mean Reference Product (R) | Intra Subject CV % | T/R Ratio % | 90% Confidence Interval |
|---|---|---|---|---|---|
| $C_{max}$ (pg/mL) | 5.1620 | 6.9280 | 47.59 | 74.50* | 61.69-89.97 |
| $AUC_{0-24}$ (pg · hr/mL) | 24.1960 | 47.9020 | 73.66 | 50.51* | 38.37-66.50 |

*Comparison was detected as statistically significant by ANOVA ($\alpha = 0.05$).

The pk data for total estrone likewise demonstrated reduced systemic exposure when compared to the RLD. Table 33 shows the pharmaceutical compositions disclosed herein reduced systemic exposure by 25% for $C_{max}$ and 49% for AUC.

The pk data for estrone sulfate likewise demonstrated reduced systemic exposure when compared to the RLD. Table 37 shows the pharmaceutical compositions disclosed herein reduced systemic exposure by 25% for $C_{max}$ and 42% for AUC.

TABLE 37

Summary of Pharmacokinetic Parameters of Test product
(T) of Estrone Sulfate - Baseline adjusted (N = 24)

| Pharmacokinetic Parameter | Arithmetic Mean ± Standard Deviation | Coefficient of Variation | Median | Minimum | Maximum |
|---|---|---|---|---|---|
| $C_{max}$ (ng/mL) | 13.9042 ± 7.0402 | 50.6339 | 11.1500 | 1.3000 | 39.0000 |
| $AUC_{0-24}$ (ng · hr/mL) | 97.9953 ± 80.8861 | 82.5408 | 76.2750 | 5.1025 | 338.0000 |
| $t_{max}$ (hr) | 6.33 ± 4.56 | 71.93 | 4.00 | 4.00 | 24.00 |

TABLE 38

Summary of Pharmacokinetic Parameters of Reference product
(R) of Estrone Sulfate - Baseline adjusted (N = 24)

| Pharmacokinetic Parameter | Arithmetic Mean ± Standard Deviation | Coefficient of Variation | Median | Minimum | Maximum |
|---|---|---|---|---|---|
| $C_{max}$ (ng/mL) | 19.2542 ± 11.3633 | 59.0173 | 15.2000 | 7.0000 | 53.7000 |
| $AUC_{0-24}$ (ng · hr/mL) | 177.6208 ± 166.2408 | 93.5931 | 124.0000 | 20.0000 | 683.0500 |
| $t_{max}$ (hr) | 10.33 ± | 54.05 | 10.00 | 2.00 | 24.00 |

TABLE 39

Geometric Mean of Test Product (T) and Reference product
(R) of Estrone Sulfate - Baseline adjusted (N = 24)

| Pharmacokinetic Parameter | Geometric Mean Test Product (T) | Geometric Mean Reference Product (R) |
|---|---|---|
| $C_{max}$ (ng/mL) | 12.1579 | 16.8587 |
| $AUC_{0-24}$ (ng · hr/mL) | 66.5996 | 121.5597 |
| $t_{max}$ (hr) | 5.49 | 8.83 |

TABLE 40

Statistical Results of Test product (T) versus Reference product
(R) for Estrone Sulfate - Baseline adjusted (N = 24)

| Pharmacokinetic Parameter | Geometric Least Square Mean Test Product (T) | Geometric Least Square Mean Reference Product (R) | Intra Subject CV % | T/R Ratio % | 90% Confidence Interval |
|---|---|---|---|---|---|
| $C_{max}$ (ng/mL) | 12.3350 | 16.5470 | 48.02 | 74.55* | 59.43-93.51 |
| $AUC_{0-24}$ (ng · hr/mL) | 68.5260 | 118.4170 | 73.87 | 57.87* | 41.68-80.35 |

*Comparison was detected as statistically significant by ANOVA ($\alpha$ = 0.05).

While the pharmaceutical compositions and methods have been described in terms of what are presently considered to be practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar embodiments. This disclosure includes any and all embodiments of the following claims.

The invention claimed is:

1. A pessary comprising about 25 µg of 17β-estradiol in a solubilizing agent comprising a medium chain oil, wherein after a single administration of the pessary to a patient provides, in a plasma sample from the patient:
   1) a corrected geometric mean peak plasma concentration ($C_{max}$) of 17β-estradiol of about 19 pg*hr/ml to about 29 pg*hr/ml; and
   2) a corrected geometric mean area under the curve $(AUC)_{0-24}$ of 17β-estradiol of about 75 pg*hr/ml to about 112 pg*hr/ml,
   wherein 17β-estradiol is the only active hormone in the pessary.

2. The pessary of claim 1, wherein administration of the pessary to a patient provides, in a plasma sample from the patient:
   1) a corrected geometric mean peak plasma concentration ($C_{max}$) of estrone of about 9 pg*hr/ml to about 14 pg*hr/ml; and
   2) a corrected geometric mean area under the curve $(AUC)_{0-24}$ of estrone of about 43 pg*hr/ml to about 65 pg*hr/ml.

3. The pessary of claim 1, wherein administration of the pessary to a patient provides, in a plasma sample from the patient:
   1) a corrected geometric mean peak plasma concentration (Cmax) of estrone sulfate of about 416 pg*hr/ml to about 613 pg*hr/ml; and
   2) a corrected geometric mean area under the curve $(AUC)_{0-24}$ of estrone sulfate of about 3598 pg*hr/ml to about 5291 pg*hr/ml.

4. A pessary comprising about 10 µg of 17β-estradiol in a solubilizing agent comprising a medium chain oil, wherein after a single administration of the pessary to a patient provides, in a plasma sample from the patient:
   1) a corrected geometric mean peak plasma concentration ($C_{max}$) of 17β-estradiol of about 12 pg*hr/ml to about 18 pg*hr/ml; and
   2) a corrected geometric mean area under the curve $(AUC)_{0-24}$ of 17β-estradiol of about 42 pg*hr/ml to about 63 pg*hr/ml,
   wherein 17β-estradiol is the only active hormone in the pessary.

5. The pessary of claim 4, wherein the pessary further provides a corrected geometric mean time to peak plasma concentration ($T_{max}$) of 17β-estradiol of about 1 hrs to about 3 hrs.

6. The pessary of claim 4, wherein administration of the pessary to a patient provides, in a plasma sample from the patient:
   1) a corrected geometric mean peak plasma concentration ($C_{max}$) of estrone of about 4 pg*hr/ml to about 7 pg*hr/ml; and
   2) a corrected geometric mean area under the curve $(AUC)_{0-24}$ of estrone of about 20 pg*hr/ml to about 31 pg*hr/ml.

7. The pessary of claim 6, wherein the pessary further provides a corrected geometric mean time to peak plasma concentration ($T_{max}$) of estrone of about 4 hrs to about 8 hrs.

8. The pessary of claim 4, wherein administration of the pessary to a patient provides, in a plasma sample from the patient:
   1) a corrected geometric mean peak plasma concentration ($C_{max}$) of estrone sulfate of about 10 pg*hr/ml to about 16 pg*hr/ml; and 2) a corrected geometric mean area under the curve (AUC)$_{0-24}$ of estrone sulfate of about 56 pg*hr/ml to about 84 pg*hr/ml.

9. The pessary of claim 8, wherein the pessary further provides a corrected geometric mean time to peak plasma concentration (T$_{max}$) of estrone sulfate of about 4 hrs to about 7 hrs.

10. A pessary comprising about 4 µg of 17β-estradiol in a solubilizing agent comprising a medium chain oil, wherein after a single administration of the pessary to a patient provides, in a plasma sample from the patient:
 1) a corrected geometric mean peak plasma concentration (Cmax) of 17β-estradiol of about 4 pg*hr/ml to about 8 pg*hr/ml; and
 2) a corrected geometric mean area under the curve (AUC)$_{0-24}$ of 17β-estradiol of about 16 pg*hr/ml to about 26 pg*hr/ml, wherein 17β-estradiol is the only active hormone in the pessary.

11. The pessary of claim 10, wherein the pessary further provides a corrected geometric mean time to peak plasma concentration (T$_{max}$) of 17β-estradiol of about 0.25 hrs to about 2 hrs.

12. The pessary of claim 10, wherein administration of the pessary to a patient provides, in a plasma sample from the patient:
 1) a corrected geometric mean peak plasma concentration (C$_{max}$) of estrone of about 1 pg*hr/ml to about 3 pg*hr/ml; and
 2) a corrected geometric mean area under the curve (AUC)$_{0-24}$ of estrone of about 8 pg*hr/ml to about 13 pg*hr/ml.

13. The pessary of claim 12, wherein the pessary further provides a corrected geometric mean time to peak plasma concentration (T$_{max}$) of estrone of about 1 hrs to about 4 hrs.

14. The pessary of claim 10, wherein administration of the pessary to a patient provides, in a plasma sample from the patient:
 1) a corrected geometric mean peak plasma concentration (C$_{max}$) of estrone sulfate of about 4 pg*hr/ml to about 7 pg*hr/ml; and
 2) a corrected geometric mean area under the curve (AUC)$_{0-24}$ of estrone sulfate of about 22 pg*hr/ml to about 34 pg*hr/ml.

15. The pessary of claim 14, wherein the pessary further provides a corrected geometric mean time to peak plasma concentration (T$_{max}$) of estrone sulfate of about 1 hrs to about 3 hrs.

16. The pessary of claim 1, wherein the medium chain oil comprises at least one C6-C12 fatty acid or a glycol, monoglyceride, diglyceride, or triglyceride ester thereof.

17. The pessary of claim 1, wherein the medium chain oil comprises a monoglyceride, diglyceride, or triglyceride ester of the at least one C6-C12 fatty acid.

18. The pessary of claim 4, wherein the medium chain oil comprises at least one C6-C12 fatty acid or a glycol, monoglyceride, diglyceride, or triglyceride ester thereof.

19. The pessary of claim 4, wherein the medium chain oil comprises a monoglyceride, diglyceride, or triglyceride ester of the at least one C6-C12 fatty acid.

20. The pessary of claim 10, wherein the medium chain oil comprises at least one C6-C12 fatty acid or a glycol, monoglyceride, diglyceride, or triglyceride ester thereof.

21. The pessary of claim 10, wherein the medium chain oil comprises a monoglyceride, diglyceride, or triglyceride ester of the at least one C6-C12 fatty acid.

* * * * *

UNITED STATES PATENT AND TRADEMARK OFFICE
CERTIFICATE OF CORRECTION

PATENT NO. : 9,289,382 B2
APPLICATION NO. : 14/624051
DATED : March 22, 2016
INVENTOR(S) : Brian A. Bernick and Julia M. Amadio Page 1 of 2

It is certified that error appears in the above-identified patent and that said Letters Patent is hereby corrected as shown below:

In the Specification

Column 2, Lines 52-53: Delete "PEG-6 palmitostearate" and insert in its place --PEG-6 stearate--.

Column 2, Lines 59-60 and 67: Delete each instance of "pg*hr/ml" and insert in its place --pg/ml--.

Column 3, Lines 1, 8-9, 16-17, 26-27, 36-37, 47-48, 57-58 and 67: Delete each instance of "pg*hr/ml" and insert in its place --pg/ml--.

Column 4, Lines 1, 11, 14, 27, 30, 43 and 46: Delete each instance of "pg*hr/ml" and insert in its place --pg/ml--.

Column 16, Line 40: Delete "PEG-6 palmitostearate" and insert in its place --PEG-6 stearate--.

Column 25, Lines 26-27, 34-35, 43-44, 53-54 and 63-64: Delete each instance of "pg*hr/ml" and insert in its place --pg/ml--.

Column 26, Lines 7-8, 20, 28-29, 37, 58 and 61: Delete each instance of "pg*hr/ml" and insert in its place --pg/ml--.

Column 27, Lines 4-7 and 17-20: Delete each instance of "pg*hr/ml" and insert in its place --pg/ml--.

In the Claims

Column 56, Claim 1, Lines 7-8: Delete each instance of "pg*hr/ml" and insert in its place --pg/ml--.

Column 56, Claim 2, Line 19: Delete each instance of "pg*hr/ml" and insert in its place --pg/ml--.

Column 56, Claim 3, Lines 28-29: Delete each instance of "pg*hr/ml" and insert in its place --pg/ml--.

Signed and Sealed this
Twentieth Day of August, 2019

Andrei Iancu
*Director of the United States Patent and Trademark Office*

CERTIFICATE OF CORRECTION (continued)
U.S. Pat. No. 9,289,382 B2

Column 56, Claim 4, Lines 39-40: Delete each instance of "pg*hr/ml" and insert in its place --pg/ml--.

Column 56, Claim 6, Lines 54-55: Delete each instance of "pg*hr/ml" and insert in its place --pg/ml--.

Column 56, Claim 8, Lines 66-67: Delete each instance of "pg*hr/ml" and insert in its place --pg/ml--.

Column 57, Claim 10, Lines 12-13: Delete each instance of "pg*hr/ml" and insert in its place --pg/ml--.

Column 57, Claim 12, Lines 26-27: Delete each instance of "pg*hr/ml" and insert in its place --pg/ml--.

Column 58, Claim 14, Lines 5-6: Delete each instance of "pg*hr/ml" and insert in its place --pg/ml--.

UNITED STATES PATENT AND TRADEMARK OFFICE
CERTIFICATE OF CORRECTION

PATENT NO. : 9,289,382 B2  
APPLICATION NO. : 14/624051  
DATED : March 22, 2016  
INVENTOR(S) : Brian A. Bernick et al.

Page 1 of 1

It is certified that error appears in the above-identified patent and that said Letters Patent is hereby corrected as shown below:

On the Title Page

At item (72), please add inventor --Peter H.R. Persicaner, Boca Raton, FL (US)--

Signed and Sealed this
Twenty-first Day of July, 2020

Andrei Iancu
*Director of the United States Patent and Trademark Office*